United States Patent
Buchmann et al.

(10) Patent No.: US 6,340,706 B1
(45) Date of Patent: Jan. 22, 2002

(54) LEUKOTRIENE-$B_4$ DERIVATIVES, IN PARTICULAR 7-METHYLCYCLOHEXYL-$LTB_4$ ANTAGONISTS

(75) Inventors: Bernd Buchmann, Hohen Neuendorf; Wolfgang Frohlich, Berlin; Claudia Giesen, Berlin; Hartwig Hennekes, Berlin; Stefan Jaroch, Berlin; Werner Skuballa, Berlin, all of (DE)

(73) Assignee: Schering Aktiengesellschaft, Berlin (DE)

( * ) Notice: Subject to any disclaimer, the term of this patent is extended or adjusted under 35 U.S.C. 154(b) by 0 days.

(21) Appl. No.: 09/424,449
(22) PCT Filed: May 22, 1998
(86) PCT No.: PCT/EP98/03138
  § 371 Date: Mar. 10, 2000
  § 102(e) Date: Mar. 10, 2000
(87) PCT Pub. No.: WO98/52914
  PCT Pub. Date: Nov. 26, 1998

(30) Foreign Application Priority Data

May 23, 1997 (DE) ........................ 197 22 846.1

(51) Int. Cl.[7] ............ A61K 31/20; C07C 69/74
(52) U.S. Cl. .................... 514/560; 560/128
(58) Field of Search ............. 514/560; 560/128

(56) References Cited

FOREIGN PATENT DOCUMENTS

| DE | 4236540 | 6/1994 |
|---|---|---|
| DE | 4242390 | 6/1994 |
| WO | 9520563 | 8/1995 |

*Primary Examiner*—Kathleen Kahler Fonda
(74) *Attorney, Agent, or Firm*—Millen, White, Zelano & Branigan, P.C.

(57) ABSTRACT

The invention relates to leukotriene $B_4$ derivatives of general formula (I) in which $R_1$ stands for $CH_2OH$, $CH_3$, $CF_3$, $COOR_4$, $CONR_5R_6$; $R_2$ stands for H or an organic acid radical with 1–15 C atoms; $R_3$ stands for H; $R_4$ is hydrogen, $C_1$–$C_{10}$-alkyl, $C_3$–$C_{10}$-cycloalkyl, a $C_6$–$C_{10}$-aryl radical optionally substituted by 1–3 halogen, phenyl, $C_1$–$C_4$-alkyl, $C_1$–$C_4$-alkoxy, fluoromethyl, chloromethyl, trifluoromethyl, carboxyl or hydroxy, or $CH_2$—CO—($C_6$–$C_{10}$) aryl, or a 5–6 link ring with at least 1 heteroatom; A is a trans-, trans-CH=CH—CH=CH, a —$CH_2CH_2$—CH=CH— or a tetramethylene group; B is a $C_1$–$C_{10}$ linear or branched-chain aklylene group or the group (a) or (b); D is a direct bonding, oxygen, sulphur, —C≡C—, —CH=$CR_7$, or a direct bonding with B. The invention also relates to salts thereof, having physiologically compatible bases and their cyclodextrin clathrates. The inventive substances can be used as pharmaceutical preparations

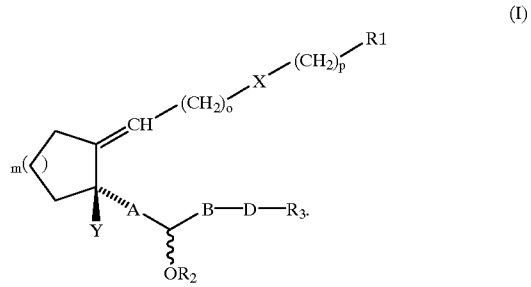

(I)

16 Claims, No Drawings

LEUKOTRIENE-B₄ DERIVATIVES, IN PARTICULAR 7-METHYLCYCLOHEXYL-LTB₄ ANTAGONISTS

This is the U.S. National Stage entry under 35 U.S.C. 371 of PCT/EP98/03138, filed May 22, 1998.

The invention relates to new leukotriene-$B_4$ derivatives, process for their production and their use as pharmaceutical agents. The new compounds are optically active structural analogs of previously known leukotriene-$B_4$ antagonists, which contain a six-membered ring as a basic structural element (DE 39 17 597, DE 42 27 790, DE 42 42 390).

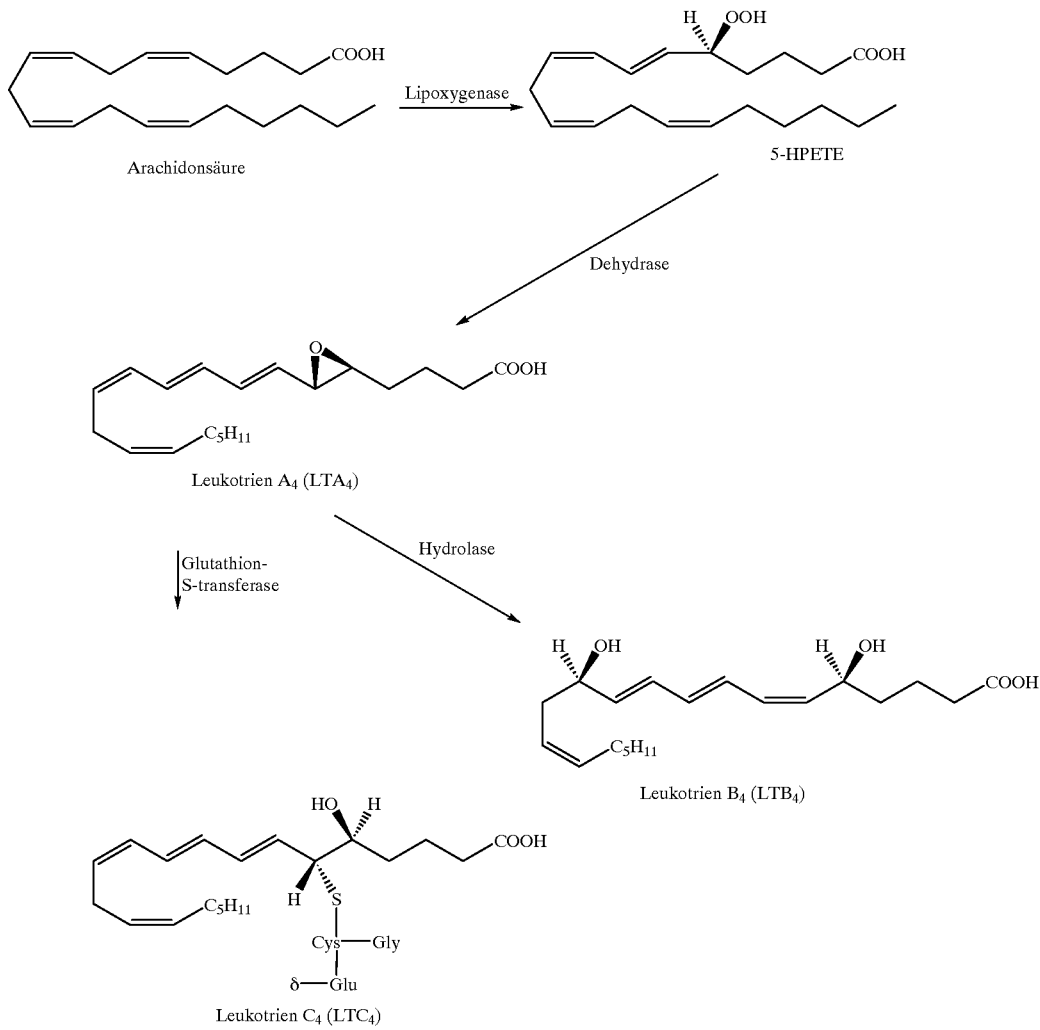

KEY
Arachidonsäure=arachidonic acid
Leukotrien A₄ (LTA₄)=leukotriene A₄ (LTA₄)
Glutathion-S-transferase=glutathione-S-transferase
Leukotrien B₄ (LTB₄)=leukotriene B₄ (LTB₄)
Leukotrien C₄ (LTC₄)=leukotriene C₄ (LTC₄)

Leukotriene $B_4$ (LTB₄) was discovered by B. Samuelsson et al. as a metabolite of the arachidonic acid. In the biosynthesis, leukotriene $A_4$ is formed by the enzyme 5-lipoxygenase first as a central intermediate product, which then is converted by a specific hydrolase into the $LTB_4$.

The nomenclature of the leukotrienes can be deduced from the following works:

a) B. Samuelsson et al., Prostaglandins 19, 654 (1980); 17, 785 (1979);

b) C. N. Serhan et al., Prostaglandins 34, 201 (1987).

The physiological and especially the pathophysiological importance of leukotriene $B_4$ is summarized in several more recent works: a) The Leukotrienes, Chemistry and Biology eds. L. W. Chakrin, D. M. Bailey, Academic Press 1984. b) J. W. Gillard et al., Drugs of the Future 12, 453 (1987). c) B. Samuelsson, Sciences 237, 1171 (1987). d) C. W. Parker, Drug Development Research 10, 277 (1987). e) W. R. Henderson, Annals of Internal Medicine 121, 684 (1994). It follows from the above that $LTB_4$ is an important inflammation mediator for inflammatory diseases, in which leukocytes invade the affected tissue.

The effects of $LTB_4$ are triggered on the cellular plane by the binding of $LTB_4$ to a specific receptor.

It is known concerning $LTB_4$ that it causes the adhesion of leukocytes to the blood vessel wall. $LTB_4$ is chemotactically active, i.e., it triggers a directed migration of leukocytes in the direction of a gradient of increasing concentration. Furthermore, it indirectly changes the vascular permeability based on its chemotactic activity, whereby a synergism with prostaglandin $E_2$ is observed. $LTB_4$ obviously plays a decisive role in inflammatory, allergic and immunological processes.

Leukotrienes and especially $LTB_4$ are involved in skin diseases, which are accompanied by inflammatory processes (increased vascular permeability and formation of edemas, cell infiltration), increased proliferation of skin cells and itching, such as, for example, in eczemas, erythemas, psoriasis, pruritus and acne. Pathologically increased leukotriene concentrations are involved either causally in the development of many dermatitides or there is a connection between the persistence of the dermatitides and the leukotrienes. Clearly increased leukotriene concentrations were measured, for example, in the skin of patients with psoriasis, atopic dermatitis, allergic contact dermatitis, bullous pemiphigoids, delayed duchurticaria and allergic vasculitis.

Leukotrienes and especially $LTB_4$ are also involved in the diseases of internal organs, for which an acute or chronic inflammatory component was described, e.g.: joint diseases (rheumatic arthritis); diseases of the respiratory tract (asthma and chronically obstructive lung diseases (OPD)); inflammatory intestinal diseases (ulcerous colitis and Crohn's disease); as well as reperfusion damages (to the heart, intestinal or renal tissues), which result by the temporary pathological obstruction of blood vessels, such as glomerulonephritis, NSAID gastropathies, multiple sclerosis, rhinitis and inflammatory eye diseases.

Further, leukotrienes and especially $LTB_4$ are involved in the disease of multiple sclerosis and in the clinical appearance of shock (triggered by infections, burns or in complications in kidney dialysis or other separately discussed perfusion techniques).

In addition, leukotrienes and especially $LTB_4$ have an effect on the formation of white blood cells in the bone marrow, on the growth of unstriped muscle cells, of keratinocytes and of B-lymphocytes. $LTB_4$ is therefore involved in diseases with inflammatory processes and in diseases with pathologically increased formation and growth of cells.

For example, leukemia or arteriosclerosis represent diseases with this clinical appearance.

Leukotrienes and especially $LTB_4$ and its derivatives are suitable for reducing elevated triglyceride levels and thus act in an anti-arteriosclerotic manner and against obesity.

By the antagonizing of the effects, especially by $LTB_4$, the active ingredients and their forms for dispensing of this invention are specific medicines for diseases of humans and animals, in which especially leukotrienes play a pathological role.

Besides the therapeutic possibilities, which can be derived from an antagonizing of $LTB_4$ action with $LTB_4$ analogs, the usefulness and potential use of leukotriene-$B_4$ agonists for the treatment of fungus diseases of the skin were also able to be shown (H. Katayama, Prostaglandins 34, 797 (1988)).

The invention relates to leukotriene-$B_4$ derivatives of general formula I

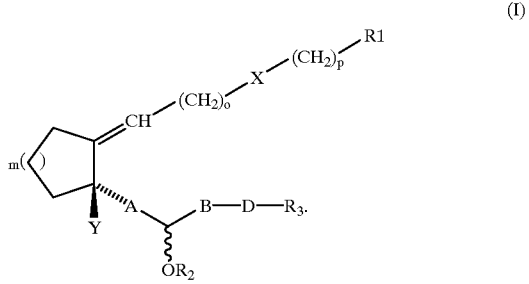

in which
$R_1$ represents $CH_2OH$, $CH_3$, $CF_3$, $COOR_4$, $CONR_5R_6$ and $R_2$ represents H or an organic acid radical with 1–15 C atoms, $R_3$ symbolizes H; $C_1$–$C_{14}$ alkyl, $C_3$–$C_{10}$ cycloalkyl optionally substituted in one or more places; $C_6$–$C_{10}$ aryl radicals, independently of one another, optionally substituted in one or more places by halogen, phenyl, $C_1$–$C_4$ alkyl, $C_1$–$C_4$ alkoxy, fluoromethyl, chloromethyl, trifluoromethyl, carbonyl, carboxyl or hydroxy; or a 5- to 6-membered aromatic heterocyclic ring with at least 1 heteroatom, $R_4$ means hydrogen, $C_1$–$C_{10}$ alkyl, $C_3$–$C_{10}$ cycloalkyl, $C_6$–$C_{10}$ aryl radicals optionally substituted by 1–3 halogen, phenyl, $C_1$–$C_4$ alkyl, $C_1$–$C_4$ alkoxy, fluoromethyl, chloromethyl, trifluoromethyl, carboxyl or hydroxy; $CH_2$—CO—($C_6$–$C_{10}$) aryl or a 5- to 6-membered ring with at least 1 heteroatom;

A symbolizes a trans, trans—CH=CH—CH=CH, a —$CH_2CH_2$—CH=CH—or a tetramethylene group;

B symbolizes a $C_1$–$C_{10}$ straight-chain or branched-chain alkylene group, which optionally can be substituted by fluorine or the group

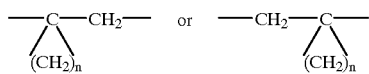

D can mean a direct bond, oxygen, sulfur, —C≡C—, —CH=$CR_7$ or together with B can also mean a direct bond;

$r_5$ and $R_6$ are the same or different, and represent H or $C_1$–$C_4$ alkyl optionally substituted by hydroxy groups, or $R_6$ represents H and $R_5$ represents $C_1$–$C_{15}$ alkanoyl or $R_8SO_2$, $R_7$ means H, $C_1$–$C_5$ alkyl, chlorine, bromine, $R_8$ has the same meaning as $R_3$, m means 1–3, o means 0–5, p means 0–5, x is a direct bond, oxygen, sulfur, y is a $C_1$–$C_8$ alkyl optionally substituted in one or more places, $C_3$–$C_{10}$ cycloalkyl, and n is 2–5, and, if $R_4$ means hydrogen, their salts with physiologically compatible bases and their cyclodextrin clathrates.

The group $OR_2$ can be in α- or β-position. Formula I comprises both racemates and the possible pure diastereomers and enantiomers.

As alkyl groups $R_4$, straight-chain or branched-chain alkyl groups with 1–10 C atoms are considered, such as, for example, methyl, ethyl, propyl, butyl, isobutyl, tert-butyl, pentyl, neopentyl, hexyl, heptyl, decyl.

Alkyl groups $R_4$ can optionally be substituted in one or more places by halogen atoms, alkoxy groups, optionally substituted aryl or aroyl groups with 6–10 C atoms (relative to possible substituents, see under aryl $R_4$), dialkylamino and trialkylammonium with 1–4 C atoms in the alkyl portion, whereby single substitution is to be preferred. As substituents, for example, fluorine, chlorine or bromine, phenyl, dimethylamino, diethylamino, methoxy, ethoxy can be mentioned. As preferred alkyl groups $R_4$, those with 1–4 C atoms can be mentioned.

Cycloalkyl group $R_4$ can contain 3–10, preferably 5 and 6 carbon atoms in the ring. The rings can be substituted by alkyl groups with 1–4 carbon atoms. For example, cyclopentyl, cyclohexyl, methylcyclohexyl can be mentioned.

As aryl groups $R_4$, both substituted and unsubstituted aryl groups with 6–10 C atoms are considered, such as, for example, phenyl, 1-naphthyl and 2-naphthyl, which can be substituted in each case by 1–3 halogen atoms (F, Cl, Br), a phenyl group, 1–3 alkyl groups with, in each case, 1–4 C atoms, a chloromethyl, a fluoromethyl, trifluoromethyl, carboxyl, hydroxy or alkoxy group with 1–4 C atoms. Preferred substituents in 3- and 4-position on the phenyl ring are, for example, fluorine, chlorine, alkoxy or trifluoromethyl, in 4-position, however, hydroxy.

As heterocyclic groups $R_4$, 5- and 6-membered aromatic heterocycles that contain at least 1 heteroatom, preferably nitrogen, oxygen or sulfur, are suitable. For example, 2-furyl, 2-thienyl, 2-pyridyl, 3-pyridyl, 4-pyridyl, oxazolyl, thiazolyl, pyrimidinyl, pyridazinyl, 3-furyl, 3-thienyl, 2-tetrazolyl, i.a., can be mentioned.

As acid radical $R_5$, such physiologically compatible acids are suitable. Preferred acids are organic carboxylic acids and sulfonic acids with 1–15 carbon atoms, which belong to the aliphatic, cycloaliphatic, aromatic, aromatic-aliphatic and heterocyclic series. These acids can be saturated, unsaturated and/or polybasic and/or substituted in the usual way. As examples of the substituents, $C_{1-4}$ alkyl, hydroxy, $C_{1-4}$ alkoxy, oxo or amino groups or halogen atoms (F, Cl, Br) can be mentioned. For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopropylacetic acid, cyclopentylacetic acid, cyclohexylacetic acid, cyclopropanecarboxylic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid; benzoic acids substituted with halogen (F, Cl, Br) or trifluoromethyl, hydroxy, $C_{1-4}$ alkoxy or carboxy groups; nicotinic acid, isonicotinic acid, furan-2-carboxylic acid, cyclopentylpropionic acid. As preferred arylsulfonyl radicals and alkanesulfonyl radicals $R_8SO_2$, those are to be considered that are derived from a sulfonic acid with up to 10 carbon atoms. As sulfonic acids, for example, methanesulfonic acid, ethanesulfonic acid, isopropanesulfonic acid, cyclohexanesulfonic acid, benzenesulfonic acid, p-toluenesulfonic acid, p-chlorobenzenesulfonic acid, N,N-dimethylaminosulfonic acid, N,N-diisobutylaminosulfonic acid, N,N-dibutylaminosulfonic acid, pyrrolidino, piperidino, piperazino, M-methylpiperazino and morpholinosulfonic acid are suitable.

As alkyl groups $R_3$, straight-chain and branched-chain, saturated and unsaturated alkyl radicals, preferably saturated, with 1–14, especially 1–10 C atoms, are suitable, which optionally can be substituted by optionally substituted phenyl (for substitution, see under aryl $R_5$). For example, methyl, ethyl, propyl, butyl, isobutyl, tert-butyl, pentyl, hexyl, heptyl, octyl, butenyl, isobutenyl, propenyl, pentenyl, benzyl, m- and p-chlorobenzyl groups can be mentioned. If alkyl groups $R_3$ are halogen-substituted, fluorine, chlorine and bromine are suitable as halogens.

As examples of halogen-substituted alkyl groups $R_3$, alkyls with terminal trifluoromethyl groups are considered.

Cycloalkyl group $R_3$ can contain 3–10, preferably 3–6 carbon atoms in the ring. The rings can be substituted by alkyl groups with 1–4 carbon atoms optionally by halogens. For example, cyclopropyl, cyclobutyl, cyclopentyl, cyclohexyl, methyl-cyclohexyl, fluorocyclohexyl can be mentioned.

As substituted or unsubstituted aryl groups $R_3$, for example, phenyl, 1-naphthyl and 2-naphthyl, which can be substituted in each case by 1–3 halogen atoms (F, Cl, Br), a phenyl group, 1–3 alkyl groups with 1–4 C atoms in each case, a chloromethyl, fluoromethyl, trifluoromethyl, carboxyl, $C_1$–$C_4$ alkoxy or hydroxy group, are considered. Preferred is the substitution in 3- and 4-position on the phenyl ring by, for example, fluorine, chlorine, alkoxy or trifluoromethyl or in 4-position by hydroxy.

As heterocyclic aromatic groups $R_3$, 5- and 6-membered heterocycles that contain at least 1 heteroatom, preferably nitrogen, oxygen or sulfur, are suitable. For example, 2-furyl, 1-thienyl, 2-pyridyl, 3-pyridyl, 4-pyridyl, oxazolyl, thiazolyl, pyrimidinyl, pyridazinyl, pyrazinyl, 3-furyl, 3-thienyl, i.a., can be mentioned.

As alkylene groups B, straight-chain or branched, saturated or unsaturated alkylene radicals, preferably saturated with 1–10, especially with 1–5 C atoms, are suitable, which optionally can be substituted by fluorine atoms. For example, methylene, fluoromethylene, difluoromethylene, ethylene, 1,2-propylene, ethylethylene, trimethylene, tetramethylene, pentamethylene, 1,2-difluoroethylene, 1-fluoroethylene, 1-methyltetramethylene, 1-methyl-trimethylene, 1-methylene-ethylene, 1-methylene-tetramethylene can be mentioned.

In addition, alkylene group B can represent the group

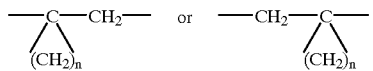

whereby n=2–5, preferably 3–5.

As acid radicals $R_2$, those of physiologically compatible acid radicals are suitable. Preferred acids are organic carboxylic acids and sulfonic acids with 1–15 carbon atoms, which belong to the aliphatic, cycloaliphatic, aromatic, aromatic-aliphatic or heterocyclic series. These acids can be substituted saturated, unsaturated and/or polybasic and/or in the usual way. As examples of the substituents, $C_{1-4}$ alkyl, hydroxy, $C_{1-4}$ alkoxy, oxo or amino groups or halogen atoms (F, Cl, Br) can be mentioned. For example, the following carboxylic acids can be mentioned: formic acid, acetic acid, propionic acid, butyric acid, isobutyric acid, valeric acid, isovaleric acid, caproic acid, enanthic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopentylacetic acid, cyclohexylacetic acid, cyclohexanecarboxylic acid, phenylacetic acid, phenoxyacetic acid, methoxyacetic acid, ethoxyacetic acid, mono-, di- and trichloroacetic acid, aminoacetic acid, diethylaminoacetic acid, piperidinoacetic acid, morpholinoacetic acid, lactic acid, succinic acid, adipic acid, benzoic acid; benzoic acids substituted with halogen (F, Cl, Br) or trifluoromethyl, hydroxy, $C_{14}$ alkoxy or carboxy groups; nicotinic acid, isonicotinic acid, furan-2-carboxylic acid, cyclopentylpropionic acid. As preferred acid radicals $R_2$ and $R_3$, those acyl radicals with up to 10 carbon atoms are considered.

Alkyl radicals $R_5$ and $R_6$, which optionally contain hydroxy groups, are straight-chain or branched alkyl radicals, especially straight-chain, such as, for example, methyl, ethyl, propyl, butyl, pentyl, hexyl, especially preferably methyl.

$R_7$ as $C_{1-5}$ alkyl means straight-chain or branched-chain alkyl radicals as were already mentioned for $R_3$ or $R_4$. Preferred alkyl radicals $R_7$ are methyl, ethyl, propyl and isopropyl.

Inorganic and organic bases are suitable for salt formation, as they are known to one skilled in the art for forming physiologically compatible salts. For example, alkali hydroxides, such as sodium hydroxide and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc., can be mentioned.

To attain the cyclodextrin clathrates, the compounds of formula I are reacted with α-, β- or γ-cyclodextrin. Preferred are β-cyclodextrin derivatives.

Preferred compounds of this invention are compounds of general formula I, whereby the radicals have the following meaning:

$R_1$ is $CH_2OH$, $CONR_5R_6$, $COOR_4$ with $R_4$ in the meaning of a hydrogen atom, an alkyl radical with 1–10 C atoms, a cycloalkyl radical with 5–6 C atoms, a phenal radical optionally substituted by 1–2 chlorine, bromine, phenyl, $C_{1-4}$ alkyl, $C_{1-4}$ alkoxy, chloromethyl, fluoromethyl, trifluoromethyl, carboxy or hydroxy, x is an oxygen atom, y is a methyl group, p is 1–3, o is 1–3, m is 1–3, A is a trans-CH=CH—CH=CH— or a tetramethylene group;

B is a straight-chain or branched-chain saturated or unsaturated alkylene group with up to 10 C atoms, which optionally can be substituted by fluorine or the group $$-\underset{(CH_2)_n}{\overset{|}{C}}-CH_2- \quad \text{or} \quad -CH_2-\underset{(CH_2)_n}{\overset{|}{C}}-$$

with n=2–5,

D is a direct bond, oxygen, sulfur, a —C≡C— group or a —CH=CR$_7$ group with $R_7$ as hydrogen, $C_{1-5}$ alkyl, chlorine or bromine;

B and D together are a direct bond;

$R_2$ means hydrogen or an organic acid radical with 1–15 C atoms;

$R_5$ and $R_6$ have the above-indicated meanings;

$R_3$ is a hydrogen atom, $C_1$–$C_{10}$ alkyl, cycloalkyl with 5–6 C atoms, a phenyl radical optionally substituted by 1–2 chlorine, bromine, phenyl, $C_{1-4}$ alkyl, $C_{1-4}$ alkoxy, chloromethyl, fluoromethyl, trifluoromethyl, carboxy or hydroxy, and if $R_4$ means a hydrogen, their salts with physiologically compatible bases and their cyclodextrin clathrates.

Especially preferred compounds of this invention are compounds of general formula I, whereby the radicals have the following meaning:

$R_1$ is $CH_2OH$, $CONR_5R_6$, $COOR_4$ with $R_4$ in the meaning of a hydrogen atom, an alkyl radical with 1–4 C atoms;

$R_2$ means hydrogen or an organic acid radical with 1–6 C atoms;

$R_3$ is a hydrogen atom or $c_{1-10}$ alkyl;

$R_5$ and $R_6$ have the above-indicated meanings;

A is a trans, trans-CH=CH—CH=CH— or tetramethylene group;

B is a straight-chain or branched-chain alkylene group with up to 5 C atoms, or the group $$-\underset{(CH_2)_n}{\overset{|}{C}}-CH_2- \quad \text{or} \quad -CH_2-\underset{(CH_2)_n}{\overset{|}{C}}-$$

with n=3,4;

D is a direct bond or a —C≡C— group or a —CH=CR$_7$ group with $R_7$ as hydrogen or $C_{1-5}$ alkyl;

x is an oxygen atom, y is a methyl group, p is 1, o is 1, m is 1, 2;

B and D are together a direct bond;

and if $R_4$ means a hydrogen atom, their salts with physiologically compatible bases and their cyclodextrin clathrates.

In addition, the invention relates to a process for the production of the compounds of general formula I according to the invention, which is characterized in that a ketone of formula II, $$\text{(II)}$$

in which A, B, D, $R_2$, $R_3$ and Y have the above-indicated meaning, optionally under protection of free hydroxy groups in $R_2$, is reacted with an olefination reagent of general formula III, $$E-(CH_2)-(CH_2)_o-X-(CH_2)_p-R_1 \quad \text{(III)}$$

whereby E represents a $$Ph_3\overset{(+)}{P}-$$

or $$(C_2H_5O)_2\overset{O}{\underset{\|}{P}}-$$

or $$(CH_3O)_2\overset{O}{\underset{\|}{P}}-$$

radical, and o, X, p, and $R_1$ have the above-indicated meanings, is reacted in the presence of a base and optionally then separated in any sequence of isomers, protected hydroxy groups are released and/or a free hydroxy group is etherified and/or the 1-hydroxy group is oxidized to carboxylic acid and/or reduced and/or a carboxyl group is esterified and/or a free carboxyl group is converted into an amide or a carboxyl group is converted into a salt with a physiologically compatible base.

The reaction of the compound of general formula II with an olefination reagent of general formula III is performed in the presence of a base at temperatures of −80° C. to 100° C., preferably −20° C. to 80° C. in an aprotic solvent or solvent mixture, for example tetrahydrofuran, diethyl ether, dimethyl sulfoxide. As bases, depending on the meaning of radical E, sodium hydride, methylsulfinylmethyl sodium, potassium-tert-butylate, lithium diisopropylamide, 1,5-diazabicyclo[4.3.0]non-5-ene are suitable. The separation of the Z- and E-configured olefines that are obtained in this case is carried out in the usual way, for example by column chromatography.

The reduction to the compounds of formula I with $R_1$ in the meaning of a $CH_2OH$ group is performed with a reducing agent that is suitable for the reduction of esters or carboxylic acids, such as, for example, lithium aluminum hydride, diisobutyl aluminum hydride, etc. As solvents, diethyl ether, tetrahydrofuran, dimethoxyethane, toluene, etc., are suitable. The reduction is performed at temperatures of −30° C. up to boiling temperature of the solvent that is used, preferably 0° C. to 30° C.

The esterification of the alcohols of formula I ($R_2$=H) is carried out in a way that is known in the art. For example, the esterification is carried out in that an acid derivative, preferably an acid halide or acid anhydride, is reacted with an alcohol of formula I in the presence of a base such as, for example, sodium hydride, pyridine, triethylamine, tributylamine or 4-dimethylaminopyridine. The reaction can be performed without a solvent or in an inert solvent, preferably acetone, acetonitrile, dimethylacetamide, dimethyl sulfoxide at temperatures above or below room temperature, for example, between −80° C. to 100° C., preferably at room temperature.

The etherification of the alcohols of formula I ($R_1$=$CH_2OH$) is carried out in a way that is known in the art. For example, the etherification is carried out in that the alcohol of general formula I ($R_1$=$CH_2OH$), optionally under protection of present free hydroxy groups with a halocarboxylic acid derivative or haloalkyl derivative of general formula IV,

$$\text{Hal}-(CH_2)_p-R_1 \quad\quad\quad (IV)$$

whereby Hal is a chlorine, bromine or iodine atom and $R_1$ has the above-indicated meaning, is reacted in the presence of a base, and then optionally $R_1$, as described above, is further functionalized. The reaction of the compound of general formula I with a halogen compound of general formula IV is performed at temperatures of 0° C. to 100° C., preferably 10° C. to 80° C., in an aprotic solvent or solvent mixture, for example dimethyl sulfoxide, dimethylformamide, tetrahydrofuran, toluene, etc. As bases, the bases that are known to one skilled in the art for etherification are suitable, for example sodium hydride, potassium-tert-butylate, butyllithium. The above-mentioned etherification can also be performed preferably under phase-transfer conditions with 20–50% aqueous sodium hydroxide or potassium hydroxide solution without an additional solvent or in an aprotic solvent, such as, for example, toluene in the presence of a phase-transfer catalyst such as tetrabutylammonium hydrogen sulfate at temperatures of between 0° C. and 90° C., preferably between 20° C. and 60° C.

The oxidation of the 1-hydroxy group is performed according to the methods that are known to one skilled in the art. As oxidizing agents, for example, the following can be used: pyridinium dichromate (Tetrahedron Letters, 1979, 399), Jones reagent (J. Chem. Soc. 1953, 2555) or platinum/oxygen (Adv. in Carbohydrate Chem. 17, 169 (1962) or Collins oxidation (Tetrahedron Letters 1968, 3363) and subsequent Jones oxidation. The oxidation with pyridinium dichromate is performed at temperatures of 0° C. to 100° C., preferably at 20° C. to 40° C. in a solvent that is inert with respect to the oxidizing agent, for example dimethylformamide.

The oxidation with Jones reagent is performed at temperatures of −40° C. to +40° C., preferably 20° C. to 30° C. in acetone as a solvent.

The oxidation with platinum/oxygen is performed at temperatures of 0° C. to 60° C., preferably 20° C. to 40° C. in a solvent that is inert with respect to the oxidizing agent, such as, e.g., ethyl acetate.

The saponification of the esters of formula I is performed according to the methods that are known to one skilled in the art, such as, for example, with basic catalysts. The compounds of formula I can be separated by the conventional separating methods into optical isomers (Asymmetric Synthesis, Vol. 1–5, Ed. J. D. Morrison, Academic Press, Inc., Orlando etc., 1985; Chiral Separations by HPLC, Ed. A. M. Krstulovic; John Wiley & Sons; New York etc. 1989).

The release of the functionally modified hydroxy groups is carried out according to known methods. For example, the cleavage of hydroxy protective groups, such as, for example, the tetrahydropyranyl radical, is performed in an aqueous solution of an organic acid, such as, e.g., oxalic acid, acetic acid, propionic acid, i.a., or in an aqueous solution of an inorganic acid, such as, e.g., hydrochloric acid. To improve the solubility, a water-miscible, inert, organic solvent is suitably added. Suitable organic solvents are, e.g., alcohols, such as methanol and ethanol, and ethers, such as dimethoxyethane, dioxane and tetrahydrofuran. Tetrahydrofuran is preferably used. The cleavage is performed preferably at temperatures of between 20° C. and 80° C. The cleavage of the silyl ether protective groups is carried out, for example, with tetrabutylammonium fluoride or with potassium fluoride in the presence of a crown ether (such as, for example, dibenzo[18]-crown-6). As a solvent, for example, tetrahydrofuran, diethyl ether, dioxane, dichloromethane, etc., are suitable. The cleavage is performed preferably at temperatures of between 0° C. and 80° C.

The saponification of the acyl groups is carried out, for example, with alkali or alkaline-earth carbonates or -hydroxides in an alcohol or in the aqueous solution of an alcohol. As an alcohol, lower aliphatic alcohols, such as, e.g., methanol, ethanol, butanol, etc., preferably methanol, are considered. As alkali carbonates and -hydroxides, potassium and sodium salts can be mentioned. Preferred are potassium salts.

As alkaline-earth carbonates and -hydroxides, for example, calcium carbonate, calcium hydroxide and barium carbonate are suitable. The reaction is carried out at −10° C. to +70° C., preferably at +25° C.

The introduction of ester group —$COOR_4$ for $R_1$, in which $R_4$ represents an alkyl group with 1–10 C atoms, is carried out according to the methods that are known to one skilled in the art. The 1-carboxy compounds are reacted, for example, with diazohydrocarbons in a way that is known in the art. The esterification with diazohydrocarbons is carried out, e.g., in that a solution of the diazohydrocarbon in an inert solvent, preferably in diethyl ether, is mixed with the 1-carboxy compound in the same solvent or in another inert solvent, such as, e.g., methylene chloride. After the reaction is completed in 1 to 30 minutes, the solvent is removed, and the ester is purified in the usual way. Diazoalkanes are either known or can be produced according to known methods [Org. Reactions Vol. 8, pages 389–394 (1954)].

The introduction of ester group —$COOR_4$ for $R_1$, in which $R_4$ represents a substituted or unsubstituted aryl group, is carried out according to the methods that are known to one skilled in the art. For example, the 1-carboxy compounds are reacted in an inert solvent with the corresponding arylhydroxy compounds with dicyclohexylcarbodiimide in the presence of a suitable base, for example, pyridine, dimethylaminopyridine, triethylamine. As a solvent, methylene chloride, ethylene chloride, chloroform, ethyl acetate, tetrahydrofuran, preferably chloroform, are suitable. The reaction is performed at temperatures of between −30° C. and +50° C., preferably at 10° C.

If C=C double bonds that are contained in the primary product are to be reduced, the hydrogenation is carried out according to methods that are known in the art.

The hydrogenation of the $\Delta^{8,10}$-diene system is performed in a way that is known in the art at low temperatures, preferably at about −20° C. to +30° C. in a hydrogen atmosphere in the presence of a noble metal catalyst. As a catalyst, for example, 10% palladium on carbon is suitable.

The leukotriene-$B_4$ derivatives of formula I with $R_4$ meaning a hydrogen can be converted into a salt with suitable amounts of the corresponding inorganic bases with neutralization. For example, in dissolving the corresponding acids in water, which contains the stoichiometric amount of the base, the solid inorganic salt is obtained after water is evaporated or after a water-miscible solvent, e.g., alcohol or acetone, is added.

For the production of an amino salt, $LTB_4$-acid is dissolved in, e.g., a suitable solvent, for example, ethanol, acetone, diethyl ether, acetonitrile or benzene, and at least the stoichiometric amount of the amine is added to the solution. In this way, the salt usually accumulates in solid form or is isolated after the solvent is evaporated in the usual way.

The introduction of amide group —$CONHR_5$ with $R_5$ in the meaning of alkanoyl is carried out according to the methods that are known to one skilled in the art. The carboxylic acids of formula I ($R_4$=H) are first converted into the mixed anhydride in the presence of a tertiary amine, such as, for example, triethylamine, with isobutyl chloroformate. The reaction of the mixed anhydride with the alkali salt of the corresponding amide or with ammonia ($R_5$=H) is carried out in an inert solvent or solvent mixture, such as, for example, tetrahydrofuran, dimethoxyethane, dimethylformamide, hexamethylphosphoric acid triamide, at temperatures of between −30° C. and +60° C., preferably at 0° C. to 30° C. Another type of production of the amides involves the amidolysis of 1-ester ($R_1$=$COOR_4$) with the corresponding amine.

Another possibility for the introduction of amide group —$CONHR_5$ consists in the reaction of a 1-carboxylic acid of formula I ($R_4$=H), in which free hydroxy groups are optionally intermediately protected, with compounds of formula IV, $$O=C=N-R_5 \tag{IV}$$

in which $R_5$ has the above-indicated meaning.

The reaction of the compound of formula I ($R_4$=H) with an isocyanate of formula IV is carried out optionally with the addition of a tertiary amine, such as, e.g., triethylamine or pyridine. The reaction can be performed without a solvent or in an inert solvent, preferably acetonitrile, tetrahydrofuran, acetone, dimethylacetamide, methylene chloride, diethyl ether, toluene, at temperatures of between −80° C. to 100° C., preferably at 0° C. to 30° C.

For the production of the other amides, for example, the desired acid anhydride can be reacted with ammonia or the corresponding amines.

If the starting product contains OH groups in the leukotriene-$B_4$ radical, these OH groups are also brought to reaction. If end products that contain free hydroxyl groups are ultimately desired, a start is suitably made from starting products in which the latter are intermediately protected by preferably readily cleavable ether or acyl radicals.

The separation of the diastereomers is carried out according to the methods that are known to one skilled in the art, for example by column chromatography.

The compounds of general formula II that are used as starting material can be produced, for example, by an ester of general formula V ((a) K. Sakai et al., Tetrahedron 50, 3315 (1995); b) K. Koga et al., Tetrahedron 49, 1579 (1993)),

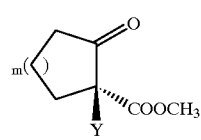

(V)

in which m and Y have the above-indicated meanings, being ketalized with ethylene glycol, reduced with diisobutylaluminum hydride and then oxidized to the aldehyde of general formula VI with the Collins reagent or by the Swern process (Tetrahedron Letters 34, 1651 (1978)) in a way that is known in the art.

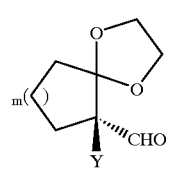

(VI)

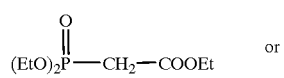

or (VII)

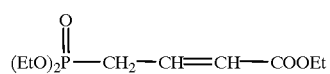

(VIII)

The Wittig-Horner olefination of aldehyde VI with the phosphonate of formula VII and a base and optionally subsequent hydrogenation as well as subsequent reduction of the ester group, oxidation of the primary alcohol, repeated Wittig-Horner olefination with the phosphonate of formula VII and optionally subsequent hydrogenation or a Wittig-Horner reaction of aldehyde VI with a phosphonate of formula VIII provides the esters of general formula IX, whereby

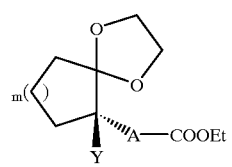

(IX)

m, y and A have the above-indicated meanings. As bases, for example, potassium-tert-butylate, diazabicyclononane, diazabicycloundecane or sodium hydride are suitable. Reduction of the ester group, for example with diisobutyl aluminum hydride, and subsequent oxidation of the primary alcohol that is obtained, e.g., with manganese dioxide or Collins reagent, results in an aldehyde of formula X.

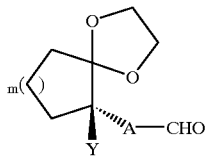

(X)

The organometallic reaction of the aldehyde of formula X with a Grignard reagent of formula XI, in which B, D

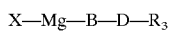

(XI)

and $R_3$ have the above-indicated meanings and X means chlorine, bromine or iodine, results, under protection of the hydroxy groups (for example by acylation) and optionally diastereomer separation, in the compounds of formula XII.

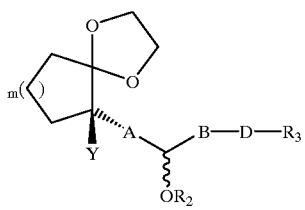

(XII)

The production of the compound of formula XI that is required for the organometallic reaction is carried out by reaction of the corresponding terminal halide with magnesium. By reaction of ketal XII with dilute acetic acid and optionally saponification of the ester and subsequent silylether formation, the ketone of formula XIII is obtained.

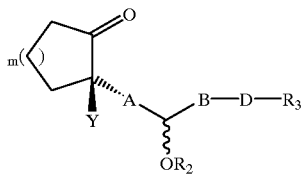

(XIII)

The compounds of formula XII, in which B means a $CH_2$ group and D means a —C≡C— group or a CH=$CR_7$ group, can be obtained, for example, by an organometallic reaction of a propargyl halide and subsequent alkylation with a corresponding alkyl halide and optionally subsequent Lindlar hydrogenation.

An alternative structure of the lower chain starts from the aldehyde of formula XIV, which resulted from the Wittig-Horner reaction of aldehyde VI and subsequent reduction and oxidation.

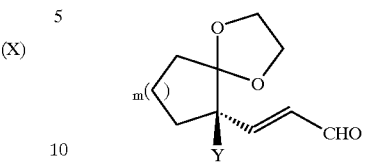

(XIV)

Wittig-Horner olefination of aldehyde XIV with a phosphonate of formula XV

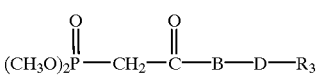

(XV)

and reduction of the ketone that is produced then resulted in an alcohol of formula XII, which optionally can be separated into diastereomers. The protection of the hydroxy group that is now added, for example by acylation, ketal cleavage with acetic acid, optionally saponification of the ester and silylether formation results in the ketone of formula XIII.

The production of the phosphonates of general formula XV that are required for this reaction is described in, for example, DE 42 42 390 or is carried out in a way that is known in the art by reaction of an alkyl halide (that can be produced from the corresponding alcohol by halogenation) of general formula XVI

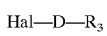

(XVI)

with the dianion that is produced from the phosphonate of general formula XVII

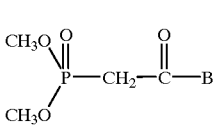

(XVII)

in which B, D and $R_3$ have the above-indicated meanings.

An alternative access to the phosphonates of general formula XV consists in the reaction of the anion of methylphosphonic acid dimethyl ester with an ester of general formula XVIII,

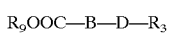

(XVIII)

in which $R_3$, B, and D have the above-indicated meanings and $R_9$ means an alkyl group with 1–5 C atoms. These esters can be obtained by, for example, alkylation with the corresponding halide.

The incorporation of the chemically and metabolically labile cis-$\Delta^{6,7}$ double bond of $LTB_4$ into a cis-1,2-substituted cycloalkyl ring results in a stabilization, whereby especially by further derivatization of the functional groups and/or structural changes of the lower side chain, $LTB_4$ derivatives that can act as $LTB_4$ antagonists were obtained (DE-A 39 17 597 and DE-A 42 27 790.6 and DE-A 41 08 351 and DE-A 41 39 886.8 and DE-A 42 42 390).

It has now been found that by introducing an alkyl group into the 7-position and by introducing a double bond into 5,6-position (numbering system beginning with a carboxyl-C atom with 1 when $LTB_4$ nomenclature is used)

in such leukotriene-$B_4$ derivatives, a prolonged duration of action, greater selectivity and better effectiveness can be achieved.

The compounds of formula I act in an antiinflammatory, antiallergic and antiproliferative manner. In addition, the compounds are suitable for lowering elevated triglyceride levels. In addition, they have antimycotic properties. Consequently, the new leukotriene-$B_4$ derivatives of formula I represent valuable pharmaceutical active ingredients. The compounds of formula I are suitable for topical and oral administration.

The new leukotriene-$B_4$ derivatives of formula I are suitable in combination with the additives and vehicles that are commonly used in galenical pharmaceutics for topical treatment of diseases of the skin, in which leukotrienes play an important role, e.g.: contact dermatitis, eczemas of the most varied types, neurodermatoses, erythrodermia, pruritus vulvae et ani, rosacea, cutaneus lupus erythematosus, psoriasis, lichen ruber planus et verrucosis and similar skin diseases.

In addition, the new leukotriene-$B_4$ antagonists are suitable for the treatment of multiple sclerosis and symptoms of shock.

The production of the pharmaceutical agent specialties is carried out in the usual way by the active ingredients being converted with suitable additives into the desired form of administration, such as, for example: solutions, ointments, creams or patches.

In the thus formulated pharmaceutical agents, the active ingredient concentration depends on the form of administration. In lotions and ointments, an active ingredient concentration of 0.0001% to 3% is preferably used.

Further, the new compounds optionally in combination with commonly used vehicles and adjuvants are also well-suited for the production of inhalants, which can be used to treat allergic diseases of the respiratory system, such as, for example, bronchial asthma or rhinitis.

Further, the new leukotriene-$B_4$ derivatives are also suitable in the form of capsules, tablets or coated tablets, which preferably contain 0.1 to 100 mg of active ingredient and are administered orally or in the form of suspensions, which preferably contain 1–200 mg of active ingredient per dosage unit, and are also administered rectally to treat diseases of the internal organs, in which leukotrienes play an important role, such as, e.g.: allergic diseases of the intestinal tract, such as colitis ulcerosa and colitis granulomatosa.

In these new forms of administration, the new $LTB_4$ derivatives, in addition to the treatment of diseases of internal organs with inflammatory processes, are also suitable for the treatment of diseases in which, leukotriene-dependent, the increased growth and the new formation of cells are important. Examples are leukemia (increased growth of white blood cells) or arteriosclerosis (increased growth of smooth muscle cells of blood vessels).

The new leukotriene-$B_4$ derivatives can also be used in combination with, e.g., lipoxygenase inhibitors, cyclooxygenase inhibitors, glucocorticoids, prostacyclin agonists, thromboxane antagonists, leukotriene-$D_4$ antagonists, leukotriene-$E_4$ antagonists, leukotriene-$F_4$ antagonists, phosphodiesterase inhibitors, calcium antagonists, PAF antagonists or other known forms of treatment of the respective diseases.

The following embodiments are used for a more detailed explanation of the process according to the invention. In the examples, diastereomers in 12-position that are not characterized in more detail were characterized as polar or nonpolar (e.g., diastereomer unpol [nonpol] (12)).

EXAMPLE 1

5-{(E)-(2S)-2-((1E,3E)-(5S)-5-Hydroxy-6,6-trimethylene-9-phenyl-1,3-nonadien-8-inyl)-2-methyl-cyclohexylidene}-3-oxa-pentanoic acid-tert-butyl ester A solution of 2.5 ml of phosphonoacetic acid triethyl ester in 7 ml of ethylene glycol dimethyl ether is added in drops at 0° C. under nitrogen to a suspension of 501 mg of sodium hydride (60% in mineral oil) in 7 ml of ethylene glycol dimethyl ether, and it is stirred for 2 more hours. A solution of 3 g of the ketone, produced according to Example 1d), in 9 ml of ethylene glycol dimethyl ether is now added in drops to the reaction mixture and stirred for 18 hours at 50° C. Then, saturated ammonium chloride solution is added and extracted with ether. The combined organic phases are washed with water and saturated sodium chloride solution, dried on sodium sulfate, and after filtration, it is concentrated by evaporation in a vacuum. The residue that is thus obtained is purified by chromatography on silica gel. With hexane/0–10% ether, 2.9 g of the α,β-unsaturated ester is obtained as a colorless oil.

IR (Film): 2931, 2840, 1716, 1472, 1252, 1174, 994, 836 $cm^{-1}$ 9.7 ml of diisobutylaluminum hydride (20% in toluene) is added in drops at −70° C. under nitrogen to a solution of 2.9 g of the above-described ester in 35 ml of toluene, and it is stirred for 30 more minutes. Then, 3 ml of isopropanol is carefully added in drops and stirred for 10 minutes. It is now mixed with water, stirred for 2 hours at room temperature, the white precipitate is filtered off and washed thoroughly with ethyl acetate. The filtrate is concentrated by evaporation in a vacuum. The residue that is thus obtained is purified by chromatography on silica gel. With hexane/0–30% ether, 2.1 g of the allyl alcohol is obtained as a colorless oil.

IR (Film): 3317, 2928, 2840, 2222, 1665, 1598, 1490, 1462, 1360, 1254, 1100, 1057, 993, 835, 775, 754, 691, 525 $cm^{-1}$ 3.36 ml of bromoacetic acid-tert-butyl ester, followed by 14 ml of 25% sodium hydroxide solution and 98.8 mg of tetrabutylammonium hydrogen sulfate, are added to a solution of 2.1 g of the above-described alcohol in 22 ml of toluene. It is now stirred for 16 hours under nitrogen at room temperature. Then, it is diluted with ether, washed with water and saturated sodium chloride solution, the organic phase is dried on sodium sulfate, and after filtration, it is concentrated by evaporation in a vacuum. The residue that is thus obtained is purified by chromatography on silica gel. With hexane/0–20% ether, 2.3 g of the ester is obtained as a colorless oil.

IR (Film): 2928, 2840, 1748, 1651, 1598, 1490, 1462, 1392, 1368, 1252, 1223, 1124, 1061, 994, 940, 836, 775, 755, 691 $cm^{-1}$ 770 mg of tetrabutylammonium fluoride×3 $H_2O$ is added at room temperature under nitrogen to a solution of 755 mg of the above-described ester in 5 ml of tetrahydrofuran, and it is stirred for 6 more hours. Then, it is diluted with ether, washed with water, the organic phase is dried on sodium sulfate, and after filtration, it is concentrated by evaporation in a vacuum. The residue that is thus obtained is purified by chromatography on silica gel. With hexane/0–60% ether, 556 mg of the title compound is obtained as a colorless oil.

IR (Film): 3478, 2928, 2840, 1747, 1650, 1598, 1490, 1442, 1368, 1225, 1122, 994, 943, 845, 756, 693, 526, 466 $cm^{-1}$ The starting material for the above title compound is produced as follows:

1a) (2S)-1-Ethylenedioxy-2-hydroxymethyl-2-methyl-cyclohexane 4.2 g of ethylene glycol, followed by 60 mg of p-toluenesulfonic acid, is added to a solution of 3.1 g of (2R)-2-methyl-2-methoxycarbonyl-1-oxo-cyclohexane ((a) K. Sakai et al., Tetrahedron 50, 3315 (1994); b) K. Koga et al., Tetrahedron 49, 1579 (1993)) in 20 ml of toluene, and the mixture is refluxed for 5 hours with a water separator. Then, it is diluted with ether, washed with saturated sodium bicarbonate solution and water, dried on sodium sulfate, and after filtration, it is concentrated by evaporation in a vacuum. The residue that is thus obtained is purified by chromatography on silica gel. With hexane/ether (8:2), 3.8 g of the ethylene ketal is obtained as a colorless oil.

IR(CHCl$_3$): 2980, 2930, 2885, 1718, 1460, 950 cm$^{-1}$ 218 ml of diisobutylaluminum hydride (20% in toluene) is added in drops at −30° C. under nitrogen to a solution of 22.5 g of the ethylene ketal in 200 ml of toluene, and it is stirred for 1 more hour. Then, it is cooled to −70° C. and mixed drop by drop with 100 ml of isopropanol. 109 ml of water is now carefully added in drops to the reaction mixture, the cold bath is removed after 30 minutes, and vigorously stirred for 2 hours. The precipitate is suctioned off, washed thoroughly with ethyl acetate, and the filtrate is concentrated by evaporation in a vacuum. The residue that is thus obtained is purified by chromatography on silica gel. With hexane/0–60% ether, 19.5 g of the title compound is obtained as a colorless oil.

IR (Film): 3452, 2940, 2640, 1464, 1414, 1333, 1276, 1178, 1092, 1031, 949, 877, 799, 745 cm$^{-1}$ 1b) 3-{(2S)-1,1-Ethylenedioxy-2-methyl-cyclohex-2-yl}-(2E)-propen-1-al A solution of 47.3 g of dimethyl sulfoxide in 160 ml of methylene chloride is carefully added in drops at −70° C. to −65° C. under nitrogen to a solution of 35.8 g of oxalyl chloride in 210 ml of methylene chloride, and it is stirred for 10 minutes. A solution of 38.9 g of the alcohol, produced under Example 1a), in 160 ml of methylene chloride is now added to this reaction mixture, and it is stirred for 2 more hours at −70° C. Then, 63.4 g of triethylamine is added in drops, stirred for 1 hour, and the reaction mixture is added to water. It is now extracted with methylene chloride, the combined organic phases are washed with 5% sulfuric acid, saturated sodium bicarbonate solution and with saturated sodium chloride solution, dried on sodium sulfate, and after filtration, it is concentrated by evaporation in a vacuum. 38.4 g of the aldehyde is obtained as a colorless oil without further purification.

IR (Film): 2938, 1723, 1449, 1391, 1352, 1276, 1215, 1183, 1092, 1067, 1041, 1019, 949, 881, 789, 752 cm$^{-1}$ 65.4 g of phosphonoacetic acid triethyl ester, followed by 39.7 g of 1,8-diazabicyclo[5.4.0]undec-7-ene, are added in drops at room temperature under nitrogen to 12.8 g of lithium chloride in 310 ml of acetonitrile, and it is stirred for 20 more minutes. Then, 38.4 g of the above-described aldehyde in 75 ml of acetonitrile is added in drops to the reaction mixture and stirred for 4.5 hours. About ⅔ of the solvent is now carefully distilled off in a vacuum, the residue is added to water, extracted with ether, the combined organic phases are washed with semiconcentrated sodium chloride solution, dried on sodium sulfate, and after filtration, it is concentrated by evaporation in a vacuum. The residue that is thus obtained is purified by chromatography on silica gel. With hexane/0–30% ether, 42.2 g of the ester is obtained as a colorless oil.

IR (Film): 2937, 2860, 1719, 1648, 1447, 1367, 1311, 1271, 1181, 1090, 1037, 950, 868 cm$^{-1}$ 304 ml of diisobutylaluminum hydride (20% in toluene) is added in drops at −70° C. under nitrogen to a solution of 42.2 g of the above-described ester in 360 ml of toluene, and it is stirred for 45 more minutes. Then, 120 ml of isopropanol is slowly added in drops, followed by 150 ml of water, and it is stirred vigorously for 2 hours. The precipitate is suctioned off, washed thoroughly with ethyl acetate, and the filtrate is concentrated by evaporation in a vacuum. The residue that is thus obtained is purified by chromatography on silica gel. With hexane/0–60% ether, 33 g of the alcohol is obtained as a colorless oil.

IR (Film): 3416, 2934, 2865, 1447, 1372, 1180, 1126, 1091, 1023, 960, 880 cm$^{-1}$ 108 g of manganese(IV) oxide is added in portions to a solution of 33 g of the above-described alcohol, in 450 ml of toluene, and it is stirred for 4.5 hours at room temperature under nitrogen. Then, it is suctioned off on Celite, rewashed with ethyl acetate, and the filtrate is concentrated by evaporation in a vacuum. 31.4 g of the title compound is obtained as a pale yellow-colored oil without further purification.

IR (Film): 2937, 2866, 2728, 1690, 1631, 1462, 1374, 1275, 1181, 1130, 1090, 1022, 962, 881, 797, 733, 595 cm$^{-1}$ 1c) (5S)-5-Acetoxy-1-{(2S)-1,1-ethylenedioxy-2-methyl-cyclohexyl-2-yl}-6,6-trimethylene-9-phenyl-(1E,3E)-1,3-nonadien-8-ine A solution of 55 g of 2-oxo-3,3-trimethylene-6-phenyl-hex-5-ine-phosphonic acid dimethyl ester in 250 ml of ethylene glycol dimethyl ether is added in drops at 0° C. under nitrogen to a suspension of 6.8 g of sodium hydride (65% in mineral oil) in 200 ml of ethylene glycol dimethyl ether, and it is stirred for 1 more hour. A solution of 31.4 g of the aldehyde, produced in Example 1b), in 250 ml of ethylene glycol dimethyl ether is now added in drops, stirred for 30 minutes at 0° C., and for 20 hours at room temperature. Then, saturated ammonium chloride solution is added, extracted with ether, and the combined organic phases are washed with concentrated sodium chloride solution. It is dried on sodium sulfate and after filtration, it is concentrated by evaporation in a vacuum. The residue that is thus obtained is purified by chromatography on silica gel. With hexane/0–30% ether, 56 g of the ketone is obtained as a colorless oil.

IR (Film): 2934, 2880, 1680, 1625, 1592, 1490, 1442, 1343, 1180, 1137, 1088, 1010, 962, 880, 756, 692, 527 cm$^{-1}$ A solution of 56 g of the above-described ketone in 650 ml of methylene chloride and 300 ml of tetrahydrofuran is mixed at −60° C. under nitrogen with 7.7 g of cerium trichloride heptahydrate, and it is stirred for 30 minutes at this temperature. 7.8 g of sodium borohydride is now added and stirred for 1 more hour. Then, 100 ml of acetone is added in drops, stirred for 30 minutes, the pH is set at 7 with glacial acetic acid and concentrated by evaporation in a vacuum at 30° C. The residue is diluted with water/ether 1:1, extracted with ether, and the combined organic phases are washed with semiconcentrated sodium chloride solution. It is dried on sodium sulfate and after filtration, it is concentrated by evaporation in a vacuum. The residue that is thus obtained is separated by repeated chromatography on silica gel. With hexane/0–40% ether, first 23.8 g of the nonpolar β-configured alcohol (5S)-5-hydroxy-1-{(2S)-1,1-ethylenedioxy-2-methyl-cyclohexyl-2-yl}-6,6-trimethylene-9-phenyl-(1E,3E)-1,3-nonadien-8-ine is obtained as a colorless oil, and 26 g of the polar α-configured alcohol (5R)-5-hydroxy-1-{(2S)-1,1-ethylenedioxy-2-methyl-cyclohexyl-2-yl}-6,6- trimethylene-9-phenyl-(1E,3E)-1,3-nonadien-8-ine is obtained as a colorless oil.

IR (Film): (Nonpolar alcohol) 2463, 2933, 2830, 1598, 1490, 1442, 1180, 1089, 994, 950, 880, 756, 692, 526 cm$^{-1}$ 30 ml of acetic acid anhydride is added to a solution of 23.3 g of the above-produced nonpolar alcohol in 60 ml of pyridine, and it is stirred under nitrogen for 16 hours at room temperature. Then, it is concentrated by evaporation several times in a vacuum with the addition of toluene. The residue that is thus obtained is purified by chromatography on silica gel. With hexane/0–30% ether, 23.95 g of the title compound is obtained as a colorless oil.

IR (Film): 2934, 2880, 1732, 1653, 1598, 1490, 1442, 1370, 1236, 1180, 1090, 1020, 995, 962, 880, 797, 757, 692, 526 cm$^{-1}$ 1d) (5S)-5-Tert-butyldimethylsilyloxy-1-{(2S)-1-oxo-2-methyl-cyclohexyl-2-yl}-6,6-trimethylene-9-phenyl-(1E,3E)-1,3-nonadien-8-ine 21 g of the acetate that is produced under Example 1c) is dissolved in 64 ml of tetrahydrofuran and 500 ml of a mixture (65:35:10/acetic acid:water:tetrahydrofuran), and it is stirred under nitrogen at 45° C. for 3.5 hours. Then, the reaction mixture is cooled in an ice bath, brought to pH 8 carefully with 600 ml of ice-cold 8 molar sodium hydroxide solution and stirred for 30 more minutes. It is now extracted with ether, the combined organic phases are washed with saturated sodium chloride solution, dried on sodium sulfate and after filtration, it is concentrated by evaporation in a vacuum. The residue that is thus obtained is purified by chromatography on silica gel. With hexane/0–20% ether, 15.4 g of the ketone is obtained as a colorless oil.

IR (Film): 2934, 2880, 1735, 1708, 1490, 1442, 1371, 1235, 1118, 992, 757, 692 cm$^{-1}$ 5.7 g of potassium carbonate is added to a solution of 8.3 g of the above-described ketone in 350 ml of methylene chloride, and it is stirred under nitrogen at room temperature for 16 hours. Then, it is diluted with ether, washed with water and saturated sodium chloride solution, the organic phase is dried on sodium sulfate and after filtration, it is concentrated by evaporation in a vacuum. The residue that is thus obtained is purified by chromatography on silica gel. With hexane/0–40% ether, 7.4 g of the alcohol is obtained as a colorless oil.

IR (Film): 3478, 2933, 2862, 2362, 1704, 1598, 1570, 1490, 1443, 1372, 1242, 1090, 1045, 992, 911, 860, 802, 757, 692, 526 cm$^{-1}$ 5.6 g of imidazole, followed by 6.2 g of tert-butyldimethylsilyl chloride, are added at 0° C. under nitrogen to a solution of 7.4 g of the above-described alcohol in 60 ml of N,N-dimethylformamide, and it is stirred for 15 minutes at 0° C. and for 16 hours at room temperature. Then, it is diluted with ether, and washed with water, 5% sulfuric acid, water, saturated sodium bicarbonate solution and saturated sodium chloride solution. The organic phase is dried on sodium sulfate and after filtration, it is concentrated by evaporation in a vacuum. The residue that is thus obtained is purified by chromatography on silica gel. With hexane/0–20% ether, 9.3 g of the title compound is obtained as a colorless oil.

IR (Film): 2930, 2856, 2220, 1710, 1653, 1598, 1489, 1442, 1360, 1254, 1102, 1062, 991, 836, 776, 756, 691, 523 cm$^{-1}$

EXAMPLE 2

5-{(E)-(2S)-2-((1E,3E)-(5S)-5-Hydroxy-6,6-trimethylene-9-phenyl-1,3-nonadien-8-inyl)-2-methyl-cyclohexyliden}-3-oxa-pentanoic acid 5.6 ml of 0.5 molar lithium hydroxide solution, followed by 78 mg of lithium hydroxide, are added to a solution of 546 mg of 5-{(E)-(2S)-2-((1E,3E)-(5S)-5-Hydroxy-6,6-trimethylene-9-phenyl-1,3-nonadien-8-inyl)-2-methyl-cyclohexyliden}-3-oxa-pentanoic acid-tert-butyl ester (produced in Example 1) in 5.6 ml of tetrahydrofuran and 5.6 ml of methanol, and it is stirred for 18 hours at room temperature. Then, it is diluted with water, acidified to pH 5 with 1 molar hydrochloric acid, extracted with ethyl acetate, dried on sodium sulfate and after filtration, it is concentrated by evaporation in a vacuum. The residue that is thus obtained is purified by chromatography on silica gel. With hexane/0–70% ethyl acetate, 9.3 g of the title compound is obtained as a colorless oil. This substance is the preferred embodiment. IR (Film): 3440, 2915, 2860, 1740, 1655, 1600, 1490, 1440, 1370, 1240, 1110, 990, 755, 690, 530 cm$^{-1}$

EXAMPLE 3

5-{(E)-(2S)-2-((1E,3E)-(5R)-5-Hydroxy-7,7-trimethylene-10-phenyl-1,3-decadien-9-inyl)-2-methyl-cyclohexylidene}-3-oxa-pentanoic acid-tert-butyl ester A solution of 2.7 g of phosphonoacetic acid triethyl ester in 12 ml of ethylene glycol dimethyl ester is added in drops at 0° C. under nitrogen to a suspension of 488 mg of sodium hydride (60% in mineral oil) in 12 ml of ethylene glycol dimethyl ether, and it is stirred for 1 more hour. A solution of 3 g of the ketone, produced according to Example 3c), in 12 ml of ethylene glycol dimethyl ether is now added in drops to the reaction mixture and stirred for 24 hours at 50° C. Then, saturated ammonium chloride solution is added and extracted with ether. The combined organic phases are washed with semi-saturated sodium chloride solution, dried on sodium sulfate and after filtration, it is concentrated by evaporation in a vacuum. The residue that is thus obtained is purified by chromatography on silica gel. With hexane/0–10% ether, 3.4 g of the ester is obtained as a colorless oil.

IR (Film): 2930, 2860, 1720, 1640, 1490, 1480, 1470, 1460, 1380, 1250, 1180, 1130, 1070, 1040, 990, 940, 840, 780, 755, 690, 530 cm$^{-1}$ 11.1 ml of diisobutylaluminimum hydride (20% in toluene) is added in drops at −70° C. under nitrogen to a solution of 3.5 g of the above-described ester in 37 ml of toluene, and it is stirred for 30 more minutes. Then, 3.7 ml of isopropanol is carefully added in drops and stirred for 5 minutes. It is now mixed with water, stirred for 2 hours at room temperature, the white precipitate is filtered off and washed thoroughly with ethyl acetate. The filtrate is concentrated by evaporation in a vacuum. The residue that is thus obtained is purified by chromatography on silica gel. With hexane/0–70% ether, 3 g of the allyl alcohol is obtained as a colorless oil.

IR (Film): 3330, 2928, 2855, 1656, 1598, 1490, 1462, 1442, 1360, 1254, 1070, 993, 836, 809, 775, 755, 691 cm$^{-1}$ 4.9 g of bromoacetic acid-tert-butylester, followed by 15 ml of 25% sodium hydroxide solution and 119 mg of tetrabutylammonium hydrogen sulfate, are added to a solution of 2.6 g of the above-described alcohol, in 24.6 ml of toluene. It is now stirred for 24 hours under nitrogen at room temperature. Then, it is diluted with ether, washed with semi-saturated sodium chloride solution, the organic phase is dried on sodium sulfate and after filtration, it is concentrated by evaporation in a vacuum. The residue that is thus obtained is purified by chromatography on silica gel. With hexane/0–30% ether, 3.8 g of the ether is obtained as a colorless oil.

IR (Film): 2929, 2860, 1749, 1368, 1297, 1256, 1124, 994, 836, 775, 756 cm$^{-1}$ 9.7 g of tetrabutylammonium fluoride×3 H$_2$O is added at room temperature under nitrogen to a solution of 3.8 mg of the above-described ether, in 155 ml of tetrahydrofuran, and it is stirred for 4 more hours. Then, it is diluted with ether, washed with semi-saturated sodium chloride solution, the organic phase is dried on sodium sulfate and after filtration, it is concentrated by evaporation in a vacuum. The residue that is thus obtained is purified by chromatography on silica gel. With hexane/0–70% ether, 2.3 g of the title compound is obtained as a colorless oil.

IR (Film): 3460, 2980, 2940, 2860, 1750, 1650, 1600, 1490, 1440, 1390, 1370, 1300, 1230, 1160, 1120, 990, 940, 850, 760, 690, 590, 530 cm$^{-1}$ The starting material for the above title compound is produced as follows:

3a) 2-Oxo-4,4-trimethylene-7-phenyl-hept-6-ine-phosphonic acid dimethyl ester 412 ml of diisobutylaluminum hydride (20% in toluene) is added in drops at –70° C. under nitrogen to a solution of 56.45 g of 3,3-trimethylene-6-phenyl-5-inoic acid methyl ester (described in German Laid-Open Specification DE 4242390 Al) in 420 ml of toluene, and it is stirred for 40 more minutes. Then, 105 ml of isopropanol is carefully added in drops and stirred for 10 minutes. It is now mixed with water, stirred for 2 hours at room temperature, the white precipitate is filtered off and washed thoroughly with ethyl acetate. The filtrate is concentrated by evaporation in a vacuum. The residue that is thus obtained is purified by chromatography on silica gel. With hexane/0–50% ether, 97.2 g of the alcohol is obtained as a colorless oil.

120.2 g of p-toluenesulfonic acid chloride is added at 0° C. under nitrogen to a solution of 97.2 g of the above-described alcohol in 247 ml of pyridine, stirred for 4 more hours and allowed to stand for 18 hours at about 4° C. Then, it is mixed with ice water and stirred for 2 hours at room temperature. It is now diluted with ether, washed with water, 10% sulfuric acid, water, saturated sodium bicarbonate solution and with saturated sodium chloride solution. The organic phase is dried on sodium sulfate and after filtration, it is concentrated by evaporation in a vacuum. Without further purification, 172 g of the tosylate is obtained as a colorless oil.

IR (Film): 3020, 2980, 2960, 1600, 1490, 1360, 1110, 1175, 1100, 960, 840, 810, 690, 660 cm$^{-1}$ 28.5 g of sodium cyanide is added to a solution of 172 g of the above-described tosylate in 922 ml of dimethyl sulfoxide, and it is stirred for 2.5 hours at 80° C. After cooling, it is poured on ice water, extracted with ether, the combined organic phases are washed with water, dried on sodium sulfate and after filtration, it is concentrated by evaporation in a vacuum. The residue that is thus obtained is purified by chromatography on silica gel. With hexane/0–50% ether, 91.6 g of the nitrile is obtained as a colorless oil.

547 ml of diisobutylaluminum hydride (20% in toluene) is added at –70° C. under nitrogen to a solution of 91.6 g of the above-described nitrile in 650 ml of toluene, and it is stirred for 30 more minutes. Then, 55 ml of toluene is carefully added in drops and stirred for 10 minutes. It is now mixed with saturated ammonium chloride solution, stirred for 6 hours at room temperature, the white precipitate is filtered off and washed thoroughly with ethyl acetate. The filtrate is concentrated by evaporation in a vacuum. Without further purification, 107 g of the aldehyde is obtained as a colorless oil.

IR (Film): 2980, 2940, 2740, 1720, 1600, 1490, 1445, 1180, 1070, 915, 690 cm$^{-1}$ 141.5 ml of Jones reagent is added in drops at –5° C. to a solution of 53.5 g of the above-described aldehyde in 594 ml of acetone, and it is stirred vigorously for 1 more hour. Then, 240 ml of isopropanol is added and stirred for 30 minutes at room temperature. It is now suctioned off on Celite and rewashed with ether. The filtrate is washed with semi-saturated sodium chloride solution, dried on sodium sulfate, and after filtration, it is concentrated by evaporation in a vacuum. The residue that is thus obtained is purified by chromatography on silica gel. With hexane/0–50% ether, 60 g of the acid is obtained as a colorless oil. 96.7 g of potassium carbonate, followed by 43.3 ml of methyl iodide, are added to a solution of 71 g of the above-described acid in 437 ml of acetone, and it is stirred for 20 hours at room temperature. Then, it is suctioned off on Celite, rewashed with ethyl acetate, and concentrated by evaporation in a vacuum. The residue is diluted with ether, washed with water and saturated sodium chloride solution, dried on sodium sulfate and after filtration, it is concentrated by evaporation in a vacuum. The residue that is thus obtained is purified by chromatography on silica gel. With hexane/0–30% ether, 54.3 g of the ester is obtained as a colorless oil.

19.6 ml of methanephosphonic acid dimethyl ester is dissolved in 243 ml of tetrahydrofuran at –70° C., mixed drop by drop with n-butyllithium and stirred for 1 more hour. A solution of 18 g of the above-described esters in 44 ml of tetrahydrofuran is now added in drops to the reaction mixture, and it is stirred for 5 more hours. Then, 13.3 ml of acetic acid is added, and the reaction mixture is allowed to stand overnight at about 6° C. After concentration by evaporation in a vacuum, it is mixed with water, extracted with methylene chloride, the organic phase is dried on sodium sulfate and after filtration, it is concentrated by evaporation in a vacuum. The residue that is thus obtained is purified by chromatography on silica gel. With hexane/0–100% ethyl acetate, 17.9 g of the phosphonate is obtained as a colorless oil.

3b) (5R)-5-Benzoyloxy-1-{(2S)-1,1-ethylenedioxy-2-methyl-cyclohexyl-2-yl}-7,7-trimethylene-10-phenyl-(1E, 3E)-1,3-decadien-9-ine A solution of 17.88 g of the above-described phosphonate in 98 ml of ethylene glycol dimethyl ether is added in drops at 0° C. under nitrogen to a suspension of 2.1 g of sodium hydride (60% in mineral oil) in 65 ml of ethylene glycol dimethyl ether, and it is stirred for 1 more hour. A solution of 9.78 g of the aldehyde, described in 1b), in 98 ml of ethylene glycol dimethyl ether is now added in drops to the reaction mixture, stirred for 30 minutes at 0° C. and for 20 hours at room temperature. Then, saturated ammonium chloride solution is added and extracted with ether. The combined organic phases are washed with semi-saturated sodium chloride solution, dried on sodium sulfate and after filtration, it is concentrated by evaporation in a vacuum. The residue that is thus obtained is purified by chromatography on silica gel. With hexane/0–40% ether, 17.4 g of the ketone is obtained as a colorless oil.

IR (Film): 2940, 2860, 1680, 1655, 1630, 1590, 1490, 1440, 1355, 1180, 1090, 950, 880, 755, 690, 525 cm$^{-1}$ 2.3 g of cerium trichloride heptahydrate is added at –70° C. under nitrogen to a solution of 17.4 g of the above-described ketone in 330 ml of methanol and 33 ml of tetrahydrofuran, and it is stirred for 30 more minutes. 2.4 g of sodium borohydride is now added, and it is stirred for 1 more hour. Then, 20 ml of acetone is added, stirred for 15 minutes at room temperature, the pH is set at 7 with glacial acetic acid, and it is concentrated by evaporation in a vacuum at 30° C. The residue is diluted with water/ether 1:1, extracted with ether, and the combined organic phases are washed with water and saturated sodium chloride solution. It is dried on sodium sulfate and after filtration, it is concentrated by evaporation in a vacuum. The residue that is thus obtained is separated by repeated chromatography on silica gel. With hexane/0–40% ether mixtures, first 7.5 g of the nonpolar β-configured alcohol (5R)-5-hydroxy-1-{(2S)-1,1-ethylenedioxy-2-methyl-cyclohexyl-2-yl}-7,7-trimethylene-10-phenyl-(1E,3E)-1,3-decadien-9-ine and 8.2 g of the polar, α-configured alcohol (5S)-5-hydroxy-1-{(2S)-1,1-ethylenedioxy-2-methyl-cyclohexyl-2-yl}-7,7-trimethylene-10-phenyl-(1E,3E)-1,3-decadien-9-ine are obtained as a colorless oil.

IR (Film): (nonpolar alcohol) 3460, 2940, 2865, 1600, 1490, 1440, 1275, 1180, 1090, 995, 950, 880, 760, 695, 530 cm$^{-1}$ IR (Film): (polar alcohol) 3450, 2940, 2860, 1600, 1480, 1440, 1275, 1180, 1090, 995, 880, 760, 695, 530 cm$^{-1}$ 4.2 ml of benzoyl chloride is added at 0° C. to a solution of 7.5 g of the above-described nonpolar alcohol in 32.6 ml of pyridine, and it is stirred for 18 more hours at room temperature. Then, it is mixed with ice water, stirred for 2 hours, diluted with ether, washed with water, 10% sulfuric acid, water, saturated sodium bicarbonate solution and water. After drying on sodium sulfate and filtration, it is concentrated by evaporation in a vacuum. The residue that is thus obtained is purified by chromatography on silica gel. With hexane/0–35% ether, 8.8 g of the benzoate is obtained as a colorless oil.

IR (Film): 2933, 1716, 1600, 1490, 1450, 1314, 1268, 1178, 1109, 1070, 1026, 994, 962, 890, 757, 712, 692, 526 cm$^{-1}$ 3c) (5R)-5-tert-Butyl-dimethylsilyloxy-1-{(2S)-1-oxo-2-methyl-cyclohexyl-2-yl]-7,7-trimethylene-10-phenyl-(1E,3E)-1,3-decadien-9-ine 3.9 g of the ester, produced under Example 3b), is dissolved in 15.6 ml of tetrahydrofuran and 156 ml of a mixture (65:35:10/acetic acid:water:tetrahydrofuran) and stirred under nitrogen at 40° C. for 24 hours. Then, the reaction mixture is cooled in an ice bath, carefully brought to pH 8 with 218 ml of ice-cold 8 molar sodium hydroxide solution, and stirred for 30 more minutes at room temperature. It is now diluted with ether, washed with water, dried on sodium sulfate, and after filtration, it is concentrated by evaporation in a vacuum. Without further purification, 3.9 g of the ketone is obtained as a colorless oil. 2.3 g of potassium carbonate is added to a solution of 3.9 g of the above-described ketone in 117 ml of methanol, and it is stirred for 24 hours at room temperature. Then, it is diluted with ether, washed with water, dried on sodium sulfate and after filtration, it is concentrated by evaporation in a vacuum. The residue that is thus obtained is purified by chromatography on silica gel. With hexane/0–70% ether, 2.45 g of the alcohol is obtained as a colorless oil.

IR (Film): 3440, 2925, 2860, 1710, 1600, 1490, 1450, 990, 910, 755, 690, 550 cm$^{-1}$ 2 g of imidazole, followed by 2.2 g of tert-butyldimethylsilyl chloride, are added at 0° C. under nitrogen to a solution of 2.79 g of the above-described alcohol in 26.8 ml of N,N-dimethylformamide, it is stirred for 15 minutes at 0° C. and for 24 hours at room temperature. Then, it is diluted with ether, washed with water, 5% sulfuric acid, water, saturated sodium bicarbonate solution and saturated sodium chloride solution. The organic phase is dried on sodium sulfate and after filtration, it is concentrated by evaporation in a vacuum. The residue that is thus obtained is purified by chromatography on silica gel. With hexane/0–20% ether, 3.2 g of the title compound is obtained as a colorless oil.

IR (Film): 2929, 2856, 2361, 1711, 1598, 1490, 1462, 1360, 1255, 1070, 991, 836, 775, 756, 692 cm$^{-1}$

EXAMPLE 4

5-{(E)-(2S)-2-((1E,3E)-(5R)-5-Hydroxy-7,7-trimethylene-10-phenyl-1,3-decadien-9-inyl)-2-methyl-cyclohexyliden}-3-oxa-pentanoic acid 20.3 ml of 1 molar sodium hydroxide solution is added to a solution of 2.1 g of the ester, produced according to Example 3), in 21 ml of methanol, and it is stirred for 24 more hours at room temperature. Then, it is acidified to pH 5 with 10% sulfuric acid, extracted with ethyl acetate, the combined organic phases are washed with saturated sodium chloride solution, dried on sodium sulfate, and after filtration, it is concentrated by evaporation in a vacuum. The residue that is thus obtained is purified by chromatography on silica gel. With hexane/0–20% ether, 3.2 g of the title compound is obtained as a colorless oil.

IR (Film): 3445, 2930, 2860, 1740, 1600, 1490, 1445, 1375, 1240, 1115, 1050, 760, 690, 550 cm$^{-1}$

EXAMPLE 5

5-{(E)-(2S)-((1E,3E)-(5S)-5-Hydroxy-7,7-trimethylene-10-phenyl-1,3-decadien-9-inyl)-2-methyl-cyclohexylidene}-3-oxa-pentanoic acid-tert-butyl ester A solution of 1.4 g of phosphonoacetic acid triethyl ester in 6.3 ml of ethylene glycol dimethyl ether is added in drops at 0° C. under nitrogen to a suspension of 252 mg of sodium hydride (60% in mineral oil) in 6.3 ml of ethylene glycol dimethyl ether, and it is stirred for 1 more hour. A solution of 1.55 g of the (5S)-5-tert-butyl-dimethylsilyloxy-1-{(2S)-1-oxo-2-methyl-cyclohexyl-2-yl}-7,7-trimethylene-10-phenyl-(1E,3E)-1,3-decadien-9-ine, produced according to Example 5b), in 6.3 ml of ethylene glycol dimethyl ether is now added in drops to the reaction mixture, and it is stirred for 24 hours at 50° C. Then, saturated ammonium chloride solution is added and extracted with ether. The combined organic phases are washed with semi-saturated sodium chloride solution, dried on sodium sulfate, and after filtration, it is concentrated by evaporation in a vacuum. The residue that is thus obtained is purified by chromatography on silica gel. With hexane/0–10% ether, 1.5 g of the ester is obtained as a colorless oil.

IR (Film): 2930, 2860, 1720, 1635, 1600, 1490, 1440, 1380, 1250, 1175, 990, 835, 775, 755, 690, 550 cm$^{-1}$ 4.9 ml of diisobutylaluminum hydride (20% in toluene) is added in drops at –70° C. under nitrogen to a solution of 1.5 g of the above-described ester in 16 ml of toluene, and it is stirred for 30 more minutes. Then, 1.6 ml of isopropanol is carefully added in drops, and it is stirred for 5 minutes. It is now mixed with water, stirred for 2 hours at room temperature, the white precipitate is filtered off and washed thoroughly with ethyl acetate. The filtrate is concentrated by evaporation in a vacuum. The residue that is thus obtained is purified by chromatography on silica gel. With hexane/0–70% ether, 1.38 g of the allyl alcohol is obtained as a colorless oil.

IR (Film): 3331, 2928, 2855, 1656, 1598, 1490, 1462, 1442, 1360, 1255, 1070, 994, 836, 809, 775, 755, 691 cm$^{-1}$ 2.6 g of bromoacetic acid-tert-butyl ester, followed by 8 ml of 25% sodium hydroxide solution and 63 mg of tetrabutylammonium hydrogen sulfate, are added to a solution of 1.38 g of the above-described alcohol in 13 ml of toluene. It is now stirred for 24 hours under nitrogen at room temperature. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–30% ether, 1.82 g of the ether is obtained as a colorless oil.

IR (Film): 2928, 2856, 1749, 1590, 1472, 1392, 1368, 1297, 1255, 1223, 1124, 994, 939, 836, 775, 756, 692 cm$^{-1}$ 4.5 g of tetrabutylammonium fluoride×3 H$_2$O is added at room temperature under nitrogen to a solution of 1.82 g of the above-described ether in 73 ml of tetrahydrofuran, and it is stirred for 4 more hours. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–70% ether, 1.25 g of the title compound is obtained as a colorless oil.

IR (Film): 3470, 2930, 2860, 1750, 1650, 1600, 1490, 1370, 1225, 1160, 1120, 990, 845, 760, 690, 550 cm$^{-1}$ The starting material for the above title compound is produced as follows:

5a) (5S)-5-Benzoyloxy-1{-(2S)-1,1-ethylenedioxy-2-methyl-cyclohexyl-2-yl}7,7-trimethylene-10-phenyl-(1E,3E)-1,3-decadien-9-ine 4.6 ml of benzoyl chloride is added at 0° C. to a solution of 8.24 g of the polar alcohol, produced in Example 5), in 35.8 ml of pyridine, and it is stirred for 24 more hours at room temperature. Then, it is mixed with ice water, stirred for 2 hours, diluted with ether, washed with water, 10% sulfuric acid, water, saturated sodium bicarbonate solution and water. After drying on sodium sulfate and filtration, it is concentrated by evaporation in a vacuum. The residue that is thus obtained is purified by repeated chromatography on silica gel. With hexane/0–20% ether, 4.05 g of the benzoate is obtained as a colorless oil.

5b) (5S)-5-Tert-butyl-dimethylsilyloxy-1-{(2S)-1-oxo-2-methyl-cyclohexyl-2-yl}-7,7-trimethylene-10-phenyl-(1E,3E)-1,3-decadien-9-ine 21 g of the benzoate, produced under Example 5a), is dissolved in 12 ml of tetrahydrofuran and 118 ml of a mixture (65:35:10/acetic acid:water:tetrahydrofuran), and it is stirred under nitrogen at 40° C. for 24 hours. Then, the reaction mixture is cooled in an ice bath, carefully brought to pH 8 with 165 ml of ice-cold 8 molar sodium hydroxide solution and stirred for 30 more minutes. It is now extracted with ether, the combined organic phases are washed with saturated sodium chloride solution, dried on sodium sulfate, and after filtration, it is concentrated by evaporation in a vacuum. 2.95 g of the ketone is obtained as a colorless oil without further purification.

1.7 g of potassium carbonate is added to a solution of 2.95 g of the above-described ketone in 89 ml of methanol, and it is stirred for 24 hours at room temperature. Then, it is diluted with ether, washed with water, dried on sodium sulfate, and after filtration, it is concentrated by evaporation in a vacuum. The residue that is thus obtained is purified by chromatography on silica gel. With hexane/0–70% ether, 1.12 g of the alcohol is obtained as a colorless oil.

IR (Film): 3450, 2930, 2860, 1740, 1710, 1600, 1490, 1440, 1425, 1370, 1310, 1240, 1120, 1060, 990, 910, 760, 690, 530 cm$^{-1}$ 1.1 g of imidazole, followed by 1.2 g of tert-butyldimethylsilyl chloride, are added at 0° C. under nitrogen to a solution of 1.5 g of the above-described alcohol in 14 ml of N,N-dimethylformamide, and it is stirred for 15 minutes at 0° C. and for 24 hours at room temperature. Then, it is diluted with ether, washed with water, 5% sulfuric acid, water, saturated sodium bicarbonate solution and saturated sodium chloride solution. The organic phase is dried on sodium sulfate, and after filtration, it is concentrated by evaporation in a vacuum. The residue that is thus obtained is purified by chromatography on silica gel. With hexane/0–20% ether, 1.55 g of the title compound is obtained as a colorless oil.

IR (Film): 2929, 2856, 2361, 1711, 1598, 1490, 1462, 1443, 1360, 1255, 1070, 992, 836, 775, 755, 692 cm$^{-1}$

EXAMPLE 6

5-{(E)-(2S)-2-((1E,3E)-(5S)-5-Hydroxy-7,7-trimethylene-10-phenyl-1,3-decadien-9-inyl)-2-methyl-cyclohexylidene}-3-oxa-pentanoic acid 11 ml of 1 molar sodium hydroxide solution is added to a solution of 1.15 g of the ester, produced according to Example 5), in 12 ml of methanol and 12 ml of tetrahydrofuran, and it is stirred for 24 more hours at room temperature. Then, it is set at pH 5 with 10% sulfuric acid, extracted with ethyl acetate, the combined organic phases are washed with saturated sodium chloride solution, dried on sodium sulfate, and after filtration, it is concentrated by evaporation in a vacuum. The residue that is thus obtained is purified by chromatography on silica gel. With hexane/0–50% ethyl acetate, 1 g of the title compound is obtained as a colorless oil.

IR (Film): 3440, 2930, 2855, 1735, 1655, 1600, 1490, 1440, 1370, 1240, 1115, 1050, 990, 755, 690 cm$^{-1}$

EXAMPLE 7

5-{(E)-(2S)-2-2((1E,3E)-(5-R)-5-Hydroxy-8,8-trimethylene-11-phenyl-1,3-undecadien-10-inyl)-2-methyl-cyclohexylidene}-3-oxy-pentanoic acid-tert-butyl ester A solution of 2.3 g of phosphonoacetic acid triethyl ester in 10 ml of ethylene glycol dimethyl ether is added in drops at 0° C. under nitrogen to a suspension of 411 mg of sodium hydride (60% in mineral oil) in 10 ml of ethylene glycol dimethyl ether, and it is stirred for 1 more hour at room temperature. A solution of 2.6 g of the ketone, produced according to Example 7c), in 10 ml of ethylene glycol dimethyl ether is now added in drops to the reaction mixture and stirred for 24 hours at 50° C. Then, it is added to saturated ammonium chloride solution and diluted with ether. The organic phase is washed with semi-saturated sodium chloride solution, dried on sodium sulfate, and after filtration, it is concentrated by evaporation in a vacuum. The residue that is thus obtained is purified by chromatography on silica gel. With hexane/0–10% ether, 2.74 g of the ester is obtained as a colorless oil.

IR (Film): 2930, 2850, 1715, 1630, 1600, 1490, 1440, 1375, 1250, 1170, 990, 835, 775, 755, 690 cm$^{-1}$ 7.6 ml of diisobutylaluminum hydride (20% in toluene) is added in drops at −70° C. under nitrogen to a solution of 2.39 g of the above-described ester in 25 ml of toluene, and it is stirred for 30 more minutes. Then, 2.5 ml of isopropanol is carefully added in drops, and it is stirred for 5 minutes. It is now mixed with water, stirred for 2 hours at room temperature, the white precipitate is filtered off and washed thoroughly with ethyl acetate. The filtrate is concentrated by evaporation in a vacuum. The residue that is thus obtained is purified by chromatography on silica gel. With hexane/0–70% ether, 1.95 g of the allyl alcohol is obtained as a colorless oil.

IR (Film): 3260, 2928, 2855, 1490, 1442, 1254, 1070, 993, 835, 775, 755, 691 cm$^{-1}$ 3.6 g of bromoacetic acid-tert-butyl ester, followed by 11.4 ml of 25% sodium hydroxide solution and 87 mg of tetrabutylammonium hydrogen sulfate, are added to a solution of 1.95 g of the above-described alcohol in 18.5 ml of toluene. It is now stirred for 24 hours under nitrogen at room temperature. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–30% ether, 3.73 g of the ether is obtained as a colorless oil.

IR (Film): 2930, 2856, 1748, 1490, 1456, 1393, 1369, 1297, 1256, 1161, 994, 951, 836, 775, 756, 692 cm$^{-1}$ 9.1 g of tetrabutylammonium fluoride×3 H$_2$O is added at room temperature under nitrogen to a solution of 3.73 g of the above-described ether in 145 ml of tetrahydrofuran, and it is stirred for 4 more hours. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–70% ether, 1.62 g of the title compound is obtained as a colorless oil.

IR (Film): 3460, 2930, 2855, 1745, 1650, 1600, 1490, 1440, 1370, 1225, 1160, 1120, 990, 845, 755, 690 cm$^{-1}$ The starting material for the above title compound is produced as follows:

7a) 2-Oxo-5,5-trimethylene-8-phenyl-oct-6-ine-phosphonic acid-dimethyl ester 261 ml of diisobutylaluminum hydride (20% in toluene) is added in drops at −70° C. under nitrogen to a solution of 36.25 g of 3,3-trimethylene-6-phenyl-5-inoic acid methyl ester (described in German Laid-Open Specification DE 4242390 Al) in 267 ml of toluene, and it is stirred for 30 more minutes. Then, 67 ml of isopropanol is carefully added in drops, and it is stirred for 5 minutes. It is now mixed with water, stirred for 3 hours at room temperature, the white precipitate is filtered off, and washed thoroughly with ethyl acetate. The filtrate is concentrated by evaporation in a vacuum. The residue that is thus obtained is purified by chromatography on silica gel. With hexane/0–80% ether, 30.4 g of the alcohol is obtained as a colorless oil.

40.6 g of p-toluenesulfonic acid chloride is added at 0° C. to a solution of 30.4 g of the above-described alcohol in 88 ml of pyridine, it is stirred for 4 more hours and allowed to stand for 20 hours at about 6° C. Then, it is mixed with ice water and stirred for 2 hours at room temperature. It is now diluted with ether, washed with water, 10% sulfuric acid, water, saturated sodium bicarbonate solution and with saturated sodium chloride solution. The organic phase is dried on sodium sulfate, and after filtration, it is concentrated by evaporation in a vacuum. 49 g of the tosylate is obtained as a colorless oil without further purification.

7.8 g of sodium cyanide is added to a solution of 49 g of the above-described tosylate in 254 ml of dimethyl sulfoxide, and it is stirred for 3.5 hours at 80° C. After cooling, it is poured on ice water, extracted with ether, the combined organic phases are washed with water, dried on sodium sulfate, and after filtration, it is concentrated by evaporation in a vacuum. The residue that is thus obtained is purified by chromatography on silica gel. With hexane/0–50% ether, 28.3 g of the nitrile is obtained as a colorless oil.

IR (Film): 3060, 2990, 2930, 2250, 1600, 1570, 1490, 1440, 1425, 1385, 1070, 1030, 915, 760, 690, 525 cm$^{-1}$ 165.8 ml of diisobutylaluminum hydride (20% in toluene) is added in drops at −70° C. under nitrogen to a solution of 28.3 g of the above-described nitrile in 270 ml of toluene, and it is stirred for 40 more minutes. Then, 20 ml of isopropanol is carefully added in drops, and it is stirred for 10 minutes. It is now mixed with saturated ammonium chloride solution, stirred for 6 hours at room temperature, the white precipitate is filtered off and washed thoroughly with ethyl acetate. The filtrate is concentrated by evaporation in a vacuum. 32 g of the aldehyde is obtained as a colorless oil without further purification.

79.4 ml of Jones reagent is added in drops at 0° C. to a solution of 32 g of the above-described aldehyde in 400 ml of acetone, and it is stirred vigorously for 1 hour. Then, 120 ml of isopropanol is added, and it is stirred for 30 minutes at room temperature. It is now suctioned off on Celite and rewashed with ether. The filtrate is washed with semi-saturated sodium chloride solution, dried on sodium sulfate, and after filtration, it is concentrated by evaporation in a vacuum. The residue that is thus obtained is purified by chromatography on silica gel. With hexane/0–100% ether, 13.87 g of the acid is obtained as a colorless oil.

23.33 g of potassium carbonate followed by 10.5 ml of methyl iodide are added to a solution of 18.18 g of the above-described acid in 106 ml of acetone, and it is stirred for 24 hours at room temperature. Then, it is suctioned off on Celite, rewashed with ethyl acetate and concentrated by evaporation in a vacuum. The residue is diluted with ether, washed with water, saturated sodium chloride solution, dried on sodium sulfate, and after filtration, it is concentrated by evaporation in a vacuum. The residue that is thus obtained is purified by chromatography on silica gel. With hexane/0–40% ether, 14.53 g of the ester is obtained as a colorless oil.

15 ml of methanephosphonic acid dimethyl ester is dissolved in 186 ml of tetrahydrofuran at −70° C., mixed drop by drop with 80 ml of n-butyllithium and stirred for 1 more hour. A solution of 14.53 g of the above-described ester in 34 ml of tetrahydrofuran is now added in drops to the reaction mixture and stirred for 5 more hours. Then, 10.1 ml of acetic acid is added, and the reaction mixture is allowed to stand overnight at about 6° C. After concentration by evaporation in a vacuum, it is mixed with water, extracted with methylene chloride, the organic phase is dried on sodium sulfate, and after filtration, it is concentrated by evaporation in a vacuum. The residue that is thus obtained is purified by chromatography on silica gel. With hexane/0–100% ethyl acetate, 12.08 g of the title compound is obtained as a colorless oil.

IR (Film): 3288, 2945, 2893, 2360, 2102, 1725, 1675, 1598, 1558, 1506, 1496, 1442, 1424, 1191, 1113, 1078, 1030, 967, 946, 757, 692, 668, 526 cm$^{-1}$ 7b) (5R)-5-Benzoyloxy-1-{(2S)-1,1-ethylenedioxy-2-methyl-cyclohexyl-2-yl}-8,8-trimethylene-11-phenyl-(1E, 3E)-1,3-undecadien-10-ine A solution of 12.08 g of the phosphonate, produced under Example 7a), in 63 ml of ethylene glycol dimethyl ether is added in drops at 0° C. under nitrogen to a suspension of 1.38 g of sodium hydride (60% in mineral oil) in 42 ml of ethylene glycol dimethyl ether, and it is stirred for 1 more hour. A solution of 6.34 g of the aldehyde, described in 1b), in 63 ml of ethylene glycol dimethyl ether is now added in drops to the reaction mixture, and it is stirred for 30 minutes at 0° C. and for 24 hours at room temperature. Then, saturated ammonium chloride solution is added and extracted with ether. The combined organic phases are washed with semi-saturated sodium chloride solution, dried on sodium sulfate, and after filtration, it is concentrated by evaporation in a vacuum. The residue that is thus obtained is purified by chromatography on silica gel. With hexane/0–40% ether, 11.7 g of the ketone is obtained as a colorless oil.

IR (Film): 2940, 2860, 1690, 1660, 1630, 1595, 1440, 1370, 1335, 1290, 1190, 1090, 1005, 965, 950, 800, 760, 695, 560 cm$^{-1}$ 1.5 g of cerium trichloride heptahydrate is added at −70° C. under nitrogen to a solution of 11.7 g of the above-described ketone in 215 ml of methanol and 22 ml of tetrahydrofuran, and it is stirred for 30 more minutes. 1.5 g of sodium borohydride is now added, and it is stirred for 1 more hour. Then, 13 ml of acetone is added in drops, it is stirred for 15 minutes at room temperature, the pH is set at 7 with glacial acetic acid, and it is concentrated by evaporation in a vacuum at 30° C. The residue is diluted with water/ether 1:1, extracted with ether, and the combined organic phases are washed with water and saturated sodium chloride solution. It is dried on sodium sulfate, and after filtration, it is concentrated by evaporation in a vacuum. The residue that is thus obtained is separated by repeated chromatography on silica gel. With hexane/0–100% ether mixtures, first 5.35 g of the nonpolar β-configured alcohol and 5.63 g of the polar α-configured alcohol are obtained.

3 ml of benzoyl chloride is added at 0° C. to a solution of 5.35 g of the above-described nonpolar alcohol in 22.6 ml of pyridine, and it is stirred for 24 more hours at room temperature. Then, it is mixed with ice water, stirred for 2 hours, diluted with ether, and washed with water, 10% sulfuric acid, water, saturated sodium bicarbonate solution and water. After drying on sodium sulfate and filtration, it is concentrated by evaporation in a vacuum. The residue that is thus obtained is purified by chromatography on silica gel. With hexane/0–35% ether, 5.8 g of the benzoate is obtained as a colorless oil.

IR (Film): 2930, 2860, 1720, 1655, 1600, 1585, 1496, 1450, 1315, 1270, 1180, 1110, 1080, 1030, 995, 960, 950, 890, 880, 760, 715, 690, 530 cm$^{-1}$ 7c) (5R)-5-Tert-butyl-dimethylsilyloxy-1-{(2S)-1-oxy-2-methyl-cyclohexyl-2-yl}-8,8-trimethylene-11-phenyl-(1E, 3E)-1,3-undecadien-10-ine 2.3 g of the ester that is produced under Example 7b) is dissolved in 9.2 ml of tetrahydrofuran and 92 ml of a mixture (65:35:10/acetic acid:water:tetrahydrofuran), and it is stirred under nitrogen at 40° C. for 24 hours. Then, the reaction mixture is cooled in an ice bath, carefully brought to pH 12 with 129 ml of ice-cold 8 molar sodium hydroxide solution and stirred for 30 more minutes at room temperature. It is now diluted with ether, washed with water, dried on sodium sulfate, and after filtration, it is concentrated by evaporation in a vacuum. 2.3 g of the ketone is obtained as a colorless oil without further purification.

1.28 g of potassium carbonate is added to a solution of 2.3 g of the above-described ketone in 69 ml of methanol, and it is stirred for 24 hours at room temperature. Then, it is diluted with ether, washed with water, dried on sodium sulfate, and after filtration, it is concentrated by evaporation in a vacuum. The residue that is thus obtained is purified by chromatography on silica gel. With hexane/0–100% ether, 2.68 g of the alcohol is obtained as a colorless oil.

IR (Film): 3440, 2930, 2860, 1740, 1705, 1600, 1490, 1370, 1240, 990, 755, 690 cm$^{-1}$ 2.5 g of imidazole, followed by 2.8 g of tert-butyldimethylsilyl chloride, are added at 0° C. under nitrogen to a solution of 3.6 g of the above-described alcohol in 34.6 ml of N,N-dimethylformamide, and it is stirred for 15 minutes at 0° C. and for 24 hours at room temperature. Then, it is diluted with ether, and washed with water, 5% sulfuric acid, water, saturated sodium bicarbonate solution and saturated sodium chloride solution. The organic phase is dried on sodium sulfate, and after filtration, it is concentrated by evaporation in a vacuum. The residue that is thus obtained is purified by chromatography on silica gel. With hexane/0–35% ether, 4.1 g of the title compound is obtained as a colorless oil.

IR (Film): 2929, 2856, 2360, 1710, 1598, 1490, 1462, 1360, 1255, 1088, 991, 835, 775, 755, 691, 666 cm$^{-1}$

EXAMPLE 8

5-{(E)-(2S)-2-((1E,3E)-(5R)-5-Hydroxy-8,8-trimethylene-11-phenyl-1,3-undecadien-10-inyl)-2-methyl-cyclohexyliden}-3-oxy-pentanoic acid 14 ml of 1 molar sodium hydroxide solution is added to a solution of 1.5 g of the ester, produced according to Example 7), in 15 ml of methanol and 15 ml of tetrahydrofuran, and it is stirred for 24 more hours at room temperature. Then, it is acidified to pH 5 with 10% sulfuric acid, extracted with ethyl acetate, the combined organic phases are washed with saturated sodium chloride solution, dried on sodium sulfate, and after filtration, it is concentrated by evaporation in a vacuum. The residue that is thus obtained is purified by chromatography on silica gel. With hexane/0–100% ethyl acetate, 1.2 g of the title compound is obtained as a colorless oil.

IR (Film): 3440, 2930, 2855, 1740, 1650, 1600, 1490, 1440, 1370, 1240, 1115, 1045, 990, 755, 690 cm$^{-1}$

EXAMPLE 9

5-{(E)-(2S)-2-((1E,3E)-(5S)-5-Hydroxy-8,8-trimethylene-11-phenyl-1,3-undecadien-10-inyl)-2-methyl-cyclohexylidene}-3-oxy-pentanoic acid-tert-butyl ester A solution of 2.67 g of phosphonoacetic acid triethyl ester in 12 ml of ethylene glycol dimethyl ether is added in drops at 0° C. under nitrogen to a suspension of 474 mg of sodium hydride (60% in mineral oil) in 12 ml of ethylene glycol dimethyl ether, and it is stirred for 1 more hour at room temperature. A solution of 3 g of the ketone, produced under Example 9b), in 12 ml of ethylene glycol dimethyl ether is now added in drops to the reaction mixture and stirred for 24 hours at 50° C. Then, it is added to saturated ammonium chloride solution and diluted with ether. The organic phase is washed with semi-saturated sodium chloride solution, dried on sodium sulfate, and after filtration, it is concentrated by evaporation in a vacuum. The residue that is thus obtained is purified by chromatography on silica gel. With hexane/0–10% ether, 2.74 g of the ester is obtained as a colorless oil.

IR (Film): 2930, 2860, 1720, 1635, 1490, 1440, 1380, 1250, 1175, 995, 885, 775, 755, 690 cm$^{-1}$ 9.4 ml of diisobutylaluminum hydride (20% in toluene) is added in drops at −70° C. under nitrogen to a solution of 2.94 g of the above-described ester in 30.6 ml of toluene, and it is stirred for 30 more minutes. Then, 3 ml of isopropanol is carefully added in drops, and it is stirred for 5 minutes. It is now mixed with water, stirred for 2 hours at room temperature, the white precipitate is filtered off and washed thoroughly with ethyl acetate. The filtrate is concentrated by evaporation in a vacuum. The residue that is thus obtained is purified by chromatography on silica gel. With hexane/0–70% ether, 2.56 g of the allyl alcohol is obtained as a colorless oil.

IR (Film): 3355, 2928, 2855, 1490, 1442, 1360, 1254, 1070, 993, 835, 775, 755, 691 cm$^{-1}$ 4.7 g of bromoacetic acid-tert-butyl ester, followed by 14.9 ml of 25% sodium hydroxide solution and 114 mg of tetrabutylammonium hydrogen sulfate, are added to a solution of 2.56 g of the above-described alcohol in 24 ml of toluene. It is now stirred for 24 hours under nitrogen at room temperature. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–30% ether, 3.72 g of the ether is obtained as a colorless oil.

IR (Film): 2929, 2855, 1749, 1368, 1296, 1256, 1161, 994, 836, 775, 756 cm$^{-1}$ 9.1 g of tetrabutylammonium fluoride×3 H$_2$O is added at room temperature under nitrogen to a solution of 3.72 g of the above-described ether in 145 ml of tetrahydrofuran, and it is stirred for 4 more hours. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–70% ether, 2.23 g of the title compound is obtained as a colorless oil.

IR (Film): 3460, 2920, 2850, 1750, 1650, 1600, 1490, 1440, 1370, 1225, 1160, 1120, 990, 845, 755, 690 cm$^{-1}$ The starting material for the above title compound is produced as follows:

9a) (5S)-5-Benzoyloxy-1-{(2S)-1,1-ethylenedioxy-2-methyl-cyclohexyl-2-yl}-8,8-trimethylene-11-phenyl-(1E,3E)-1,3-undecadien-10-ine 3.1 ml of benzoyl chloride is added at 0° C. to a solution of 5.63 g of the polar alcohol, described in Example 7b), in 23.8 ml of pyridine, and it is stirred for 24 more hours at room temperature. Then, it is mixed with ice water, stirred for 2 hours, diluted with ether, washed with water, 10% sulfuric acid, water, saturated sodium bicarbonate solution and water. After drying on sodium sulfate and filtration, it is concentrated by evaporation in a vacuum. The residue that is thus obtained is purified by chromatography on silica gel. With hexane/0–35% ether, 6.14 g of the benzoate is obtained as a colorless oil.

IR (Film): 2930, 2860, 1720, 1655, 1600, 1585, 1490, 1450, 1315, 1270, 1180, 1110, 1070, 1025, 995, 960, 950, 890, 880, 760, 710, 690, 530 cm$^{-1}$ 9b) (5S)-5-Tert-butyl-dimethylsilyloxy-1-{(2S)-1-oxy-2-methyl-cyclohexyl-2-yl}-8,8-trimethylene-11-phenyl-(1E,3E)-1,3-undecadien-10-ine 5 g of the ester that is produced under Example 9a) is dissolved in 20 ml of tetrahydrofuran and 200 ml of a mixture (65:35:10/acetic acid:water:tetrahydrofuran), and it is stirred under nitrogen at 40° C. for 24 hours. Then, the reaction mixture is cooled in an ice bath, brought carefully to pH 12 with 280 ml of ice-cold 8-molar sodium hydroxide solution, and stirred for 30 more minutes at room temperature. It is now diluted with ether, washed with water, dried on sodium sulfate, and after filtration, it is concentrated by evaporation in a vacuum. 5 g of the ketone is obtained as a colorless oil without further purification.

2.8 g of potassium carbonate is added to a solution of 5 g of the above-described ketone in 150 ml of methanol, and it is stirred for 24 hours at room temperature. Then, it is diluted with ether, washed with water, dried on sodium sulfate, and after filtration, it is concentrated by evaporation in a vacuum. The residue that is thus obtained is purified by chromatography on silica gel. With hexane/0–70% ether, 3 g of the alcohol is obtained as a colorless oil.

IR (Film): (DSC7/8) 3440, 2930, 2860, 1740, 1710, 1600, 1490, 1440, 1370, 1240, 1090, 1040, 990, 755, 690, 530 cm$^{-1}$ 2.8 g of imidazole, followed by 3.1 g of tert-butyldimethylsilyl chloride, are added at 0° C. under nitrogen to a solution of 4 g of the above-described alcohol in 38.4 ml of N,N-dimethylformamide, it is stirred for 15 minutes at 0° C. and for 24 hours at room temperature. Then, it is diluted with ether, and washed with water, 5% sulfuric acid, water, saturated sodium bicarbonate solution and saturated sodium chloride solution. The organic phase is dried on sodium sulfate, and after filtration, it is concentrated by evaporation in a vacuum. The residue that is thus obtained is purified by chromatography on silica gel. With hexane/0–35% ether, 4.52 g of the title compound is obtained as a colorless oil.

IR (Film): 2929, 2856, 2361, 1710, 1598, 1490, 1449, 1360, 1255, 1089, 991, 835, 775, 756, 692, 666 cm$^{-1}$

EXAMPLE 10

5-{(E)-(2S)-((1E,3E)-(5S)-5-Hydroxy-8,8-trimethylene-11-phenal-1,3-undecadien-1β-inyl)-2-methyl-cyclohexylidine}-3-oxa-pentanoic acid 19.7 ml of 1 molar sodium hydroxide solution is added to a solution of 2.1 g of the ester, produced according to Example 9), in 20.4 ml of methanol, and it is stirred for 24 more hours at room temperature. Then, it is acidified to pH 5 with 10% sulfuric acid, extracted with ethyl acetate, the combined organic phases are washed with saturated sodium chloride solution, dried on sodium sulfate, and after filtration, it is concentrated by evaporation in a vacuum. The residue that is thus obtained is purified by chromatography on silica gel. With hexane/0–100% ether, 1.75 g of the title compound is obtained as a colorless oil.

IR (Film): 3440, 2930, 2855, 1740, 1655, 1600, 1490, 1440, 1370, 1240, 1115, 1045, 990, 755, 690 cm$^{-1}$

EXAMPLE 11

5-{(E)-(2S)-((1E,3E)-(5S)-5-Hydroxy-6,6-trimethylene-9-phenyl-1,3-nonadienyl)-2-methyl-cyclohexyliden}-3-oxy-pentanoic acid-tert-butyl ester A solution of 1.7 g of phosphonoacetic acid triethyl ester in 12 ml of ethylene glycol dimethyl ether is added in drops at 0° C. under nitrogen to a suspension of 299 mg of sodium hydride (60% in mineral oil) in 7.4 ml of ethylene glycol dimethyl ether, and it is stirred for 1 more hour at room temperature. A solution of 1.8 g of the ketone, produced under Example 11c), in 12 ml of ethylene glycol dimethyl ether is now added in drops to the reaction mixture, and it is stirred for 24 hours at 50° C. Then, it is added to saturated ammonium chloride solution and diluted with ether. The organic phase is washed with semi-saturated sodium chloride solution, dried on sodium sulfate, and after filtration, it is concentrated by evaporation in a vacuum. The residue that is thus obtained is purified by chromatography on silica gel. With hexane/0–10% ether, 2.06 g of the ester is obtained as a colorless oil.

6.9 ml of diisobutylaluminum hydride (20% in toluene) is added in drops at −70° C. under nitrogen to a solution of 2.06 g of the above-described ester in 22.4 ml of toluene, and it is stirred for 30 more minutes. Then, 2.3 ml of isopropanol is carefully added in drops, and it is stirred for 5 minutes. It is now mixed with water, stirred for 2 hours at room temperature, the white precipitate is filtered off and washed thoroughly with ethyl acetate. The filtrate is concentrated by evaporation in a vacuum. The residue that is thus obtained is purified by chromatography on silica gel. With hexane/0–70% ether, 1.77 g of the allyl alcohol is obtained as a colorless oil.

IR (Film): 3320, 3020, 2920, 2850, 1650, 1600, 1495, 1460, 1360, 1250, 1100, 1050, 990, 835, 770, 745, 700 cm$^{-1}$ 3.4 g of bromoacetic acid-tert-butyl ester, followed by 10.5 ml of 25% sodium hydroxide solution and 83 mg of tetrabutylammonium hydrogen sulfate, are added to a solution of 1.77 g of the above-described alcohol in 17 ml of toluene. It is now stirred for 24 hours under nitrogen at room temperature. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–30% ether, 3.01 g of the ether is obtained as a colorless oil.

IR (Film): 2930, 2856, 1748, 1456, 1393, 1369, 1296, 1256, 1161, 1054, 994, 951, 836, 774, 699 cm$^{-1}$ 7,7 g of tetrabutylammonium fluoride×3 H$_2$O is added at room temperature under nitrogen to a solution of 3.01 g of the above-described ether in 123 ml of tetrahydrofuran, and it is stirred for 24 more hours. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–80% ether, 1.51 g of the title compound is obtained as a colorless oil.

IR (Film): 3480, 2920, 2840, 1740, 1650, 1600, 1495, 1450, 1390, 1360, 1300, 1220, 1160, 1120, 990, 940, 840, 745, 700 cm$^{-1}$ The starting material for the above title compound is produced as follows:

11a) 2-Oxo-3,3-trimethylene-6-phenyl-hexane-phosphonic acid-dimethyl ester 100 mg of palladium/carbon is added at room temperature under hydrogen to a solution of 1 g of 2-oxo-3,3-trimethylene-6-phenyl-hex-5-ine-phosphonic acid dimethyl ester in 10 ml of ethyl acetate, and it is stirred for 6 more hours. Then, it is suctioned off, the residue is rewashed thoroughly with ethyl acetate, and the filtrate is concentrated by evaporation in a vacuum. The residue that is thus obtained is purified by chromatography on silica gel. With hexane/0–100% ethyl acetate, 900 mg of the title compound is obtained as a colorless oil.

11b) (5S)-5-Benzoyloxy-1-{(2S)-ethylenedioxy-2-methyl-6,6-trimethylene-9-phenyl-(1E,3E)-1,3-nonadiene A solution of 8.9 g of the phosphonate, produced under Example 11a), in 50 ml of ethylene glycol dimethyl ether is added in drops at 0° C. under nitrogen to a suspension of 1.1 g of sodium hydride (60% in mineral oil) in 33 ml of ethylene glycol dimethyl ether, and it is stirred for 1 more hour. A solution of 5 g of the aldehyde, described in 1b), in 50 ml of ethylene glycol dimethyl ether is now added in drops to the reaction mixture, and it is stirred for 30 minutes at 0° C. and for 24 hours at room temperature. Then, saturated ammonium chloride solution is added, and it is extracted with ether. The combined organic phases are washed with semi-saturated sodium chloride solution, dried on sodium sulfate, and after filtration, it is concentrated by evaporation in a vacuum. The residue that is thus obtained is purified by chromatography on silica gel. With hexane/0–40% ether, 8.1 g of the ketone is obtained as a colorless oil.

IR (Film): 3030, 2930, 2860, 1680, 1625, 1595, 1500, 1450, 1340, 1180, 1130, 1090, 1010, 960, 950, 880, 750, 700 cm$^{-1}$ 1.1 g of cerium trichloride heptahydrate is added at −70° C. under nitrogen to a solution of 8.1 g of the above-described ketone in 158 ml of methanol and 16 ml of tetrahydrofuran, and it is stirred for 30 more minutes. 1.1 g of sodium borohydride is now added, and it is stirred for 1 more hour. Then, 12 ml of acetone is added in drops, it is stirred for 15 minutes at room temperature, the pH is set at 7 with glacial acetic acid, and it is concentrated by evaporation in a vacuum at 30° C. The residue is diluted with water/ether 1:1, extracted with ether, and the combined organic phases are washed with water and saturated sodium chloride solution. It is dried on sodium sulfate, and after filtration, it is concentrated by evaporation in a vacuum. The residue that is thus obtained is separated by repeated chromatography on silica gel. With hexane/0–50% ether mixtures, first 3.62 g of the nonpolar β-configured alcohol and 4.25 g of the polar α-configured alcohol are obtained.

IR (Film): (Nonpolar alcohol) 3440, 3020, 2920, 1680, 1600, 1495, 1450, 1270, 1180, 1085, 990, 960, 880, 745, 695 cm$^{-1}$ IR (Film): (Polar alcohol) 3480, 3020, 2930, 2680, 1680, 1660, 1600, 1500, 1450, 1180, 1090, 995, 960, 880, 800, 750, 700, 655 cm$^{-1}$ 2.1 ml of benzoyl chloride is added at 0° C. to a solution of 3.62 g of the above-described nonpolar alcohol in 16.2 ml of pyridine, and it is stirred for 24 more hours at room temperature. Then, it is mixed with ice water, stirred for 3 hours, diluted with ether, and washed with water, 10% sulfuric acid, water, saturated sodium bicarbonate solution and water. After drying on sodium sulfate and filtration, it is concentrated by evaporation in a vacuum. The residue that is thus obtained is purified by chromatography on silica gel. With hexane/0–35% ether, 4.26 g of the title compound is obtained as a colorless oil.

11c (5S)-5-Tert-butyl-dimethylsilyloxy-1-{(2S)-1-oxo-2-methyl-cyclohexyl-2-yl}-6,6-trimethylene-9-phenyl-(1E,3E)-1,3-nonadiene 4.26 g of the benzoate that is produced under Example 11b) is dissolved in 17 ml of tetrahydrofuran and 170 ml of a mixture (65:35:10/acetic acid:water:tetrahydrofuran), and it is stirred under nitrogen at 45° C. for 6 hours. Then, the reaction mixture is cooled in an ice bath, carefully brought to pH 12 with 239 ml of ice-cold 8-molar sodium hydroxide solution and stirred for 30 more minutes at room temperature. It is now diluted with ether, washed with water, dried on sodium sulfate, and after filtration, it is concentrated by evaporation in a vacuum. The residue that is thus obtained is purified by chromatography on silica gel. With hexane/0–50% ether, 2 g of the ketone is obtained as a colorless oil.

IR (Film): 3030, 2930, 2860, 1710, 1600, 1500, 1450, 1315, 1270, 1185, 1110, 1070, 990, 940, 750, 710 cm$^{-1}$ 1.2 g of potassium carbonate is added to a solution of 2 g of the above-described ketone in 61 ml of methanol, and it is stirred for 48 hours at room temperature. Then, it is diluted with ether, washed with water, dried on sodium sulfate, and after filtration, it is concentrated by evaporation in a vacuum. The residue that is thus obtained is purified by chromatography on silica gel. With hexane/0–70% ether, 1.5 g of the alcohol is obtained as a colorless oil.

IR (Film): 3454, 2933, 2860, 1707, 1496, 1452, 1089, 992, 699 cm$^{-1}$ 1.1 g of imidazole, followed by 1.2 g of tert-butyldimethyl silyl chloride, are added at 0° C. under nitrogen to a solution of 1.5 g of the above-described alcohol in 15 ml of N,N-dimethylformamide, and it is stirred for 15 minutes at 0° C. and for 24 hours at room temperature. Then, it is diluted with ether, and washed with water, 5% sulfuric acid, water, saturated sodium bicarbonate solution and water. The organic phase is dried on sodium sulfate, and after filtration, it is concentrated by evaporation in a vacuum. The residue that is thus obtained is purified by chromatography on silica gel. With hexane/0–10% ether, 1.8 g of the title compound is obtained as a colorless oil.

IR (Film): 3020, 2920, 2850, 1710, 1590, 1460, 1360, 1250, 1100, 990, 830, 770, 700 cm$^{-1}$

EXAMPLE 12

5-{(E)-(2S)-2-((1E,3E)-(5S)-5-Hydroxy-6,6-trimethylene-9-phenyl-1,3-nonadienyl)-2-methyl-cyclohexylidene}-3-oxa-pentanoic acid 13.4 ml of 1 molar sodium hydroxide solution is added to a solution of 1,36 g of the ester, produced according to Example 11), in 13.4 ml of methanol, and it is stirred for 24 more hours at room temperature. Then, it is acidified to pH 5 with 10% sulfuric acid, extracted with ethyl acetate, the combined organic phases are washed with saturated sodium chloride solution, dried on sodium sulfate, and after filtration, it is concentrated by evaporation in a vacuum. The residue that is thus obtained is purified by chromatography on silica gel. With hexane/0–100% ethyl acetate, 580 mg of the title compound is obtained as a colorless oil.

IR (Film): 3420, 3020, 2920, 2850, 1725, 1650, 1490, 1450, 1400, 1240, 1195, 1110, 990, 745, 700 cm$^{-1}$

EXAMPLE 13

5-{(E)-(2S)-2-((1E,3E)-(5R,8S)-5-Hydroxy-12,12-dimethyl-8-methyl-1,3,11-dodecatrienyl)-2-methyl-cyclohexyliden}-3-oxa-pentanoic acid-tert-butyl ester A solution of 942 mg of phosphonoacetic acid triethyl ester in 3.2 ml of ethylene glycol dimethyl ether is added in drops at 0° C. under nitrogen to a suspension of 101 mg of sodium hydride (60% in mineral oil) in 3.2 ml of ethylene glycol dimethyl ether, and it is stirred for 1 more hour at room temperature. A solution of 938 mg of the ketone, produced under Example 13c), in 3.2 ml of ethylene glycol dimethyl ether is now added in drops to the reaction mixture, and it is stirred for 26 hours at 50° C. Then, it is added to saturated ammonium chloride solution and diluted with ether. The organic phase is washed with semi-saturated sodium chloride solution, dried on sodium sulfate, and after filtration, it is concentrated by evaporation in a vacuum. The residue that is thus obtained is purified by chromatography on silica gel. With hexane/0–30% ether, 1.04 g of the ester is obtained as a colorless oil.

IR (Film): 2960, 2915, 2860, 1720, 1685, 1460, 1440, 1380, 1310, 1250, 1180, 1130, 1090, 1040, 990, 840, 810, 775 cm$^{-1}$ 3.6 ml of diisobutylaluminium hydride (20% in toluene) is added in drops at −70° C. under nitrogen to a solution of 1 g of the above-described ester in 10 ml of toluene, and it is stirred for 30 more minutes. Then, 1.5 ml of isopropanol is carefully added in drops and stirred for 10 minutes. It is now mixed with water, stirred for 2 hours at room temperature, the white precipitate is filtered off and washed thoroughly with ethyl acetate. The filtrate is concentrated by evaporation in a vacuum. The residue that is thus obtained is purified by chromatography on silica gel. With hexane/0–30% ether, 725 mg of the alcohol is obtained as a colorless oil.

IR (Film): 3320, 2960, 2930, 2860, 1650, 1470, 1460, 1375, 1360, 1250, 1070, 990, 885, 805, 775 cm$^{-1}$ 1.4 g of bromoacetic acid-tert-butyl ester, followed by 4.4 ml of 25% sodium hydroxide solution and 22 mg of tetrabutylammonium hydrogen sulfate, are added to a solution of 690 mg of the above-described alcohol in 10 ml of toluene. It is now stirred for 28 hours under nitrogen at room temperature. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–10% ether, 730 mg of the ether is obtained as a colorless oil.

IR (Film): 2960, 2930, 2860, 1750, 1730, 1650, 1460, 1390, 1370, 1300, 1250, 1220, 1120, 990, 940, 865, 770 cm$^{-1}$ 1.9 g of tetrabutylammonium fluoride×3 H$_2$O is added at room temperature under nitrogen to a solution of 690 mg of the above-described ether in 20 ml of tetrahydrofuran, and it is stirred for 5 more hours. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–30% ether, 500 mg of the title compound is obtained as a colorless oil.

IR (Film): 3440, 2960, 2920, 2850, 1750, 1650, 1460, 1390, 1370, 1300, 1250, 1220, 1160, 1120, 990, 940, 850, 740 cm$^{-1}$ The starting material for the above title compound is produced as follows:

13a) 5-{(2S)-1,1-Ethylenedioxy-2-methyl-cyclohex-2-yl}-(2E,4E)-pentadien-1-al 23.1 g of phosphonoacetic acid triethyl ester, followed by 14 g of 1,8-diazabicyclo[5.4.0]undec-7-ene, are added in drops at room temperature under nitrogen to 4.4 g of lithium chloride in 300 ml of acetonitrile, and it is stirred for 15 more minutes. Then, 15.5 g of the aldehyde, described in Example 1b), in 50 ml of acetonitrile is added in drops to the reaction mixture and stirred for 2 hours. It is now diluted with ether, washed with semiconcentrated sodium chloride solution, dried on sodium sulfate, and after filtration, it is concentrated by evaporation in a vacuum. The residue that is thus obtained is purified by chromatography on silica gel. With hexane/0–30% ether, 13.84 g of the ester is obtained as a colorless oil.

IR (Film): 2980, 2940, 2860, 1710, 1640, 1610, 1460, 1445, 1370, 1330, 1310, 1260, 1240, 1180, 1150, 1140, 1090, 1045, 1005, 960, 950, 880, 800, 750, 720 cm$^{-1}$ 90.2 ml of diisobutylaluminum hydride (20% in toluene) is added in drops at −70° C. under nitrogen to a solution of 13.8 g of the above-described ester in 250 ml of toluene, and it is stirred for 40 more minutes. Then, 25 ml of isopropanol is slowly added in drops, followed by 45 ml of water, and it is stirred vigorously for 2 hours. The precipitate is suctioned off, washed thoroughly with ethyl acetate, and the filtrate is concentrated by evaporation in a vacuum. The residue that is thus obtained is purified by chromatography on silica gel. With hexane/0–30% ether, 11.7 g of the alcohol is obtained as a colorless oil.

IR (Film): 3420, 3020, 2940, 2860, 1660, 1460, 1445, 1370, 1340, 1290, 1275, 1180, 1140, 1090, 990, 950, 880, 800, 750, 650 cm$^{-1}$ 42.5 g of manganese(IV) oxide is added in portions to a solution of 11.66 g of the above-described alcohol in 500 ml of toluene, and it is stirred for 3 hours at room temperature under nitrogen. Then, it is suctioned off on Celite, rewashed with toluene, and the filtrate is concentrated by evaporation in a vacuum. 10.3 g of the title compound is obtained without further purification as a pale yellow-colored oil.

13b) (5R,8S)-5-Acetoxy-1-(2S)-ethylenedioxy-2-methyl-cyclohexyl-2-yl}-12,12-dimethyl-8-methyl-(1E,3E)-1,3,11-dodecatriene 7.2 g of magnesium is introduced into 30 ml of tetrahydrofuran, heated to 60° C. and mixed with iodine. Then, 32.9 g of (S)-(+)-citronellyl bromide in 30 ml of tetrahydrofuran is added in drops. After about 10 ml, the reaction is begun, the residue is added in drops and stirred for 30 more minutes. 62 ml of tetrahydrofuran is now added and cooled to room temperature.

130 ml of the above-described Grignard solution is added in drops at −70° C. under nitrogen to a solution of 10.3 g of the aldehyde, produced according to Example 13a), in 90 ml of tetrahydrofuran. It is stirred for 1 more hour. Then, it is mixed with saturated ammonium chloride solution and diluted with ether. The organic phase is washed with semi-saturated sodium chloride solution, dried on sodium sulfate, and after filtration, it is concentrated by evaporation in a vacuum. 6.04 g of the nonpolar β-configured alcohol and 8.58 g of the polar α-configured alcohol are obtained without further purification.

IR (Film): (Nonpolar alcohol) 3440, 3040, 2940, 2860, 1460, 1445, 1375, 1275, 1180, 1090, 1050, 1020, 990, 960, 950, 890, 880, 800, 750 cm$^{-1}$ IR (Film): (Polar alcohol) 3440, 3030, 2930, 1460, 1450, 1380, 1275, 1180, 1090, 1050, 990, 960, 950, 890, 880 cm$^{-1}$ 9 ml of acetic acid anhydride is added to a solution of 6 g of the above-produced nonpolar alcohol in 22.7 ml of pyridine, and it is stirred under nitrogen for 24 hours at room temperature. Then, it is concentrated by evaporation with toluene several times in a vacuum. The residue that is thus obtained is purified by chromatography on silica gel. With hexane/0–50% ether, 6,6 g of the title compound is obtained as a colorless oil.

IR (Film): 3040, 2930, 2860, 1735, 1650, 1460, 1460, 1445, 1370, 1230, 1180, 1090, 1020, 990, 960, 950, 880, 730 cm$^{-1}$ 13c) (5R,8S)-5-Tert-butyl-dimethylsilyloxy-1-{(2S)-1-oxo-2-methyl-cyclohexyl-2-yl}-12,12-dimethyl-8-methyl-(1E, 3E)-1,3,11-dodecatriene 6.1 g of the acetate that is produced according to Example 13b) is dissolved in 22 ml of tetrahydrofuran and 219 ml of a mixture (65:35:10/acetic acid:water:tetrahydrofuran), and it is stirred for 12 hours under nitrogen at room temperature. Then, it is concentrated by evaporation in a vacuum with toluene several times. The residue that is thus obtained is purified by chromatography on silica gel. With hexane/0–50% ether, 2.5 g of the keto/acetate is obtained as a colorless oil.

IR (Film): 2940, 2860, 1740, 1710, 1660, 1450, 1375, 1240, 1090, 1020, 990, 610 cm$^{-1}$ 2.1 g of potassium carbonate is added to a solution of 2.8 g of the above-described keto-acetate in 84 ml of methanol, and it is stirred for 24 hours at room temperature. Then, it is diluted with ether, washed with semi-saturated sodium chloride solution, dried on sodium sulfate, and after filtration, it is concentrated by evaporation in a vacuum. The residue that is thus obtained is purified by chromatography on silica gel. With hexane/0–50% ether, 2.45 g of the alcohol is obtained as a colorless oil.

IR (Film): 3440, 2940, 2860, 1710, 1450, 1380, 1315, 1180, 1090, 1060, 990 cm$^{-1}$ 1.1 g of imidazole followed by 1.2 g of tert-butyldimethylsilyl chloride are added at 0° C. under nitrogen to a solution of 1.85 g of the above-described alcohol in 20 ml of N,N-dimethylformamide, and it is stirred for 15 minutes at 0° C. and for 23 hours at room temperature. Then, it is diluted with ether, washed with water, 5% sulfuric acid, water, saturated sodium bicarbonate solution and semi-saturated sodium chloride solution. The organic phase is dried on sodium sulfate, and after filtration, it is concentrated by evaporation in a vacuum. The residue that is thus obtained is purified by chromatography on silica gel. With hexane/0–20% ether, 2.04 g of the title compound is obtained as a colorless oil.

IR (Film): 2960, 2930, 2860, 1710, 1470, 1460, 1450, 1380, 1360, 1250, 1090, 990, 940, 830, 770, 6 80 cm$^{-1}$

EXAMPLE 14

5-{(E)-(2S)-2-((1E,3E)-(5R,8S)-5-Hydroxy-12,12-dimethyl-8-methyl-1,3,11-dodecatrienyl)-2-methyl-cyclohexyliden}-3-oxa-pentanoic acid 5.3 ml of 0.5 molar sodium hydroxide solution is added to a solution of 250 mg of the ester, produced according to Example 13), in 5.3 ml of methanol and 2.7 ml of tetrahydrofuran, and it is stirred for 24 more hours at room temperature. Then, it is acidified to pH 5 with 10% sulfuric acid, extracted with ethyl acetate, the combined organic phases are washed with semi-saturated sodium chloride solution, dried on sodium sulfate, and after filtration, it is concentrated by evaporation in a vacuum. The residue that is thus obtained is purified by chromatography on silica gel. With ethyl acetate/0–20% isopropanol, 167 mg of the title compound is obtained as a colorless oil.

IR (Film): 3440, 2960, 2920, 2840, 1730, 1650, 1650, 1600, 1440, 1375, 1230, 1120, 990, 950 cm$^{-1}$

EXAMPLE 15

5-{(E)-(2S)-2-((1E,3E)-(5S, 8S)-5-Hydroxy-12,12-dimethyl-8-methyl-1,3,11-dodecatrienyl)-2-methyl-cyclohexylidene}-3-oxa-pentanoic acid-tert-butyl ester A solution of 897 mg of phosphonoacetic acid triethyl ester in 3 ml of ethylene glycol dimethyl ether is added in drops at 0° C. under nitrogen to a suspension of 147 mg of sodium hydride (60% in mineral oil) in 3 ml of ethylene glycol dimethyl ether, and it is stirred for 1 more hour at room temperature. A solution of 894 mg of the ketone, produced under Example 15b), in 3 ml of ethylene glycol dimethyl ether is now added in drops to the reaction mixture, and it is stirred for 26 hours at 50° C. Then, it is added to saturated ammonium chloride solution and diluted with ether. The organic phase is washed with semi-saturated sodium chloride solution, dried on sodium sulfate, and after filtration, it is concentrated by evaporation in a vacuum. The residue that is thus obtained is purified by chromatography on silica gel. With hexane/0–30% ether, 1.03 g of the ester is obtained as a colorless oil.

3.6 ml of diisobutylaluminum hydride (20% in toluene) is added in drops at −70° C. under nitrogen to a solution of 1 g of the above-described ester in 10 ml of toluene, and it is stirred for 30 more minutes. Then, 1 ml of isopropanol is carefully added in drops and stirred for 10 minutes. It is now mixed with water, stirred for 2 hours at room temperature, the white precipitate is filtered off and washed thoroughly with ethyl acetate. The filtrate is concentrated by evaporation in a vacuum. The residue that is thus obtained is purified by chromatography on silica gel. With hexane/0–20% ether, 760 mg of the alcohol is obtained as a colorless oil.

IR (Film): 3320, 2960, 2920, 2860, 1650, 1470, 1460, 1380, 1360, 1250, 1080, 990, 830, 800, 770, 670 cm$^{-1}$ 1.5 g of bromoacetic acid-tert-butyl ester, followed by 4.6 ml of 25% sodium hydroxide solution and 23 mg of tetrabutylammonium hydrogen sulfate, are added to a solution of 730 mg of the above-described alcohol in 11 ml of toluene. It is now stirred for 28 hours under nitrogen at room temperature. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–10% ether, 796 mg of the ether is obtained as a colorless oil.

IR (Film): 2960, 2920, 2860, 1750, 1730, 1650, 1470, 1460, 1390, 1370, 1300, 1250, 1220, 1160, 1120, 1070, 990, 940, 890, 770, 730, 670 cm$^{-1}$ 1.1 g of tetrabutylammonium fluoride×3 H$_2$O is added at room temperature under nitrogen to a solution of 400 mg of the above-described ether in 12 ml of tetrahydrofuran, and it is stirred for 5 more hours. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–30% ether, 310 mg of the title compound is obtained as a colorless oil.

IR (Film): 3460, 2966, 2920, 2860, 1750, 1650, 1460, 1390, 1370, 1300, 1250, 1220, 1160, 1120, 990, 940, 840, 740 cm$^{-1}$ The starting material for the above title compound is produced as follows:

15a) (5S,8S)-5-Acetoxy-1-{(2S)-Ethylenedioxy-2-methyl-cyclohexyl-2-yl}-12,12-dimethyl-8-methyl-(1E,3E)-1,3,11-dodecatriene 13.8 ml of acetic acid anhydride is added to a solution of 8.5 g of the polar alcohol, described in Example 13b), in 32 ml of pyridine, and it is stirred under nitrogen for 24 hours at room temperature. Then, it is concentrated by evaporation in a vacuum several times with the addition of toluene. The residue that is thus obtained is purified by chromatography on silica gel. With hexane/0–40% ether, 7.46 g of the title compound is obtained as a colorless oil.

IR (Film): 3020, 2920, 2860, 1730, 1650, 1460, 1445, 1370, 1240, 1180, 1090, 1020, 990, 960, 950, 880, 800, 750, 610 cm$^{-1}$ 15b) (5,8S)-5-Tert-butyl-dimethylsilyloxy-1-{(2S)-1-oxo-2-methyl-cyclohexyl-2-yl}-12,11-dimethyl-8-methyl-(1E,3E)-1,3,11-dodecatriene 7 g of the acetate that is produced under Example 15a) is dissolved in 25 ml of tetrahydrofuran and 250 ml of a mixture (65:35:10/acetic acid:water:tetrahydrofuran), and it is stirred under nitrogen at room temperature for 12 hours. Then, the reaction mixture is concentrated by evaporation in a vacuum several times with toluene. The residue that is thus obtained is purified by chromatography on silica gel. With hexane/0–20% ether, 2.05 g of the ketone is obtained as a colorless oil.

IR (Film): 2940, 2860, 1740, 1710, 1450, 1370, 1320, 1240, 1120, 1090, 1060, 1020, 990, 860, 700, 610 cm$^{-1}$ 1.5 g of potassium carbonate is added to a solution of 2 g of the above-described ketone in 60 ml of methanol, and it is stirred under nitrogen at room temperature for 24 hours. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–50% ether, 1.56 g of the alcohol is obtained as a colorless oil.

IR (Film): 3440, 2940, 2860, 1710, 1450, 1380, 1340, 1310, 1120, 1090, 1060, 990, 910, 860, 700 cm$^{-1}$ 1.2 g of imidazole, followed by 1.4 g of tert-butyldimethylsilyl chloride, are added at 0° C. under nitrogen to a solution of 1.5 g of the above-described alcohol in 17 ml of N,N-dimethylformamide, it is stirred for 15 minutes at 0° C. and for 26 hours at room temperature. Then, it is diluted with ether, and washed with water, 5% sulfuric acid, water, saturated sodium bicarbonate solution and saturated sodium chloride solution. The organic phase is dried on sodium sulfate, and after filtration, it is concentrated by evaporation in a vacuum. The residue that is thus obtained is purified by chromatography on silica gel. With hexane/0–20% ether, 1.9 g of the title compound is obtained as a colorless oil.

IR (Film): 2960, 2920, 2860, 1710, 1470, 1460, 1450, 1380, 1360, 1310, 1250, 1010, 990, 940, 840, 780, 680 cm$^{-1}$

EXAMPLE 16

5-{(E)-(2S)-2-((1E,3E)-(5S,8S)-5-Hydroxy-12,12-dimethyl-8-methyl-1,3,11-dodecatrienyl)-2-methyl-cyclohexylidene}-3-oxo-pentanoic acid 4.6 ml of 0.5 molar sodium hydroxide solution is added to a solution of 216 mg of the ester, produced according to Example 15), in 4.6 ml of methanol and 2.3 ml of tetrahydrofuran, and it is stirred for 24 more hours at room temperature. Then, it is acidified to pH 3 with 10% sulfuric acid, extracted with ethyl acetate, the combined organic phases are washed with semi-saturated sodium chloride solution, dried on sodium sulfate, and after filtration, it is concentrated by evaporation in a vacuum. The residue that is thus obtained is purified by chromatography on silica gel. With hexane/0–60% ether, 193 mg of the title compound is obtained as a colorless oil.

IR (Film): 3440, 2960, 2920, 2860, 1730, 1650, 1460, 1380, 1230, 1120, 990, 940, 680 cm$^{-1}$

EXAMPLE 17

5-{(E)-(2S)-((1E,3E)-(5S)-5-Hydroxy-6,6-trimethylene-10-phenyl-1,3-decadien-9-inyl)-2-methyl-cyclohexylidene}-3-oxa-pentanoic acid-tert-butyl ester A solution of 722 mg of phosphonoacetic acid triethyl ester in 2.4 ml of ethylene glycol dimethyl ether is added in drops at 0° C. under nitrogen to a suspension of 119 mg of sodium hydride (60% in mineral oil) in 2.4 ml of ethylene glycol dimethyl ether, and it is stirred for 2 more hours. A solution of 790 mg of the ketone, produced according to Example 17b), in 2.4 ml of ethylene glycol dimethyl ether is now added in drops to the reaction mixture and stirred for 24 hours at 50° C. Then, saturated ammonium chloride solution is added, and it is extracted with ether. The combined organic phases are washed with semi-saturated sodium chloride solution, dried on sodium sulfate, and after filtration, it is concentrated by evaporation in a vacuum. The residue that is thus obtained is purified by chromatography on silica gel. With hexane/0–5% ether, 804 mg of the ester is obtained as a colorless oil.

IR (Film): 2390, 2857, 1716, 1635, 1490, 1443, 1377, 1251, 1174, 1125, 1040, 995, 836, 775, 756, 692, 526 cm$^{-1}$ 2.4 ml of diisobutylaluminum hydride (20% in toluene) is added in drops at −70° C. under nitrogen to a solution of 792 mg of the above-described ester in 7.5 ml of toluene, and it is stirred for 30 more minutes. Then, 0.4 ml of isopropanol is carefully added in drops, and it is stirred for 10 minutes. It is now mixed with water, stirred for 2 hours at room temperature, the white precipitate is filtered off and washed thoroughly with ethyl acetate. The filtrate is concentrated by evaporation in a vacuum. The residue that is thus obtained is purified by chromatography on silica gel. With hexane/0–20% ether, 656 mg of the allyl alcohol is obtained as a colorless oil.

IR (Film): 2254, 2928, 2856, 2360, 1653, 1598, 1490, 1462, 1442, 1360, 1251, 1103, 1053, 994, 836, 775, 755, 691, 526 cm$^{-1}$ 1.2 g of bromoacetic acid-tert-butyl ester, followed by 3.8 ml of 25% sodium hydroxide solution and 21 mg of tetrabutylammonium hydrogen sulfate, are added to a solution of 632 mg of the above-described alcohol in 9.5 ml of toluene. It is now stirred for 24 hours under nitrogen at room temperature. Then, it is diluted with ether and water, acidified with 10% citric acid, extracted with ether, the combined organic phases are washed with semi-saturated sodium chloride solution, dried on sodium sulfate, and after filtration, it is concentrated by evaporation in a vacuum. The residue that is thus obtained is purified by chromatography on silica gel. With hexane/0–10% ether, 716 mg of the ester is obtained as a colorless oil.

IR (Film): 2928, 2856, 1749, 1657, 1598, 1490, 1462, 1392, 1367, 1251, 1223, 1120, 1054, 994, 939, 836, 775, 756, 692, 526 cm$^{-1}$ 701 mg of tetrabutylammonium fluoride×3 H$_2$O is added at room temperature under nitrogen to a solution of 703 mg of the above-described ester in 4.6 ml of tetrahydrofuran, and it is stirred for 18 more hours. Then, it is diluted with ether, washed with semi-saturated sodium chloride solution, the organic phase is dried on sodium sulfate, and after filtration, it is concentrated by evaporation in a vacuum. The residue that is thus obtained is purified by chromatography on silica gel. With hexane/0–20% ether, 485 mg of the title compound is obtained as a colorless oil.

IR (Film): 2470, 2929, 2360, 1747, 1657, 1598, 1490, 1442, 1368, 1225, 1120, 995, 943, 845, 756, 692, 668, 527 cm$^{-1}$ The starting material for the above title compound is produced as follows:

17a) (5R)-5-Benzoyloxy-1-{(2S)-1,1-ethylenedioxy-2-methyl-cyclohexyl-2-yl}-6,6-trimethylene-10-phenyl-(1E,3E)-decadien-9-ine A solution of 9.9 g of 2-oxo-3,3-trimethylene-7-phenyl-hept-6-ine-phosphonic acid-dimethyl ester (described in DE-OS . . . ) in 55 ml of ethylene glycol dimethyl ether is added in drops at 0° C. under nitrogen to a suspension of 1.1 g of sodium hydride (60% in mineral oil) in 55 ml of ethylene glycol dimethyl ether, and it is stirred for 30 more minutes. A solution of 5.42 g of the aldehyde, described in 1b), in 55 ml of ethylene glycol diethylene ether is now added in drops to the reaction mixture and stirred for 4 hours at 50° C. Then, saturated ammonium chloride solution is added, and it is extracted with ether. The combined organic phases are washed with semi-saturated sodium chloride solution, dried on sodium sulfate, and after filtration, it is concentrated by evaporation in a vacuum. The residue that is thus obtained is purified by chromatography on silica gel. With hexane/0–35% ether, 8.59 g of the ketone is obtained as a colorless oil.

IR (Film): 2934, 1678, 1625, 1591, 1490, 1442, 1350, 1227, 1180, 1135, 1089, 1055, 1019, 962, 880, 795, 757, 692, 528 cm$^{-1}$ 691 mg of cerium trichloride heptahydrate is added at −60° C. under nitrogen to a solution of 5 g of the above-described ketone in 100 ml of methanol and 10 ml of tetrahydrofuran, and it is stirred for 30 more minutes. 702 mg of sodium borohydride is now added, and it is stirred for 1.5 more hours. Then, 20 ml of acetone is added in drops, stirred for 15 minutes at room temperature, the pH is set at 7 with glacial acetic acid and concentrated by evaporation in a vacuum at 30° C. The residue is diluted with water/ether 1:1, extracted with ether, and the combined organic phases are washed with semi-saturated sodium chloride solution. It is dried on sodium sulfate, and after filtration, it is concentrated by evaporation in a vacuum. The residue that is thus obtained is separated by repeated chromatography on silica gel. With hexane/0–25% ether mixtures, first 1.54 g of the nonpolar alcohol and 2.63 g of the polar alcohol are obtained as colorless oils.

3.1 ml of benzoyl chloride is added at 0° C. to a solution of 5.57 g of the above-described nonpolar alcohol in 21.5 ml of pyridine, and it is stirred for 1 more hour at 0° C. and for 18 more hours at room temperature. Then, it is mixed with ice water, stirred for 1 hour, diluted with ether, and washed with semi-saturated sodium chloride solution. After drying on sodium sulfate and filtration, it is concentrated by evaporation in a vacuum. The residue that is thus obtained is purified by chromatography on silica gel. With hexane/0–10% ether, 6.46 g of the benzoate is obtained as a colorless oil.

IR (Film): 2920, 2235, 1712, 1650, 1600, 1584, 1491, 1450, 1274, 1093, 880, 802, 757, 714, 618, 526 cm$^{-1}$ 17b) (5R)-5-Tert-butyl-dimethylsilyloxy-1-{(2S)-1-oxo-2-methyl-2-yl}-6,6-trimethylene-10-phenyl-(1E,3E)-1,3-decadien-9-ine 6.45 g of the benzoate that is produced under Example 17a) is dissolved in 185 ml of a mixture (65:35:10/acetic acid:water:tetrahydrofuran), and it is stirred for 20 hours under nitrogen at 45° C. Then, the reaction mixture is concentrated by evaporation in a vacuum several times with toluene. The residue that is thus obtained is purified by repeated chromatography on silica gel. With hexane/0–10% ethyl acetate, 3.09 g of the ketone is obtained as a colorless oil.

IR (Film): 2934, 2862, 2234, 1713, 1599, 1584, 1490, 1450, 1314, 1272, 1176, 1111, 1069, 1026, 992, 941, 859, 804, 757, 712, 692, 526 cm$^{-1}$ 1,33 g of potassium carbonate is added to a solution of 3.08 g of the above-described ketone in 50 ml of methanol, and it is stirred under nitrogen at room temperature for 18 hours. Then, it is diluted with water, extracted with ethyl acetate, the combined organic phases are washed with semi-saturated sodium chloride solution, dried on sodium sulfate, and after filtration, it is concentrated by evaporation in a vacuum. The residue that is thus obtained is purified by chromatography on silica gel. With hexane/0–30% ether, 2.13 g of the alcohol is obtained as a colorless oil.

IR (Film): 3460, 2933, 2862, 1707, 1598, 1490, 1442, 1373, 1312, 1118, 992, 757, 692, 527 cm$^{-1}$ 1.4 g of imidazole, followed by 1.5 g of tert-butyldimethylsilyl chloride, are added at room temperature under nitrogen to a solution of 2.12 g of the above-described alcohol in 29 ml of N,N-dimethylformamide, and it is stirred for 20 hours at room temperature. Then, it is diluted with ether/hexane 1:1, and washed with water and semi-saturated sodium chloride solution. The organic phase is dried on sodium sulfate, and after filtration, it is concentrated by evaporation in a vacuum. The residue that is thus obtained is purified by chromatography on silica gel. With hexane/0–5% ether, 2.39 g of the title compound is obtained as a colorless oil.

IR (Film): 2931, 2840, 1711, 1598, 1490, 1462, 1448, 1360, 1253, 1118, 1062, 992, 908, 836, 775, 756, 692, 526 cm$^{-1}$

EXAMPLE 18

5-{(E)-(2S)-2-((1E,3E)-(5S)-5-Hydroxy-6,6-trimethylene-10-phenyl-1,3-decadien-9-inyl)-2-methyl-cyclohexylidene}-3-oxa-pentanoic acid 4.5 ml of 0.5 molar lithium hydroxide solution, followed by 66 mg of lithium hydroxide, are added to a solution of 462 mg of the ester, produced in Example 17, in 8.8 ml of tetrahydrofuran and 8.8 ml of methanol, and it is stirred for 18 hours at room temperature. Then, it is diluted with water, brought to pH 5 with 1 molar hydrochloric acid, extracted with ethyl acetate, dried on sodium sulfate, and after filtration, it is concentrated by evaporation in a vacuum. The residue that is thus obtained is purified by chromatography on silica gel. With hexane/0–90% ethyl acetate, 178 mg of the title compound is obtained as a colorless oil.

IR (Film): 3450, 2930, 2850, 1740, 1650, 1600, 1490, 1440, 1380, 1240, 1110, 1040, 990, 760, 690, 530 cm$^{-1}$

EXAMPLE 19

5-{(E)-(2S)-2-((1E,3E)-(5S)-5-Hydroxy-6,6-dimethyl-9-phenoxy-1,3-nonadienyl)-2-methyl-cyclohexylidene}-3-oxa-pentanoic acid-tert-butyl ester A solution of 896 mg of phosphonoacetic acid triethyl ester in 3 ml of ethylene glycol dimethyl ether is added in drops at 0° C. under nitrogen to a suspension of 159 mg of sodium hydride (60% in mineral oil) in 3 ml of ethylene glycol dimethyl ether, and it is stirred for 2 more hours. A solution of 969 mg of the ketone, produced according to Example 19c), in 5 ml of ethylene glycol dimethyl ether is now added in drops to the reaction mixture, and it is stirred for 16 hours at 50° C. It is cooled to 0° C. by the still incomplete reaction, and a freshly prepared phosphonate solution (448 mg of phosphonoacetic acid triethyl ester/80 mg of sodium hydride in 6 ml of ethylene glycol dimethyl ether) is added and stirred for 5 hours at 50° C. Then, saturated ammonium chloride solution is added and extracted with ether. The combined organic phases are washed with water and saturated sodium chloride solution, dried on sodium sulfate, and after filtration, it is concentrated by evaporation in a vacuum. The residue that is thus obtained is purified by chromatography on silica gel. With hexane/0–10% ether, 1.03 g of the ester is obtained as a colorless oil.

IR (Film): 2929, 2857, 1716, 1635, 1600, 1498, 1471, 1247, 1173, 1040, 995, 836, 775, 753, 691 cm$^{-1}$ 3.2 ml of diisobutylaluminum hydride (20% in toluene) is added in drops at –70° C. under nitrogen to a solution of 945 mg of the above-described ester in 10 ml of toluene, and it is stirred for 1 more hour. Then, 0.9 ml of isopropanol is carefully added in drops and stirred for 10 minutes. It is now mixed with water, stirred for 2 hours at room temperature, the white precipitate is filtered off and washed thoroughly with ethyl acetate. The filtrate is concentrated by evaporation in a vacuum. The residue that is thus obtained is purified by chromatography on silica gel. With hexane/0–50% ether, 730 mg of the allyl alcohol is obtained as a colorless oil.

IR (Film): 3334, 2927, 2856, 1600, 1497, 1472, 1247, 1109, 1058, 994, 836, 774, 753, 691 cm$^{-1}$ 1.6 ml of bromoacetic acid-tert-butyl ester, followed by 1.8 ml of 25% sodium hydroxide solution and 15 mg of tetrabutylammonium hydrogen sulfate, are added to a solution of 326 mg of the above-described alcohol in 3 ml of toluene. It is now stirred for 6 hours under nitrogen at room temperature. Then, it is diluted with ether, washed with water and saturated sodium chloride solution, the organic phase is dried on sodium sulfate, and after filtration, it is concentrated by evaporation in a vacuum. The residue that is thus obtained is purified by chromatography on silica gel. With hexane/0–10% ether, 350 mg of the ester is obtained as a colorless oil.

IR (Film): 2929, 2856, 1749, 1497, 1472, 1368, 1247, 1119, 1062, 994, 836, 775, 753, 691 cm$^{-1}$ The starting material for the above title compound is produced as follows:

19a) 2-Oxo-3,3-dimethyl-6-phenoxy-hexane-phosphonic acid dimethyl ester 16.3 g of diisopropylamine in 120 ml of tetrahydrofuran is added in drops at 0° C. under nitrogen to 99.3 ml of n-butyllithium, and it is stirred for 45 more minutes. The reaction solution is cooled to –70° C. to –65° C., mixed carefully with 14.3 g of isobutyric acid in 120 ml of tetrahydrofuran, and it is stirred for 1 hour. 30.1 g of 3-phenoxypropyl bromide is dissolved in 200 ml of 1,3-dimethyltetrahydro-2-pyrimidinone and added in drops to the reaction mixture. It is stirred for 30 minutes at –70° C., 1 hour at –30° C. and 1 hour at 0° C. Then, it is added to saturated ammonium chloride solution, extracted with ether, the combined organic phases are washed with saturated sodium chloride solution, dried on sodium sulfate, and after filtration, it is concentrated by evaporation in a vacuum. The residue that is thus obtained is purified by chromatography on silica gel. With hexane/0–10% ether, 24.3 g of the ester is obtained as a colorless oil.

IR (Film): 2951, 2360, 1731, 1600, 1586, 1498, 1474, 1390, 1246, 1197, 1147, 1080, 1048, 990, 755, 692 cm$^{-1}$ 33 g of diisopropylamine in 50 ml of tetrahydrofuran is added at –40° C. under nitrogen to 131 ml of n-butyllithium, and it is stirred for 15 minutes. The reaction mixture is now cooled to –70° C., mixed with 24.9 g of methanephosphoric acid dimethyl ester in 50 tetrahydrofuran (stirred for 30 more minutes), followed by 22 g of the above-described ester in 50 ml of tetrahydrofuran, heated slowly to 0° C. and stirred for 2 hours. Then, it is acidified to pH 2 with 10% sulfuric acid, extracted with ethyl acetate, the combined organic phases are washed with saturated sodium chloride solution, dried on sodium sulfate, and after filtration, it is concentrated by evaporation in a vacuum. The residue that is thus obtained is purified by chromatography on silica gel. With hexane/0–100% ethyl acetate, 28.1 g of the title compound is obtained as a colorless oil.

IR (Film): 2956, 2359, 1704, 1600, 1586, 1497, 1471, 1390, 1247, 1174, 1032, 869, 806, 757, 693 cm$^{-1}$ 19b) (5R)-5-Benzyloxy-1-{(2S)-1,1-ethylenedioxy-2-methyl-cyclohexyl-2-yl}-6,6-dimethyl-9-phenoxy-(1E,3E)-1,3-nonadiene A solution of 22.63 g of the phosphonate, produced under Example 19a), in 150 ml of 1,2-dimethoxyethane is added in drops at 0° C. under nitrogen to a suspension of 2.73 g of sodium hydride (60% in mineral oil) in 90 ml of 1,2-dimethoxyethane, and it is stirred for 1 more hour. A solution of 12.6 g of the aldehyde, produced under Example 1b), in 150 ml of 1,2-dimethoxyethane is now added in drops to the reaction mixture. It is stirred for 30 minutes at 0° C. and for 64 hours at room temperature. Then, saturated ammonium chloride solution is added and extracted with ether. The combined organic phases are washed with saturated sodium chloride solution, dried on sodium sulfate, and after filtration, it is concentrated by evaporation in a vacuum. The residue that is thus obtained is purified by chromatography on silica gel. With hexane/0–30% ether, 22.7 g of the ketone is obtained as a colorless oil.

IR (Film): 2934, 1679, 1625, 1589, 1497, 1470, 1340, 1245, 1179, 1085, 1038, 962, 880, 795, 754, 692 cm$^{-1}$ 3.1 g of cerium trichloride heptahydrate is added at −55° C. under nitrogen to a solution of 22.5 g of the above-described ketone in 240 ml of methanol and 180 ml of tetrahydrofuran, and it is stirred for 30 more minutes. 3.1 g of sodium borohydride is now added, and it is stirred for 3 more hours. Then, 33 ml of acetone is added, stirred for 30 minutes at room temperature, the pH is set at 7 with glacial acetic acid, and concentrated by evaporation in a vacuum at 30° C. The residue is diluted with water/ether 1:1, extracted with ether, and the combined organic phases are washed with water and saturated sodium chloride solution. It is dried on sodium sulfate, and after filtration, it is concentrated by evaporation in a vacuum. The residue that is thus obtained is separated by repeated chromatography on silica gel. With hexane/0–50% ether mixtures, first 6.8 g of the nonpolar β-configured alcohol and 7.7 g of the polar α-configured alcohol are obtained as colorless oils.

IR (Film): (Nonpolar alcohol) 3484, 2947, 2868, 1600, 1586, 1498, 1470, 1365, 1246, 1179, 1088, 993, 961, 880, 754, 692 cm$^{-1}$ IR (Film): (Polar alcohol) 3478, 2947, 2867, 1600, 1586, 1497, 1471, 1365, 1246, 1178, 1088, 993, 961, 880, 754, 692 cm$^{-1}$ 1.5 ml of benzoyl chloride is added at 0° C. to a solution of 4.56 g of the above-described nonpolar alcohol in 1 ml of pyridine, and it is stirred for 24 more hours at room temperature. Then, it is mixed with ice water, stirred for 2 hours, diluted with ether, and washed with water, 10% sulfuric acid, water, saturated sodium bicarbonate solution and water. After drying on sodium sulfate and filtration, it is concentrated by evaporation in a vacuum. The residue that is thus obtained is purified by repeated chromatography on silica gel. With hexane/0–30% ether, 5.8 g of the benzoate is obtained as a colorless oil.

IR (Film): 2947, 2359, 1716, 1600, 1586, 1497, 1269, 1176, 1109, 1026, 949, 754, 712, 692 cm$^{-1}$ 19c) (5R)-5-(Tert-butyl-dimethylsilyloxy-1-{(2S)-1-oxo-2-methyl-cyclohexyl-2-yl}-6,6-dimethyl-9-phenoxy-(1E,3E)-1,3-nonadiene 5.6 g of the ether that is produced under Example 19b) is dissolved in 110 ml of tetrahydrofuran and 150 ml of a mixture (65:35:10/acetic acid:water:tetrahydrofuran) and stirred under nitrogen at 50° C. for 20 hours. Then, the reaction mixture is cooled in an ice bath, carefully brought to pH 8 with ice-cold 8-molar sodium hydroxide solution, and it is stirred for 30 more minutes. It is now extracted with ether, the combined organic phases are washed with saturated sodium chloride solution, dried on sodium sulfate, and after filtration, it is concentrated by evaporation in a vacuum. The residue that is thus obtained is purified by chromatography on silica gel. With hexane/0–20% ether, 3.5 g of the ketone is obtained as a colorless oil.

IR (Film): 2932, 1713, 1600, 1586, 1495, 1450, 1268, 1173, 1110, 992, 835, 755, 712, 692 cm$^{-1}$ 2.1 g of potassium carbonate is added to a solution of 3.4 g of the above-described ketone in 120 ml of methanol, and it is stirred under nitrogen at room temperature for 16 hours. Then, it is diluted with ether, washed with water and saturated sodium chloride solution, the organic phase is dried on sodium sulfate, and after filtration, it is concentrated by evaporation in a vacuum. The residue that is thus obtained is purified by chromatography on silica gel. With hexane/0–30% ether, 2.51 g of the alcohol is obtained as a colorless oil.

IR (Film): 3485, 2934, 2866, 1707, 1600, 1497, 1470, 1246, 1171, 1036, 992, 755, 692 cm$^{-1}$ 1.8 g of imidazole, followed by 2 g of tert-butyldimethylsilyl chloride, are added at 0° C. under nitrogen to a solution of 2.4 g of the above-described alcohol in 25 ml of N,N-dimethylformamide, and it is stirred 15 minutes at 0° C. and for 16 hours at room temperature. Then, it is diluted with ether, and washed with water, 5% sulfuric acid, water, saturated sodium bicarbonate solution and saturated sodium chloride solution. The organic phase is dried on sodium sulfate, and after filtration, it is concentrated by evaporation in a vacuum. The residue that is thus obtained is purified by chromatography on silica gel. With hexane/0–10% ether, 2.7 g of the title compound is obtained as a colorless oil.

IR (Film): 2956, 2857, 1711, 1600, 1498, 1471, 1247, 1110, 1063, 992, 836, 775, 753, 691 cm$^{-1}$

EXAMPLE 20

5-{(E)-(2S)-((1E,3E)-(5S)-5-Hydroxy-6,6-dimethyl-9-phenoxy-1,3-nonadienyl)-2-methyl-cyclohexyliden}-3-oxa-pentanoic acid 1.9 ml of 1 molar sodium hydroxide solution is added to a solution of 170 mg of the ester, produced in Example 19, in 2 ml of tetrahydrofuran and 2 ml of methanol, and it is stirred for 16 hours at room temperature. Then, it is cooled with ice water, acidified to pH 4 with 1 molar sulfuric acid and extracted with ethyl acetate. The combined organic phases are washed with sodium chloride solution, dried on sodium sulfate, and after filtration, it is concentrated by evaporation in a vacuum. The residue that is thus obtained is purified by chromatography on silica gel. With methylene chloride/0–10% methanol, 79 mg of the title compound is obtained as a colorless oil.

IR (Film): 3440, 2960, 2930, 2860, 1620, 1600, 1500, 1470, 1430, 1340, 1250, 1180, 1080, 1040, 990, 950, 760, 690, 600, 510 cm$^{-1}$

EXAMPLE 21

7-{(E)-(2S)-2-((1E,3E)-(5S)-5-Hydroxy-6,6-trimethylene-9-phenyl-1,3-nonadien-8-inyl)-2-methyl-cyclohexyliden}-5-oxa-heptanoic acid 85 mg of 4-bromoorthobutyric acid trimethyl ester, followed by 0.75 ml of 25% sodium hydroxide solution and 3.6 mg of tetrabutylammonium hydrogen sulfate, are added to a solution of 125 mg of the allyl alcohol, produced in Example 1, in 1.9 ml of toluene. It is now stirred for 24 hours under nitrogen at room temperature. Then, it is diluted with ether and water, extracted with ether, the combined organic phases are washed with semi-saturated sodium chloride solution, dried on sodium sulfate, and after filtration, it is concentrated by evaporation in a vacuum. The residue that is thus obtained is purified by chromatography on silica gel. With hexane/0–10% ether, 60.1 mg of the ether is obtained as a colorless oil.

IR (Film): 2929, 1738, 1657, 1598, 1442, 1360, 1252, 1103, 995, 836, 775, 756, 692, 526 cm$^{-1}$ 120 mg of tetrabutylammonium fluoride×3 H$_2$O is added at room temperature under nitrogen to a solution of 114.7 mg of the above-described ester in 0.8 ml of tetrahydrofuran, and it is stirred for 5 more hours. Then, it is diluted with ether, washed with water, the organic phase is dried on sodium sulfate, and after filtration, it is concentrated by evaporation in a vacuum. The residue that is thus obtained is purified by chromatography on silica gel. With hexane/0–30% ether, 62.5 mg of the alcohol is obtained as a colorless oil.

IR (Film): 3450, 2930, 2860, 1740, 1650, 1600, 1490, 1440, 1365, 1260, 1200, 1170, 1100, 990, 805, 755, 690, 525 cm$^{-1}$ 0.7 ml of 0.5 molar lithium hydroxide solution is added to a solution of 67.5 mg of the above-described alcohol in 0.7 ml of tetrahydrofuran and 0.7 ml of methanol, and it is stirred for 40 hours at room temperature. Then, it is diluted with water, brought to pH 5 with 1 molar hydrochloric acid, extracted with ethyl acetate, dried on sodium sulfate, and after filtration, it is concentrated by evaporation in a vacuum. The residue that is thus obtained is purified by chromatography on silica gel. With hexane/0–100% ethyl acetate, 28.4 mg of the title compound is obtained as a colorless oil.

IR (Film): 2960, 2920, 2850, 1710, 1360, 1115, 990, 755, 690, 620 cm$^{-1}$

EXAMPLE 22

5-{(E,Z)-(2S)-2-((1E,3E)-(5S)-5-Hydroxy-6,6-trimethylene-9-phenyl-1,3-nonadien-8-inyl)-2-methyl-cyclohexylidine}-pentanoic acid 3.35 ml of a solution of methanesulfinyl methyl sodium in dimethyl sulfoxide (for production: 1 g of 50% sodium hydride suspension is dissolved in 20 ml of dimethyl sulfoxide for one hour at 70° C.) is added in drops at 15° C. to a solution of 776 mg of 4-carboxybutyltriphenylphosphonium bromide in 3.5 ml of dimethyl sulfoxide, and it is stirred for 30 minutes at room temperature. A solution of 223 mg of (5S)-5-tert-butyl-dimethylsilyloxy-1-{(2S)-1-oxo-cyclohexyl-2-yl}-6,6-trimethylene-9-phenyl-(1E,3E)-1,3-nonadien-8-ine (produced in Example 1d) in 2 ml of dimethyl sulfoxide is added to the red ylene solution, and it is stirred for 24 hours at room temperature under nitrogen. Then, the reaction mixture is added to ice water, acidified to pH 4 with 10% citric acid solution and extracted with ethyl acetate. The organic phase is washed with saturated sodium chloride solution, dried on sodium sulfate, and after filtration, it is concentrated by evaporation in a vacuum. The residue that is thus obtained is purified by chromatography on silica gel. With hexane/0–30% ether, 21 mg of the carboxylic acid is obtained as a colorless oil.

IR (Film): 3300, 2934, 2859, 2203, 1709, 992, 836 cm$^{-1}$ 25 mg of tetrabutylammonium fluoride is added at room temperature under nitrogen to a solution of 19 mg of the above-described carboxylic acid in 0.2 ml of tetrahydrofuran, and it is stirred for 12 hours at room temperature. Then, it is diluted with ether, washed with water, dried on sodium sulfate, and after filtration, it is concentrated by evaporation in a vacuum. The residue that is thus obtained is purified by chromatography on silica gel. With ether 7.3 mg of the title compound is obtained as a colorless oil.

IR (Film): 3400, 2934, 2859, 1709, 1490, 1439, 1246, 994, 756, 692 cm$^{-1}$

EXAMPLE 23

2-{(E)-(2S)-2-((1E,3E)-(5S)-5-Hydroxy-6,6-trimethylene-9-phenyl-1,3-nonadien-8-inyl)-2-methyl-cyclohexylidene}-ethanoic acid 1.2 g of tetrabutylammonium fluoride×3 H$_2$O at room temperature under nitrogen to a solution of 400 mg of the silyl ether, described in Example 1, in 20 ml of tetrahydrofuran, and it is stirred for 4 more hours. Then, it is diluted with ether, washed with water and saturated sodium chloride solution, the organic phase is dried on sodium sulfate, and after filtration, it is concentrated by evaporation in a vacuum. The residue that is thus obtained is purified by chromatography on silica gel. With hexane/0–40% ether, 270 mg of the alcohol is obtained as a colorless oil.

IR (Film): 3478, 2931, 2850, 1716, 1634, 1490, 1443, 1378, 1243, 1180, 1035, 994, 874, 836, 756, 692 cm$^{-1}$ 3 ml of 1 molar sodium hydroxide solution, followed by 50 mg of lithium hydroxide, are added to a solution of 270 mg of the above-described alcohol in 5 ml of tetrahydrofuran and 4 ml of methanol, and it is stirred for 5 hours at 50° C. and for 20 hours at room temperature. Then, it is acidified to pH 4 with 1N sulfuric acid, extracted with ether, the combined organic phases are dried with saturated sodium chloride solution on sodium sulfate, and after filtration, it is concentrated by evaporation in a vacuum. The residue that is thus obtained is purified by chromatography on silica gel. With hexane/0–40% ether, 400.7 mg of the title compound is obtained as a colorless oil.

IR (Film): 3400, 2940, 2860, 1690, 1630, 1490, 1440, 1250, 990, 760, 690, 530 cm$^{-1}$

EXAMPLE 24

5-{(E)-(2S)-2-((1E,3E)-(5S)-5-Hydroxy-6,6-trimethylene-9-phenyl-1,3-nonadien-8-inyl)-2-methyl-cyclohexyliden}-3-oxy-pentanoic acid-N-(5-tetraloxyl)-amide 14.8 ml of 1 molar sodium hydroxide solution is added to a solution of 2.3 g of the ester, produced in Example 1), in 18 ml of methanol and 20 ml of tetrahydrofuran, and it is stirred for 16 more hours at room temperature. Then, it is set at pH 5 with 10% sulfuric acid, extracted with ethyl acetate, the combined organic phases are washed with water and saturated sodium chloride solution, dried on sodium sulfate, and after filtration, it is concentrated by evaporation in a vacuum. The residue that is thus obtained is purified by chromatography on silica gel. With hexane/0–100% ethyl acetate/0–5% isopropanol, 1.69 g of the acid is obtained as a colorless oil.

IR (Film): 2930, 2359, 1732, 1651, 1598, 1490, 1462, 1442, 1360, 1250, 1106, 1060, 994, 835, 775, 755, 691 cm$^{-1}$ 58 mg of 5-aminotetrazole, followed by 117 mg of N,N-dicyclohexylcarbodiimide in 0.5 ml of tetrahydrofuran, are added at room temperature under nitrogen to a solution of 281 mg of the above-described acid in 1.5 ml of tetrahydrofuran, and it is stirred for 20 hours at room temperature. Then, the precipitate is suctioned off, washed with methylene chloride, and concentrated by evaporation in a vacuum. The residue that is thus obtained is purified by chromatography on silica gel. With methylene chloride/ 0–20% methanol, 300 mg of the tetrazole is obtained as a colorless oil.

IR (Film): 3200, 2920, 2850, 2160, 1690, 1610, 1580, 1520, 1480, 1400, 1350, 1240, 1100, 1050, 980, 830, 770, 750, 730, 680, 520

900 mg of tetrabutylammonium fluoride×3 $H_2O$ is added at room temperature under nitrogen to a solution of 280 mg of the above-described silyl ether in 6 ml of tetrahydrofuran, and it is stirred for 5 more hours at 40° C. Then, it is diluted with ethyl acetate, washed with water and saturated sodium chloride solution, the organic phase is dried on sodium sulfate, and after filtration, it is concentrated by evaporation in a vacuum. The residue that is thus obtained is purified by chromatography on silica gel. With methylene chloride/ 0–30% methanol, 184 mg of the title compound is obtained as a colorless oil.

IR (Film): 3400, 3200, 2930, 2860, 1700, 1620, 1590, 1490, 1400, 1100, 990, 760, 690 $cm^{-1}$

EXAMPLE 25

5-{(E)-(2S)-2-((1E,3E)-(5S)-5-Hydroxy-6,6-trimethylene-9-phenyl-1,3-nonadien-8-inyl)-2-methyl-cyclohexyliden}-3-oxa-pentanoic acid-methyl ester 673 mg of potassium carbonate, followed by 689 mg of methyl iodide, are added to a solution of 1 g of the acid, described in Example 4, in 3.23 ml of acetone, and it is stirred for 24 hours at room temperature. Then, it is diluted with ether, washed with saturated sodium chloride solution, dried on sodium sulfate, and after filtration, it is concentrated by evaporation in a vacuum. The residue that is thus obtained is purified by chromatography on silica gel. With hexane/0–70% ether, 920 mg of the title compound is obtained as a colorless oil.

IR (Film): 3480, 2920, 2850, 1760, 1650, 1600, 1490, 1440, 1280, 1210, 1120, 990, 940, 920, 760, 690, 520 $cm^{-1}$

EXAMPLE 26

5-{(E)-(2S)-((1E,3E)-(5S)-5-Hydroxy-6,6-trimethylene-9-phenyl-1,3-nonadien-8-inyl)-2-methyl-cyclohexyliden}-3-oxa-pentanoic acid-amide 423 mg of imidazole, followed by 470 mg of tert-butyldimethylsilyl chloride, are added at 0° C. under nitrogen to a solution of 740 mg of the alcohol, described in Example 25, in 5.6 ml of N,N-dimethylformamide, and it is stirred for 15 minutes at 0° C. and for 24 hours at room temperature. Then, it is diluted with ether, and washed with water, 10% sulfuric acid, water, saturated sodium bicarbonate solution, and saturated sodium chloride solution. The organic phase is dried on sodium sulfate, and after filtration, it is concentrated by evaporation in a vacuum. The residue that is thus obtained is purified by chromatography on silica gel. With hexane/0–30% ether, 890 mg of the title compound is obtained as a colorless oil.

IR (Film): 2928, 2855, 2360, 1757, 1684, 1653, 1540, 1472, 1362, 1362, 1254, 1205, 1122, 1070, 994, 938, 836, 775, 756, 691 $cm^{-1}$ 2.4 ml of 1 molar sodium hydroxide solution is added to a solution of 280 mg of the above-described ester in 2.5 ml of methanol and 2.5 tetrahydrofuran, and it is stirred for 24 more hours at room temperature. Then, it is set at pH 5 with 10% sulfuric acid, extracted with ethyl acetate, the combined organic phases are washed with saturated sodium chloride solution, dried on sodium sulfate, and after filtration, it is concentrated by evaporation in a vacuum. The residue that is thus obtained is purified by chromatography on silica gel. With hexane/0–100% ethyl acetate, 250 mg of the acid is obtained as a colorless oil.

IR (Film): 2928, 2855, 1740, 1490, 1462, 1442, 1372, 1249, 1110, 1101, 994, 938, 836, 809, 775, 756, 691, 666 $cm^{-1}$ 41 μl of ethyl chloroformate, followed by 60 μl of triethylamine, are added at 0° C. under nitrogen to a solution of 250 mg of the above-described acid in 3 ml of tetrahydrofuran, and it is stirred for 10 more minutes. 162 μl of 25% ammonium hydroxide solution is now added and stirred for 1 hour. Then, it is concentrated by evaporation in a vacuum, the residue is diluted with ethyl acetate, washed with 10% citric acid and saturated sodium chloride solution, dried on sodium sulfate, and after filtration, it is concentrated by evaporation in a vacuum. The residue that is thus obtained is purified by chromatography on silica gel. With hexane/0–100% ethyl acetate, 260 mg of the amide is obtained as a colorless oil.

IR (Film): 2928, 2855, 2360, 1634, 1338, 1254, 1071, 994, 836, 776, 756, 691, 668 $cm^{-1}$ 712 mg of tetrabutylammonium fluoride×3 $H_2O$ is added at room temperature under nitrogen to a solution of 260 mg of the above-described silyl ether in 12 ml of tetrahydrofuran, and it is stirred for 6 more hours at room temperature. Then, it is diluted with ethyl acetate, washed with saturated sodium chloride solution, the organic phase is dried on sodium sulfate, and after filtration, it is concentrated by evaporation in a vacuum. The residue that is thus obtained is purified by chromatography on silica gel. With hexane/0–100% ethyl acetate/0–20% methanol, 158 mg of the title compound is obtained as a colorless oil.

IR (Film): 3470, 3400, 2920, 2860, 1740, 1680, 1600, 1490, 1440, 1370, 1340, 1240, 1100, 1050, 1000, 760, 690, 530 $cm^{-1}$ In the figures, the structural formulas and the essential production parameters in addition to the examples are explained.

In Vivo Test Systems (i). Production of human polymorphonuclear leukocytes (PMN)

PMNs of healthy volunteers are isolated from heparinized venous blood by dextran sedimentation and subsequent centrifuging via Ficoll-Histopaque(R). The remaining erythrocytes are eliminated by hypotonic lysis in 0.2% sodium chloride solution. The PMNs are resuspended in Hank's balanced salt solution (HBSS) and mixed with egg albumin (OVA) or bovine serum albumin (BSA).

(ii). $LTB_4$-Receptor-Competition-Binding Test

Human PMNs are incubated together with OVA with tritium-labeled leukotriene-$B_4$ ($LTB_4$) in the presence or absence of the tested substances at concentrations of 10 μmol/l to 0.05 mmol/l in HBSS. Cell-bonded, tritium-labeled $LTB_4$ is separated from the free ligands by vacuum filtration by a glass fiber filter and measured in a scintillation measuring device. The non-specific binding of tritium-labeled $LTB_4$ is determined in the presence of excess unlabeled LTB$_4$ (500 nmol/l). Competition factor (CF) is calculated from the ratio of the concentration of the substance to the concentration of the LTB$_4$, which results in a 50% reduction of the tritium-labeled LTB$_4$-receptor bond.

(iii). LTB$_4$-induced Chemotaxis Test

The chemotaxis test is carried out with modified Boyden chambers, which consist of Transwell$^{(R)}$ modules with polyvinylpyrrolidone-clad polycarbon filters with a pore size of 3 μm. The upper chamber part contains the human PMNs in HBSS, which is supplemented with BSA or OVA. The lower chamber part is to be added with just buffer or with the chemotactically active leukotriene B$_4$ (LTB$_4$) at a concentration within the limits of 1 nmol/l to 100 nmol/l in the presence or absence of the test substance. The chamber is incubated for 60 minutes in water-saturated atmosphere with 5% carbon dioxide. The number of PMNs, which have found their way into the lower chamber part, is determined in a calibrated test by the measurement of the activity of the enzyme myeloperoxidase (MPO). The enzyme activity is measured by spectrometry (450 nm) by determining the rate of H$_2$O$_2$-dependent oxidation of aromatic amine 3,3',5,5'-tetramethylbenzidine (TMB).

The EC$_{50}$ value is determined graphically by the non-linear regression curve. The K$_B$ value describes the capabilities of the competitive antagonist. The K$_B$ value is determined as the antagonist concentration that is necessary to raise the EC$_{50}$ value of the agonist by a factor of 2.

The K$_B$ value is calculated as follows:

K$_B$=[LTB$_4$-receptor-antagonist]/(DR-1)

(DR=the ratio of the LTB$_4$ concentration that is required for half-maximum stimulation in the presence of the antagonist, to the LTB$_4$ concentration that is required for half-maximum stimulation in the absence of the antagonist.)

(iv). LTB$_4$/iloprost-induced skin inflammation in the ears of mice

Female NMRI mice that weigh 26 to 28 g and are 5 to 6 weeks old are used for this in vivo experiment. Ten animals per group are divided at random and kept separate in the various treatment groups. The animals had free access to food and water. To prevent the oral absorption of LTB$_4$/iloprost solutions that are to be administered topically, restraining collars are fastened around the necks of the animals under ether anesthesia shortly before the topical application.

Leukotriene B$_4$ (LTB$_4$) and the stable prostacyclin derivative iloprost is dissolved in ethanol/isopropyl myristat (95+5 v/v) at a concentration of 0.003% (w/v). 10 μl of the LTB$_4$/iloprost solution is administered topically on the outside surface of each ear (surface area about 1 cm$^2$/ear). This corresponds to a dose of 0.3 μg per ear or about 0.3 μg per cm$^2$. Animals that are treated with just LTB$_4$/iloprost solution develop the typical features of inflamed skin with the formation of edemas and infiltration of neutrophiles. These animals are used as a positive control. Animals that were treated with just ethanol/isopropyl myristat (95+5 v/v) on the outside surface of each ear (surface area of about 1 cm$^2$/ear) are used as a negative control.

The effect of the LTB$_4$-receptor-antagonist on the LTB$_4$/iloprost-induced inflammation reaction is determined either with a topical administration or with an intragastric administration of the test substance.

For topical application, the test substance is dissolved in an LTB$_4$/iloprost solution at various concentrations. 10 μl of this solution is applied topically on the outside surface of the ear.

For intragastric administration, the LTB$_4$-receptor-antagonist is dissolved in ethanol. Immediately after the topical administration with LTB$_4$/iloprost, the LTB$_4$-receptor-antagonist or only the solvent is administered intragastrically at various doses with the aid of a probe. The maximum final concentration of ethanol is 3%. The amount of ethanol decreases with additional dilution steps.

The animals are sacrificed 24 hours after the inflammatory reaction sets in. The ears are separated, weighed, flash-frozen and stored for other studies. The peroxidase activity is determined by spectrometry in the homogenate of the ear skin. The tissue is homogenized in HTAB buffer (0.5% hexadecyltrimethylammonium bromide (w/v) in 10$^{-3}$ mol/l of 3-[N-morpholino]propanesulfonic acid with pH 7.0) for 20 seconds with a Polytron$^{(R)}$ PT 3000 (Kinematica AG, Switzerland) at a rotation of 30,000 rpm. The homogenate is centrifuged for 20 minutes at 10° C. and at 14,500 rpm (20,000 g) in a Sorvall RC2-B centrifuge (SM-24 rotor). The aqueous supernatant is suctioned off and its peroxidase activity is tested at a dilution of 1 to 50 in HTAB buffer. The peroxidase activity is determined by photometric measurement of the rate of H$_2$O$_2$-dependent oxidation of the aromatic amine 3,3',5,5'-tetramethylbenzidine (TMB). In a 96-hole microtiter plate, the dilute supernatants are incubated with TMB solution and hydrogen peroxide (solution of 6.5 mg of 3,3',5,5'-tetramethylbenzidine dihydrochloride in 1 ml of dimethyl sulfoxide (DMSO); 1:100 (v/v), dissolved with 0.1 mol/l of sodium-acetate-citrate buffer, pH 6.0, final concentration in the incubation mixture: 1.57·10$^{-4}$ mol/l) (hydrogen peroxide 30% H2O2 1: 16860 (v/v) dissolved with 0.1 mol/l of sodium-acetate-citrate-buffer, pH 6.0, final concentration in the incubation mixture: 4.93·10$^{-5}$ mol/l). After 30 minutes at room temperature, the reaction is stopped by adding 0.5 mol/l of sulfuric acid. The extinction is determined at 450 nm (maximum absorption) in a microtiter-plate measuring device.

EXAMPLE 1

Beispiel 1

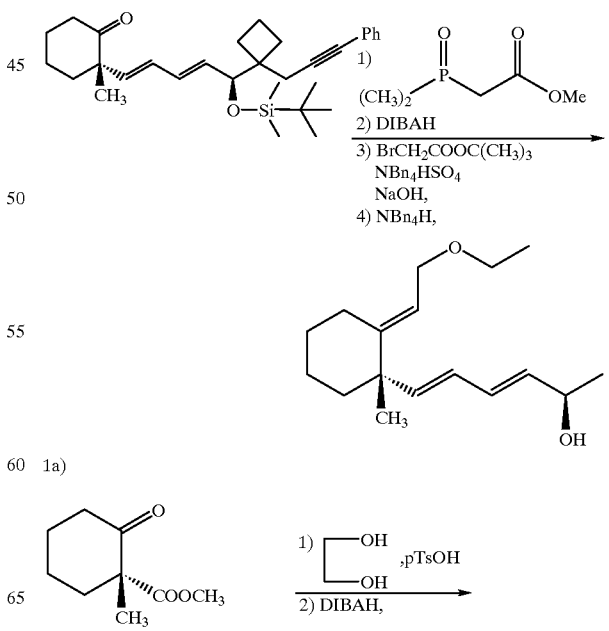

1a)

53
-continued
1b)
1c)
1d)
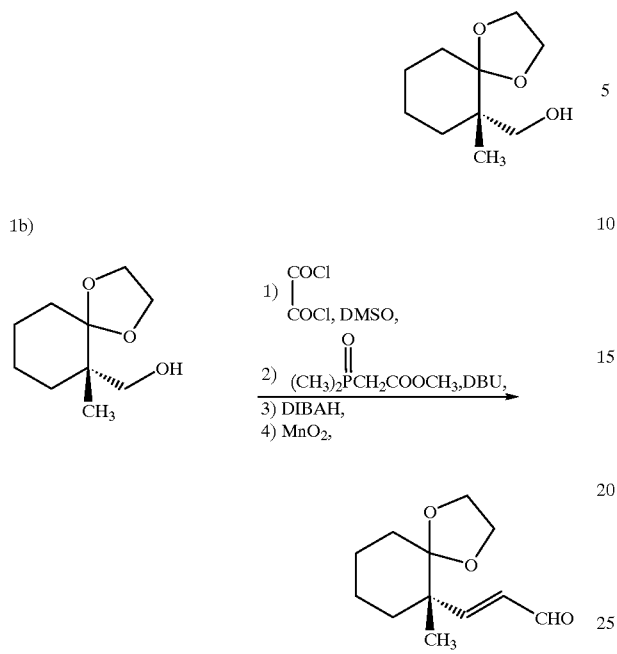
EXAMPLE 2
Beispiel 2
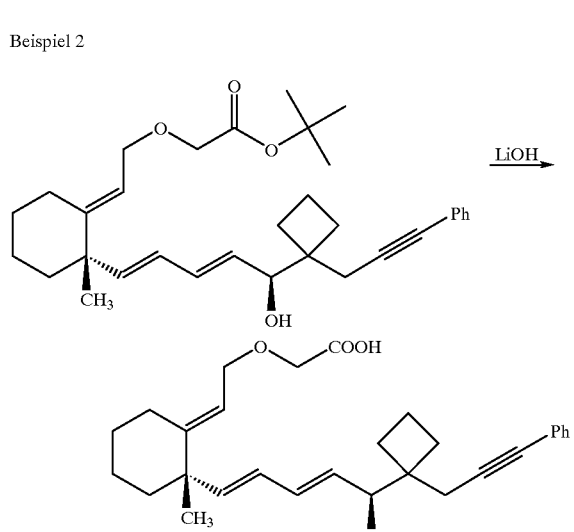
EXAMPLE 3
Beispiel 3 As in Example 1
Wie Beispiel 1
3a)
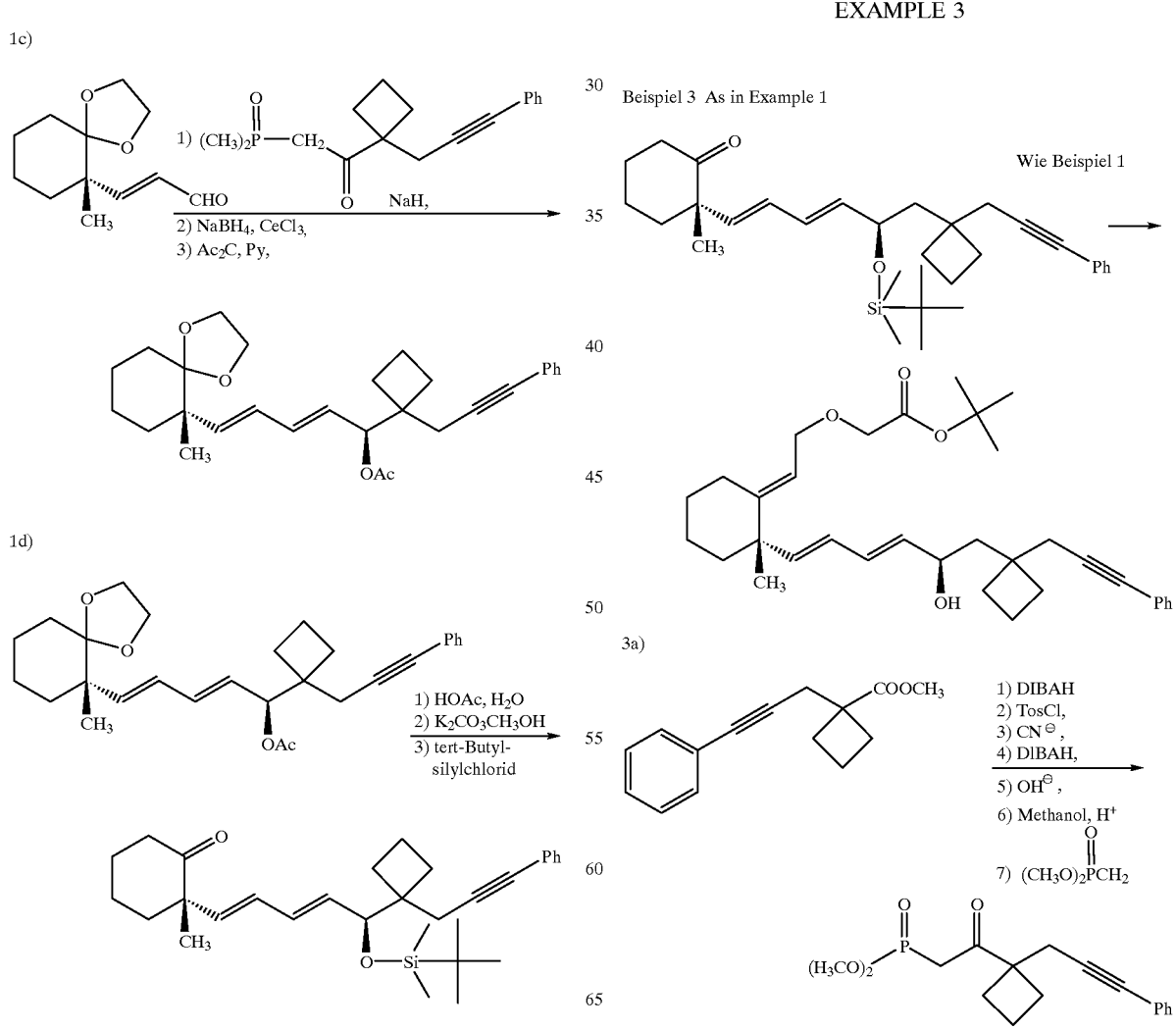

-continued
3b)
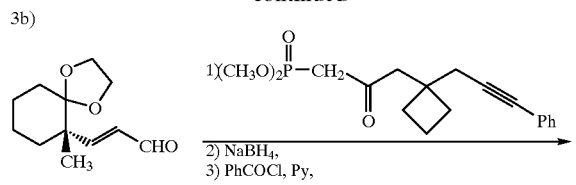
3c)
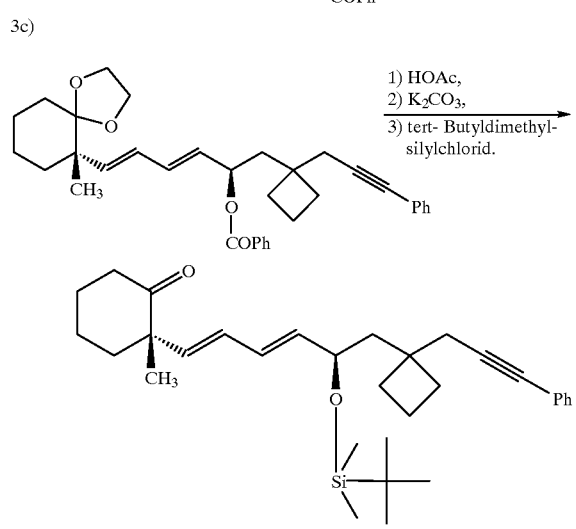
EXAMPLE 4
Beispiel 4
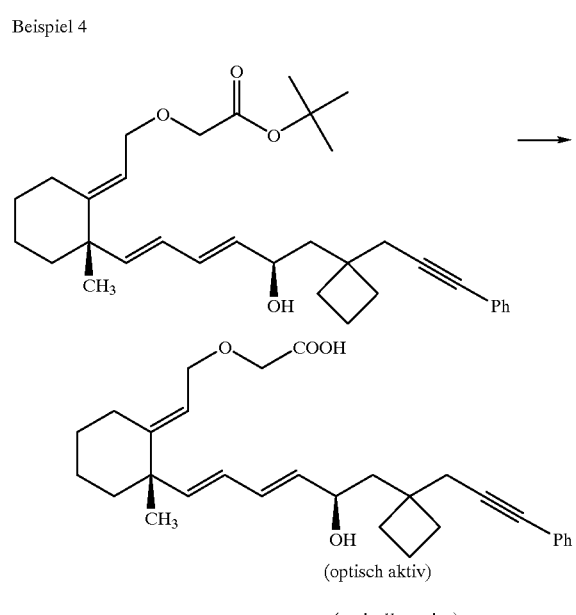
(optisch aktiv)
(optically active)
EXAMPLE 5
racemic As in Example 1
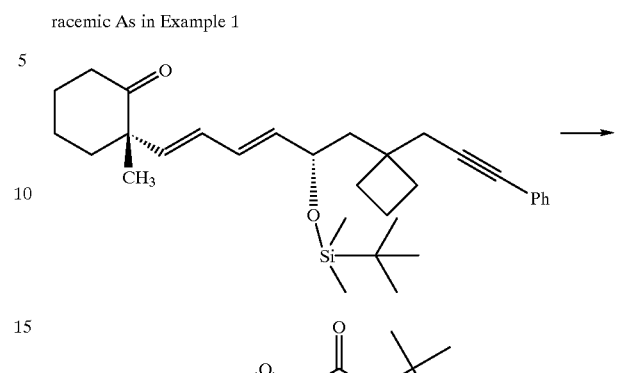
5a)
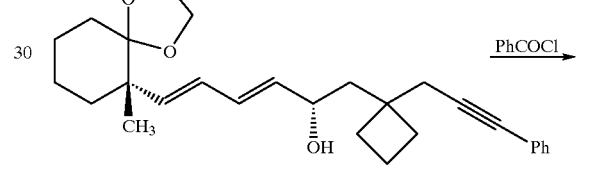
from Example 3b)
5b)
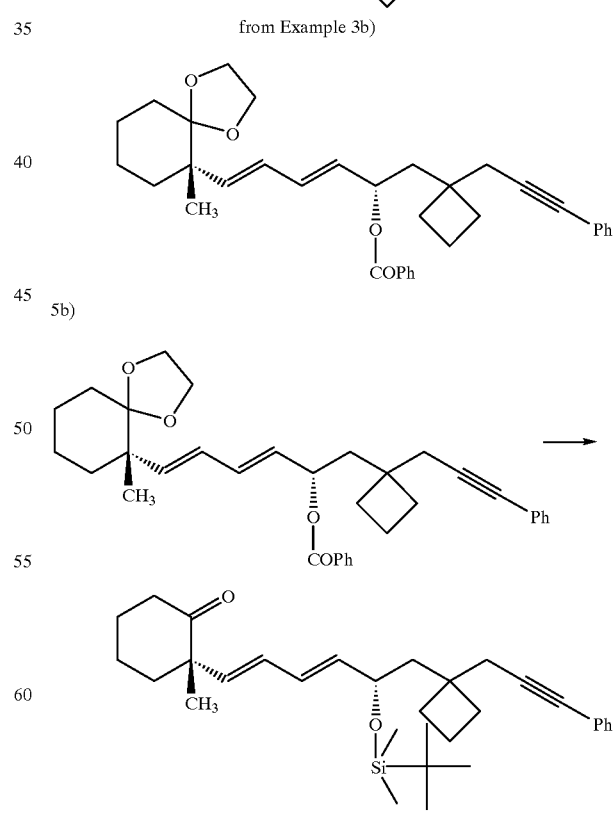

EXAMPLE 6
Beispiel 6
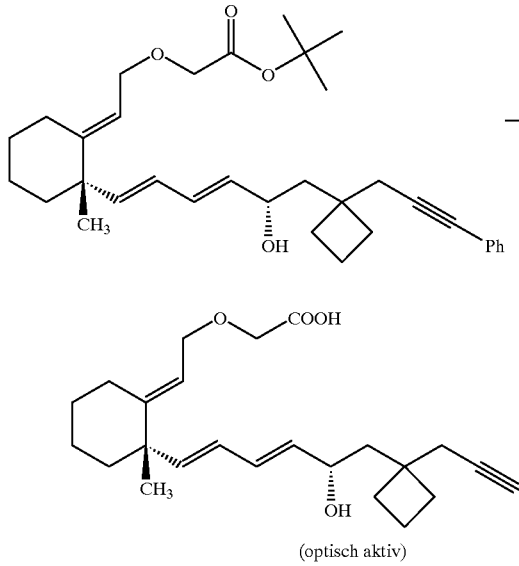
(optisch aktiv)
(optically active)
EXAMPLE 7
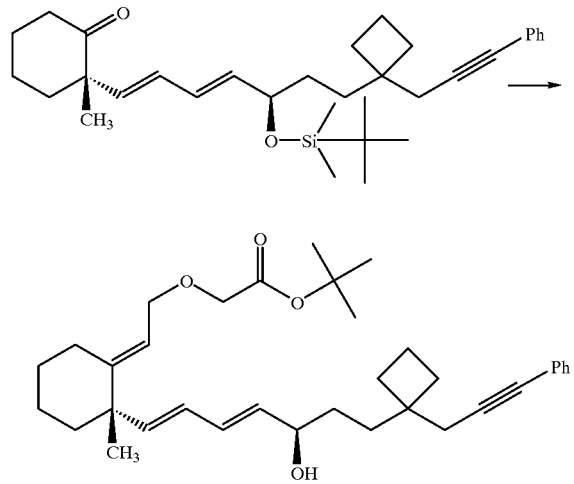
9a)
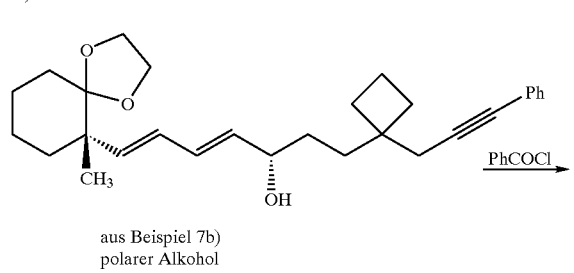
aus Beispiel 7b)
polarer Alkohol
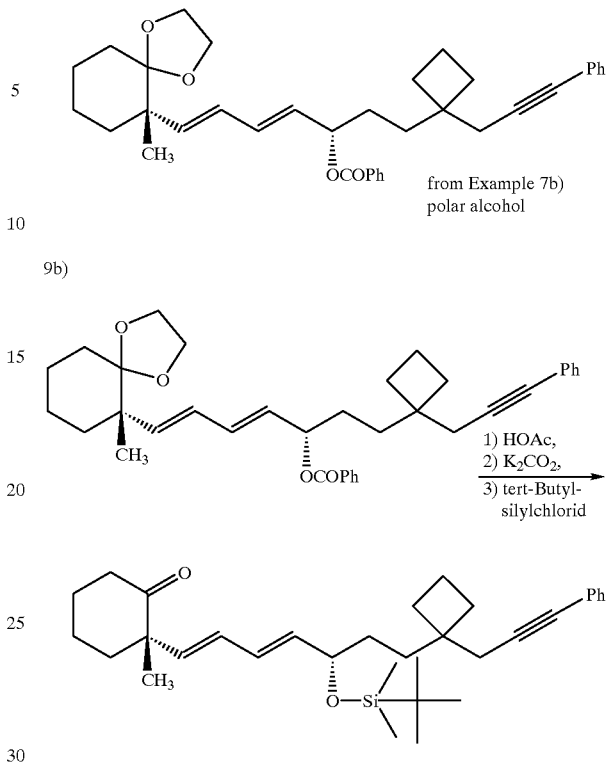
from Example 7b)
polar alcohol
9b)
1) HOAc,
2) K₂CO₂,
3) tert-Butyl-
   silylchlorid
EXAMPLE 10
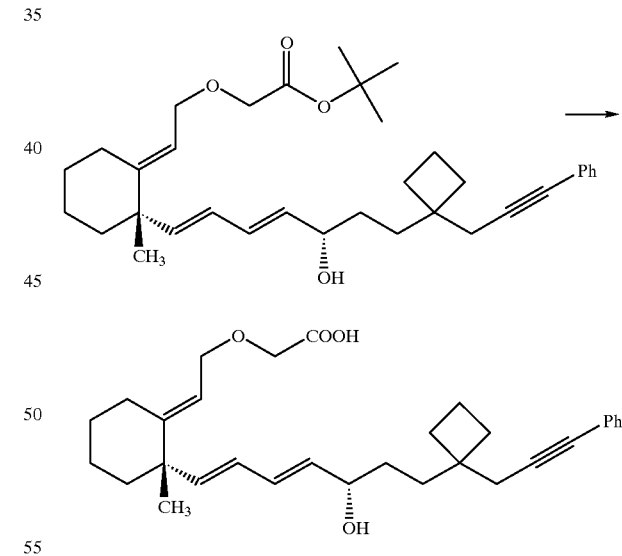
EXAMPLE 11

-continued
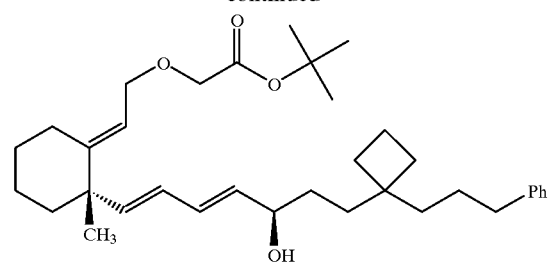
EXAMPLE 12
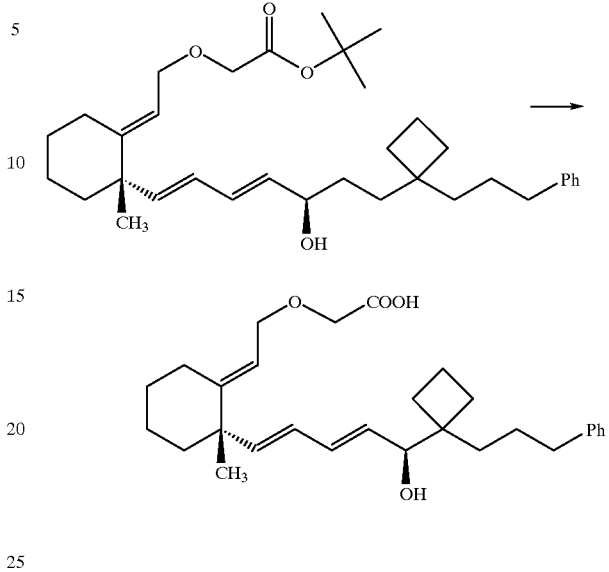
EXAMPLE 13
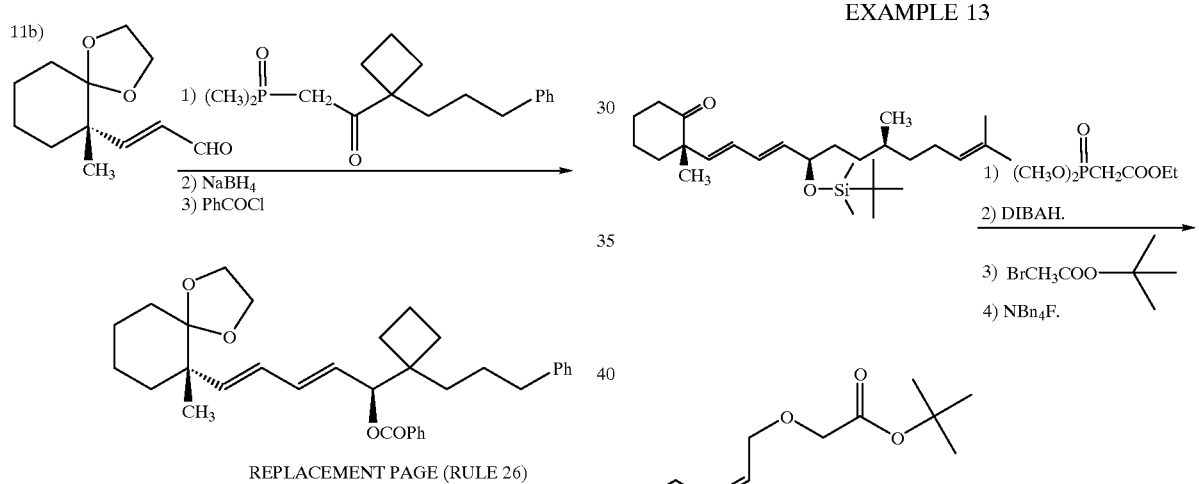
13a)
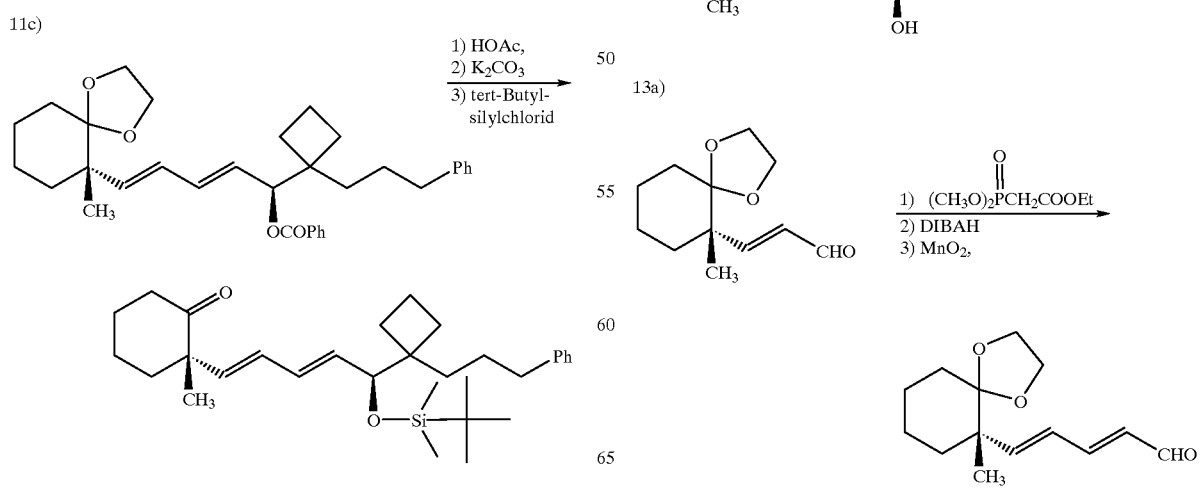

-continued
13b)
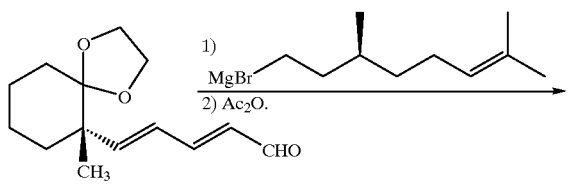
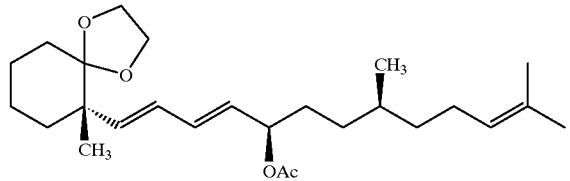
13c)
EXAMPLE 14
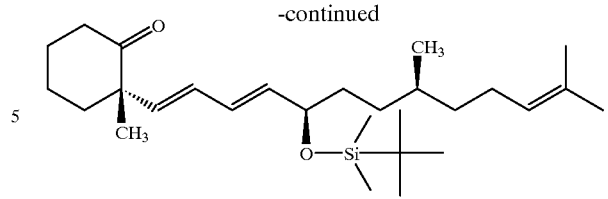
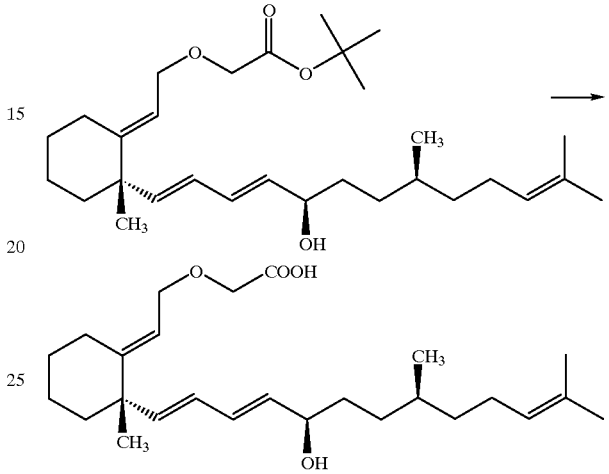
EXAMPLE
15a) Beispiel 15
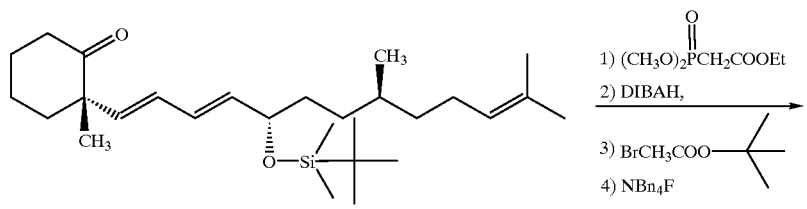
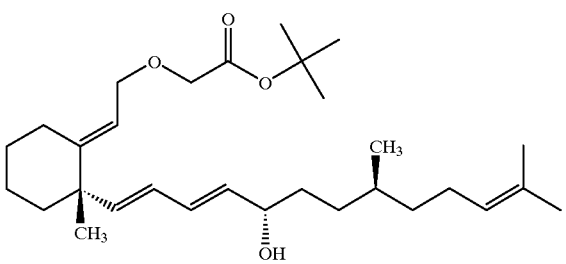
15a)
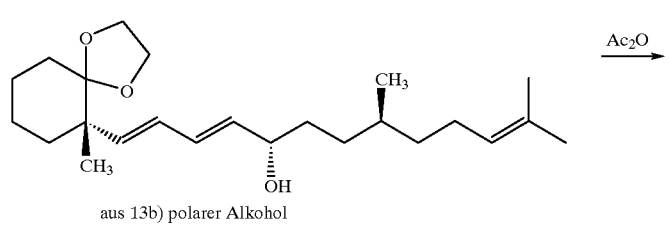
aus 13b) polarer Alkohol -continued
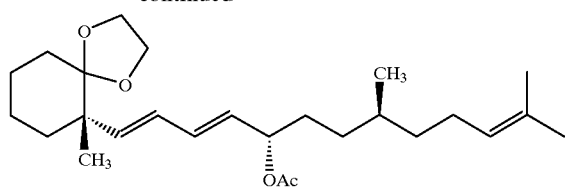
from 13b) polar alcohol
15b)
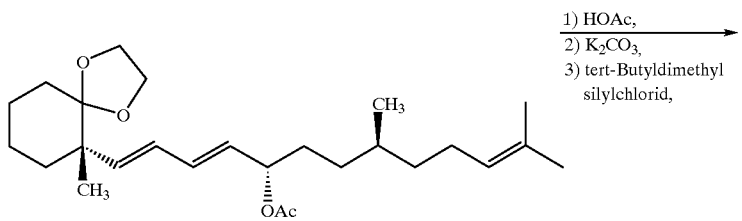
1) HOAc,
2) K$_2$CO$_3$,
3) tert-Butyldimethyl silylchlorid,
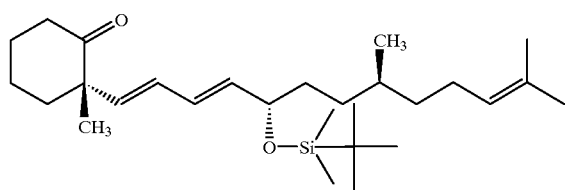
15b)
EXAMPLE 16
Beispiel 16
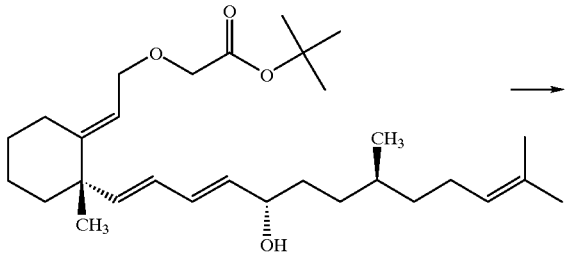
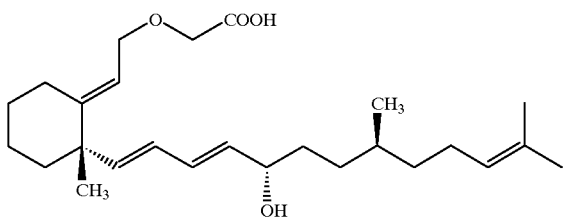
EXAMPLE 17
Beispiel 17
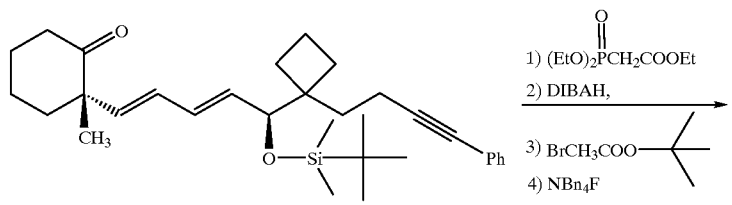
1) (EtO)$_2$PCH$_2$COOEt
2) DIBAH,
3) BrCH$_3$COO-tBu
4) NBn$_4$F

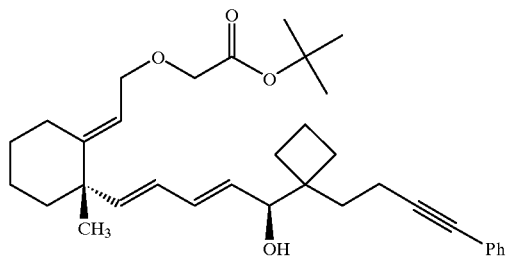
17a)
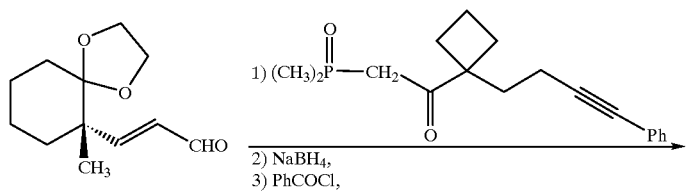
17b)
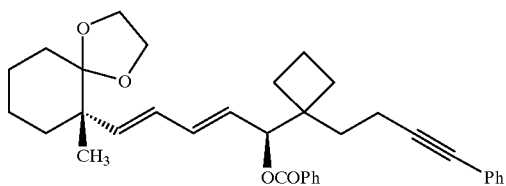
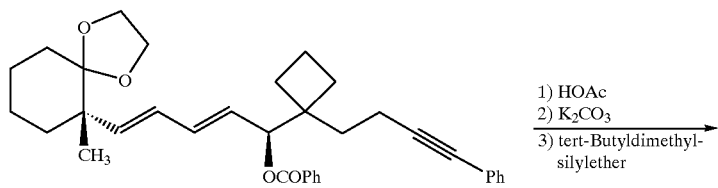
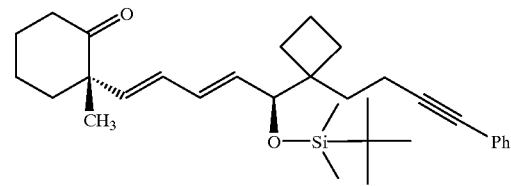
EXAMPLE 18
Beispiel 18
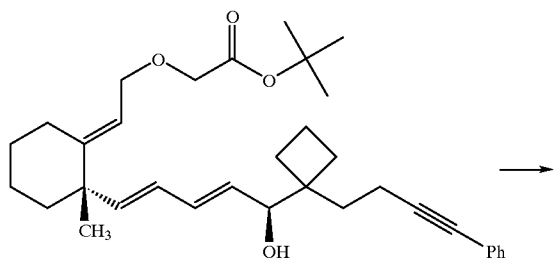 → 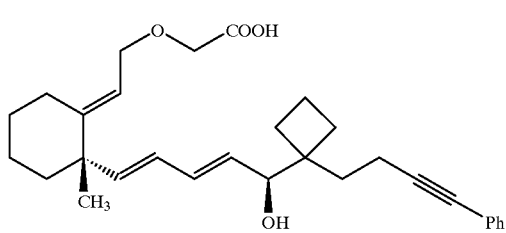

EXAMPLE 19
Beispiel 19
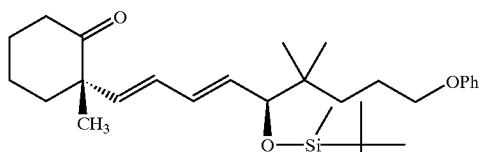
1) $(EtO)_2P(O)CH_2COOEt$
2) DIBAH,
3) BrCOO-C(CH_3)_3
4) $NBn_4F$
19a)
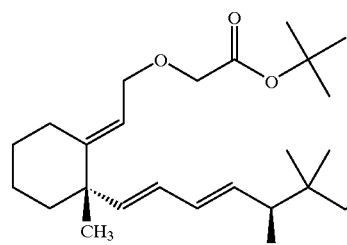
19b)
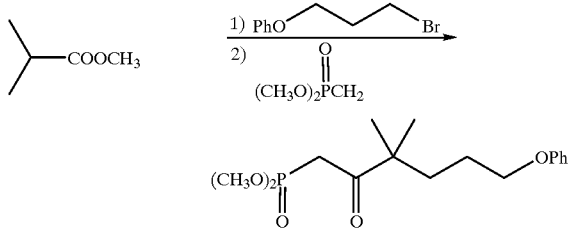
1) $(CH_3)_2P(O)-CH_2-$ [side chain with OPh]
2) $NaBH_4$,
3) PhCOCl,
19c)
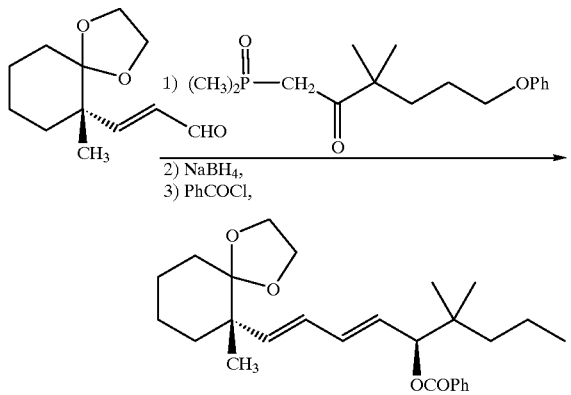
1) HOAc
2) $K_3CO_3$
3) tert-Butyldimethyl-silylether
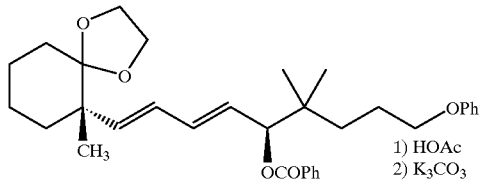
1) PhO-CH_2CH_2CH_2-Br
2) $(CH_3O)_2PCH_2$-
    O
-continued
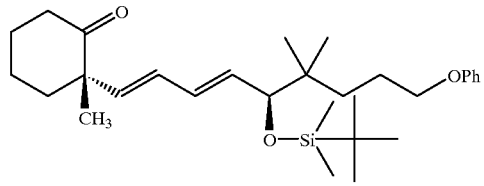
EXAMPLE 20
Beispiel 20
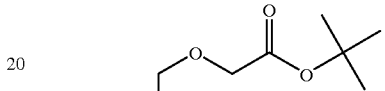
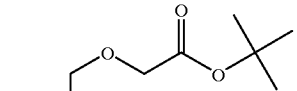
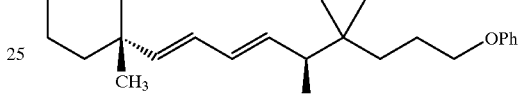
EXAMPLE 21
Beispiel 21
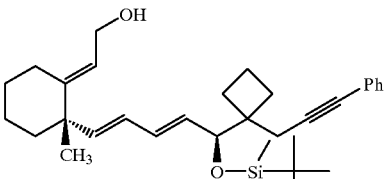
aus Beispiel 1)
1) $BrCH_2CH_2CH_2-C(OMe)_3$
2) $Bn_4NF$,
3) LiOH,
from Example 1)

EXAMPLE 22
Beispiel 22
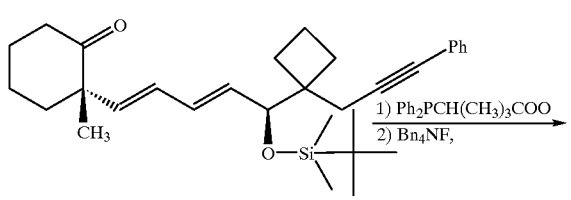
EXAMPLE 23
Beispiel 23
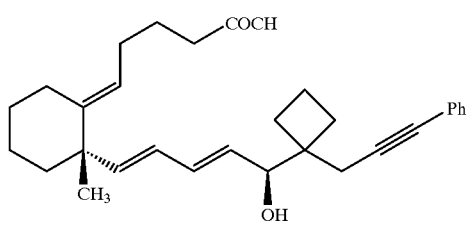
aus Beispiel 1)
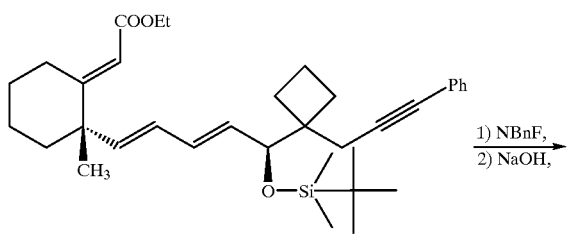
from Example 1)
EXAMPLE 24
Beispiel 24
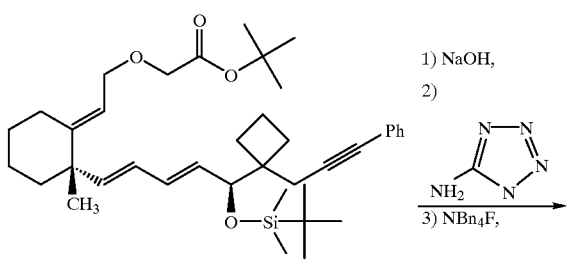
-continued
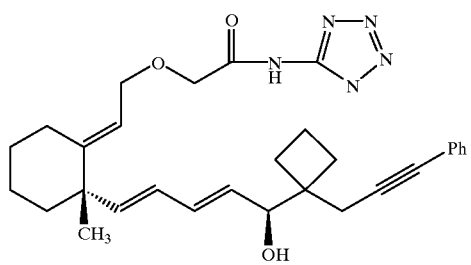
EXAMPLE 25
Beispiel 25
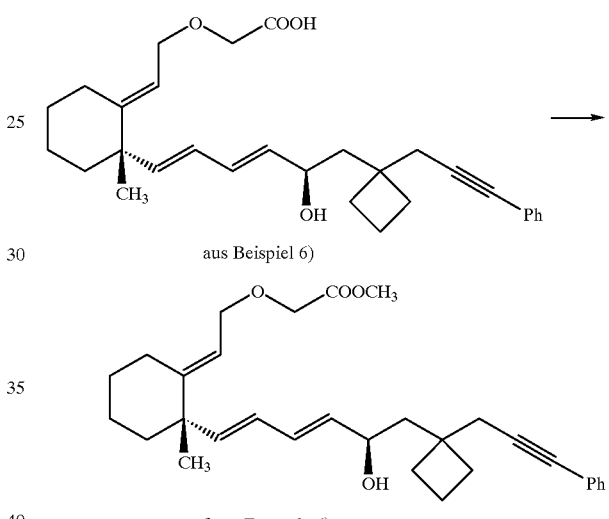
aus Beispiel 6)
from Example 6)
EXAMPLE 26
Beispiel 26
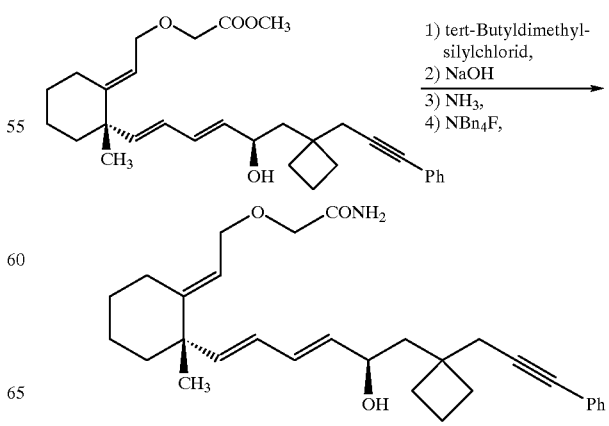

7a)

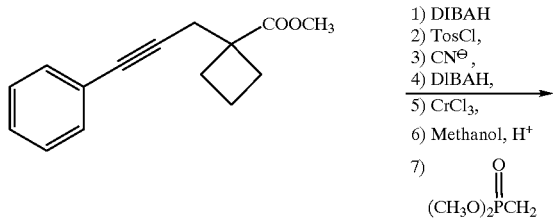

1) DIBAH
2) TosCl,
3) CN⊖,
4) DlBAH,
5) CrCl₃,
6) Methanol, H⁺
7) 
$$(CH_3O)_2\overset{O}{P}CH_2$$

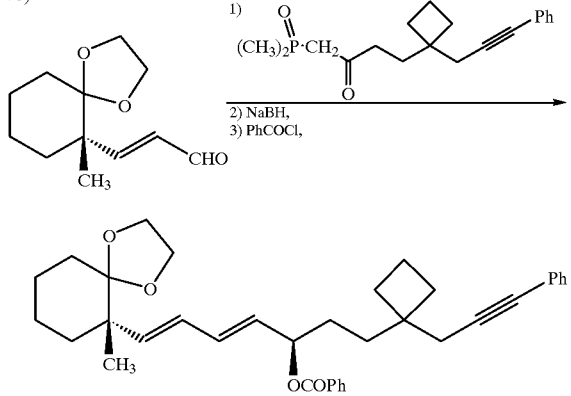

from Example 3a)

7b)

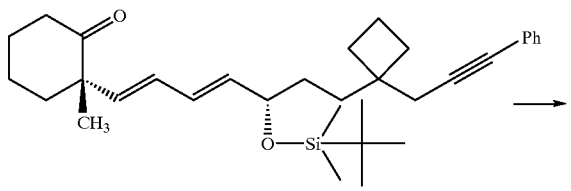

1) $(CH_3)_2\overset{O}{P}\cdot CH_2$ ...
2) NaBH,
3) PhCOCl,

7c)

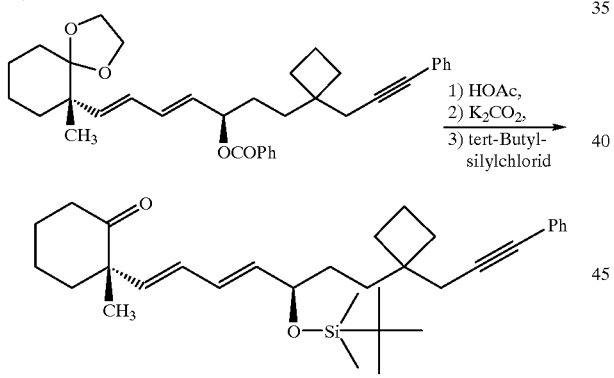

1) HOAc,
2) K₂CO₃,
3) tert-Butyl-silylchlorid

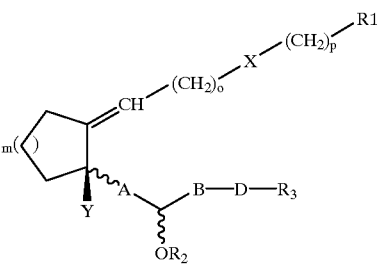

EXAMPLE 8

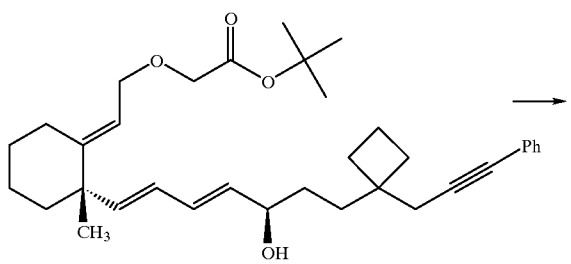

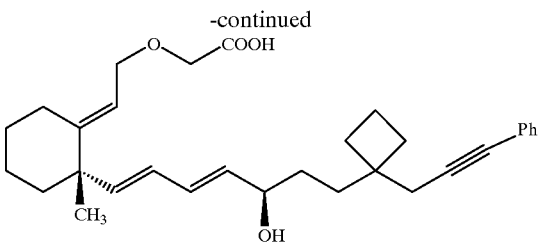

EXAMPLE 9

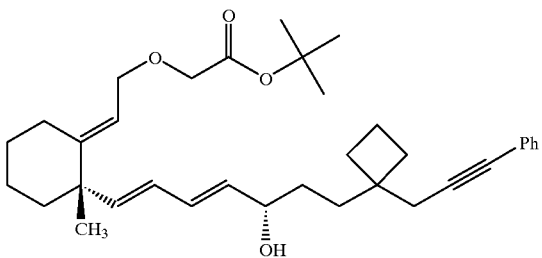

What is claimed is:

1. A leukotriene-B₄ derivative of formula I (I)

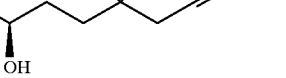

wherein
- $R_1$ is CH₂OH, CH₃, CF₃, COOR₄, or CONR₅R₆,
- $R_2$ is H or an organic acid radical with 1–15 C atoms,
- $R_3$ is H; C₁–C₄ alkyl optionally substituted by halogen atoms or phenyl; C₃–C₁₀ cycloalkyl optionally substituted in one or more places by C₁₋₄ alkyl or halogen atoms; C₆–C₁₀ aryl optionally substituted in one or more places by halogen, phenyl, C₁–C₄ alkyl, C₁–C₄ alkoxy, fluoromethyl, chloromethyl, trifluoromethyl, carbonyl, carboxyl or hydroxy; or a 5- to 6-membered aromatic heterocyclic ring with at least 1 heteroatom,
- $R_4$ is hydrogen; C₁–C₁₀ alkyl, C₃–C₁₀ cycloalkyl, or C₆–C₁₀ aryl in each case optionally substituted by 1–3 halogen, phenyl, C₁–C₄ alkyl, C₁–C₄ alkoxy, fluoromethyl, chloromethyl, trifluoromethyl, carboxyl or hydroxy; CH₂—CO—(C₆–C₁₀) aryl; or a 5- to 6-membered ring with at least 1 heteroatom,
- A is trans, trans-CH=CH—CH=CH, —CH₂CH₂—CH=CH— or tetramethylene, B is $C_1$–$C_{10}$ straight-chain or branched-chain alkylene, which is optionally substituted by fluorine, or is

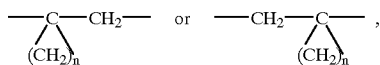

D is a direct bond, oxygen, sulfur, —C≡C—, —CH=CR$_7$— or together with B can also be a direct bond;

$R_5$ and $R_6$ are the same or different, and are each H or $C_1$–$C_4$ alkyl optionally substituted by hydroxy groups, or $R_6$ is H and $R_5$ is $C_1$–$C_{15}$ alkanoyl or $R_8SO_2$, $R_7$ is H, $C_1$–$C_5$ alkyl, chlorine, or bromine, $R_8$ is H; $C_1$–$C_{14}$ alkyl optionally substituted by halogen atoms or phenyl; $C_3$–$C_{10}$ cycloalkyl optionally substituted in one or more places by $C_{1-4}$ alkyl or halogen atoms; $C_6$–$C_{10}$ aryl optionally substituted in one or more places by halogen, phenyl, $C_1$–$C_4$ alkyl, $C_1$–$C_4$ alkoxy, fluoromethyl, chloromethyl, trifluoromethyl, carbonyl, carboxyl or hydroxy; or a 5- to 6-membered aromatic heterocyclic ring with at least 1 heteroatom, m is 1–3, n is 2–5, o is 0–5, p is 0–5, X is a direct bond, oxygen, or sulfur, and Y is $C_1$–$C_8$ alkyl optionally substituted in one or more places, or $C_3$–$C_{10}$ cycloalkyl optionally substituted by aryl, and, if $R_4$ is hydrogen, salts thereof with physiologically compatible bases and cyclodextrin clathrates thereof.

2. A pharmaceutical composition comprising a leukotriene-$B_4$ derivative according to claim 1, and an additive for forming a solution, cream or ointment.

3. A process for production of leukotriene-$B_4$ derivatives according to claim 1, comprising reacting a ketone of formula II

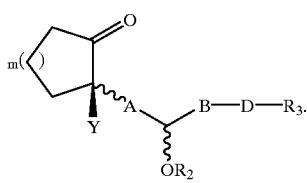

optionally under protection of free hydroxy groups in $R_2$, with an olefination reagent of formula III,

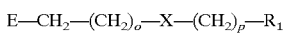

wherein E is

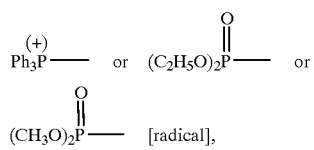

in the presence of a base, and optionally separating isomers, optionally releasing protected hydroxy groups, optionally etherifying a free hydroxy group optionally oxidizing the 1-hydroxy group to carboxylic acid and/or is reduced, optionally esterifying a carboxyl group optionally converting a free carboxyl group into an amide, or optionally a carboxyl group is converted into a salt with a physiologically compatible base.

4. A compound according to claim 1, wherein Y is $C_1$–$C_8$ alkyl or $C_3$–$C_{10}$ cycloalkyl.

5. A compound according to claim 4, wherein the group $OR_2$ is in the α-position.

6. A compound according to claim 4, wherein the group $OR_2$ is in the β-position.

7. A compound according to claim 4, wherein $R_4$ is H;

straight-chain or branched-chain alkyl having 1–10 C atoms;

cycloalkyl having 3–10 C atoms which is optionally substituted by alkyl having 1–4 C atoms;

aryl having 6–10 C atoms which is optionally substituted by 1–3 halogen atoms, phenyl, 1–3 alkyl groups having 1–4 C atoms, chloromethyl, fluoromethyl, trifluoromethyl, carboxyl, hydroxy or alkoxy having 1–4 C atoms; or a 5- or 6-membered aromatic heterocycle selected from 2-furyl, 2-thienyl, 2-pyridyl, 3-pyridyl, 4-pyridyl, oxazolyl, thiazolyl, pyrimidinyl, pyridazinyl, 3-furyl, 3-thienyl, and 2-tetrazolyl.

8. A compound according to claim 4, wherein $R_2$ is H or an acid radical selected from the following acids:

formic acid, acetic acid, propionic acid, butyric acid, isobutyric acid, valeric acid, isovaleric acid, caproic acid, ethanic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopentylacetic acid, cyclohexylacetic acid, cyclohexanecarboxylic acid, phenylacetic acid, phenoxyacetic acid, methoxyacetic acid, ethoxyacetic acid, monochloroacetic acid, dichloroacetic acid, trichloroacetic acid, aminoacetic acid, diethylaminoacetic acid, piperidinoacetic acid, morpholinoacetic acid, lactic acid, succinic acid, adipic acid, nicotinic acid, isonicotinic acid, furan-2-carboxylic acid, cyclopentylpropionic acid, benzoic acid and benzoic acid substituted with F, Cl, Br, trifluoromethyl, hydroxy, $C_1$ alkoxy or carboxy groups.

9. A compound according to claim 4, wherein $R_3$ is a straight-chain or branched-chain, saturated or unsaturated alkyl group having 1–14 C atoms which is optionally substituted by phenyl or halogen atoms.

10. A compound according to claim 4, wherein $R_3$ is a cycloalkyl group selected from cyclopropyl, cyclobutyl, cyclopentyl, cyclohexyl, methylcyclohexyl, and fluorocyclohexyl.

11. A compound according to claim 4, wherein $R_3$ is phenyl, 1-naphthyl or 2-naphthyl which is optionally substituted by 1–3 halogen atoms, phenyl, 1–3 alkyl groups having 1–4 C atoms, chloromethyl, fluoromethyl, trifluoromethyl, carboxyl, $C_1$–$C_4$ alkoxy, or hydroxy.

12. A compound according to claim 4, wherein $R_3$ is a 5- and/or 6-membered heterocyclo selected from 2-furyl, 1-thienyl, 2-pyridyl, 3-pyridyl, 4-pyridyl, oxazolyl, thiazolyl, pyrimidinyl, pyridazinyl, pyrazinyl, 3-furyl, and 3-thienyl.

13. A compound according to claim 4, wherein group B is selected from methylene, fluoromethylene, difluoromethylene, ethylene, 1,2-propylene, ethylethylene, trimethylene, tetramethylene, pentamethylene, 1,2-difluoroethylene, 1-fluoroethylene, 1-methyltetramethylene, 1-methyl-trimethylene, 1-methylene-ethylene, 1-methylene-tetramethylene, or is a group of formula

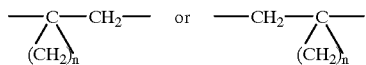

in which n is 3–5.

14. A compound according to claim 1, wherein $R_1$ is $CH_2OH$, $CONR_5R_6$, or $COOR_4$, $R_4$ is a hydrogen, alkyl with 1–10 C atoms, cycloalkyl with 5–6 C atoms, phenyl optionally substituted by 1–2 chlorine, bromine, phenyl, $C_{1-4}$ alkyl, $C_{1-4}$ alkoxy, chloromethyl, fluoromethyl, trifluoromethyl, carboxy or hydroxy, X is an oxygen atom, Y is methyl, p is 1–3, o s 1–3, m is 1–3, A is trans-CH=CH—CH=CH— or tetramethylene;

B is a straight-chain or branched-chain, saturated or unsaturated, alkylene group with up to 10 C atoms, which is optionally substituted by fluorine, or is

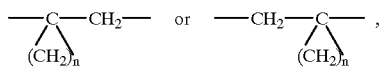

n is 2–5,

D is a direct bond, oxygen, sulfur, —C≡C— or —CH=CR$_7$, $R_7$ is hydrogen, $C_{1-5}$ alkyl, chlorine or bromine;

B and D together are, alternatively, a direct bond;

$R_2$ is hydrogen or an organic acid radical with 1–15 C atoms;

$R_3$ is hydrogen, $C_1$–$C_{10}$ alkyl, cycloalkyl with 5–6 C atoms, or phenyl optionally substituted by 1–2 chlorine, bromine, phenyl, $C_{1-4}$ alkyl, $C_{1-4}$ alkoxy, chloromethyl, fluoromethyl, trifluoromethyl, carboxy or hydroxy, or if $R_4$ is hydrogen, a salt thereof with a physiologically compatible base, or a cyclodextrin clathrate thereof.

15. A compound according to claim 1, wherein $R_1$ is $CH_2OH$, $CONR_5R_6$, or $COOR_4$ $R_4$ is hydrogen, or alkyl with 1–4 C atoms;

$R_2$ is hydrogen or an organic acid radical with 1–6 C atoms;

$R_3$ is hydrogen or $C_{1-10}$ alkyl;

A is trans, trans-CH=CH—CH=CH— or tetramethylene;

B is a straight-chain or branched-chain alkylene group with up to 5 C atoms, or is

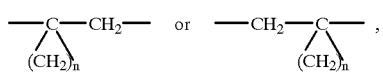

n is 3 or 4;

D is a direct bond, —C≡C— or a —CH=CR$_7$, $R_7$ is hydrogen or $C_{1-5}$ alkyl;

X is an oxygen atom,

Y is methyl, p is 1, o is 1, m is 1, 2;

B and D are, alternatively, a direct bond;

or, if $R_4$ is hydrogen, a salt thereof with a physiologically compatible base, or a cyclodextrin chlathrate thereof.

16. A leukotriene-B$_4$ derivative of formula I

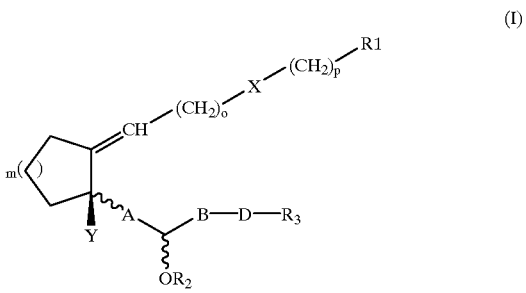

wherein $R_1$ is $CH_2OH$, $CH_3$, $CF_3$, $COOR_4$, or $CONR_5R_6$;

$R_2$ is H or an organic acid radical selected from formic acid, acetic acid, propionic acid, butyric acid, isobutyric acid, valeric acid, isovaleric acid, caproic acid, ethanic acid, caprylic acid, pelargonic acid, capric acid, undecylic acid, lauric acid, tridecylic acid, myristic acid, pentadecylic acid, trimethylacetic acid, diethylacetic acid, tert-butylacetic acid, cyclopentylacetic acid, cyclohexylacetic acid, cyclohexanecarboxylic acid, phenylacetic acid, phenoxyacetic acid, methoxyacetic acid, ethoxyacetic acid, monochloroacetic acid, dichloroacetic acid, trichloroacetic acid, aminoacetic acid, diethylaminoacetic acid, piperidinoacetic acid, morpholinoacetic acid, lactic acid, succinic acid, adipic acid, benzoic acid, benzoic acid substituted with F, Cl, Br, trifluoromethyl, hydroxy, $C_{1-4}$ alkoxy or carboxy groups; nicotrinic acid, isonicotinic acid, furan-2-carboxylic acid, and cyclopentylpropionic acid, $R_3$ is H; methyl, ethyl, propyl, butyl, isobutyl, tert-butyl, pentyl, hexyl, heptyl, octyl, butenyl, isobutenyl, propenyl, pentenyl, benzyl, m-chlorobenzyl, p-chlorobenzyl; cyclopropyl, cyclobutyl, cyclopentyl, cyclohexyl, methylcyclohexyl, fluorocyclohexyl; phenyl, 1-naphthyl or 2-naphthyl which is optionally substituted by 1–3 halogen atoms, phenyl, 1–3 alkyl groups having 1–4 C atoms, chloromethyl, fluoromethyl, trifluoromethyl, carboxyl, $C_1$–$C_4$ alkoxy, or hydroxy; 2-furyl, 1-thienyl, 2-pyridyl, 3-pyridyl, 4-pyridyl, oxazolyl, thiazolyl, pyrimidinyl, pyridazinyl, pyrazinyl, 3-furyl, or 3-thienyl;

$R_4$ is H; straight-chain or branched-chain alkyl having 1–10 C atoms which is optionally substituted by halogen atoms, methoxy, ethoxy, aryl having 6–10 C atoms, aroyl having 6–10 C atoms, dialkylamino wherein the alkyl portions have 1–4 C atoms, or trialkylammonium wherein the alkyl portions have 1–4 C atoms; cycloalkyl having 3–10 C atoms which is optionally substituted by alkyl having 1–4 C atoms; aryl having 6–10 C atoms which is optionally substituted by 1–3 halogen atoms, phenyl, 1–3 alkyl groups having 1–4 C atoms, chloromethyl, fluoromethyl, trifluoromethyl, carboxyl, hydroxy or alkoxy having 1–4 C atoms; 2-furyl, 2-thienyl, 2-pyridyl, 3-pyridyl, 4-pyridyl, oxazolyl, thiazolyl, pyrimidinyl, pyridazinyl, 3-furyl, 3-thienyl, or 2-tetrazolyl;

A is trans, trans-CH=CH—CH=CH, —CH$_2$CH$_2$—CH=CH— or tetramethylene;

B is $C_1$–$C_{10}$ straight-chain or branched-chain alkylene, which is optionally substituted by fluorine, or is

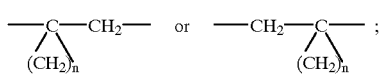

D is a direct bond, oxygen, sulfur, —C≡C—, —CH=CR$_7$ or together with B can also be a direct bond;

R$_5$ and R$_6$ are the same or different, and are each H or $C_1$–$C_4$ alkyl optionally substituted by hydroxy groups, or R$_6$ is H and R$_5$ is $C_1$–$C_{15}$ alkanoyl or R$_8$SO$_2$, R$_7$ is H, $C_1$–$C_5$ alkyl, chlorine, or bromine, R$_8$ is H; methyl, ethyl, propyl, butyl, isobutyl, tert-butyl, pentyl, hexyl, heptyl, octyl, butenyl, isobutenyl, propenyl, pentenyl, benzyl, m-chlorobenzyl, p-chlorobenzyl; cyclopropyl, cyclobutyl, cyclopentyl, cyclohexyl, methylcyclohexyl, fluorocyclohexyl; phenyl, 1-naphthyl or 2-naphthyl which is optionally substituted by 1–3 halogen atoms, phenyl, 1–3 alkyl groups having 1–4 C atoms, chloromethyl, fluoromethyl, trifluoromethyl, carboxyl, $C_1$–$C_4$ alkoxy, or hydroxy; 2-furyl, 1-thienyl, 2-pyridyl, 3-pyridyl, 4-pyridyl, oxazolyl, thiazolyl, pyrimidinyl, pyridazinyl, pyrazinyl, 3-furyl, or 3-thienyl;

m is 1–3, n is 2–5, o is 0–5, p is 0–5,

X is a direct bond, oxygen, or sulfur, and

Y is $C_1$–$C_8$ alkyl or $C_3$–$C_{10}$ cycloalkyl optionally substituted by aryl, and, if R$_4$ is hydrogen, salts thereof with physiologically compatible bases and cyclodextrin clathrates thereof.

* * * * *

UNITED STATES PATENT AND TRADEMARK OFFICE
CERTIFICATE OF CORRECTION

PATENT NO.    : 6,340,706 B1
DATED         : January 22, 2002
INVENTOR(S)   : Bernd Buchmann et al.

It is certified that error appears in the above-identified patent and that said Letters Patent is hereby corrected as shown below:

Column 72,
Line 52, after "H;" insert -- $C_{1-14}$ alkyl -- and delete "$C_1$-$C_4$ alkyl"

Signed and Sealed this

Sixteenth Day of December, 2003

JAMES E. ROGAN
*Director of the United States Patent and Trademark Office*